(12) United States Patent
Hoover et al.

(10) Patent No.: US 10,543,230 B2
(45) Date of Patent: *Jan. 28, 2020

(54) REDOX SIGNALING GEL FORMULATION

(71) Applicant: RDG Holdings, Inc., Pleasant Grove, UT (US)

(72) Inventors: Andrew Hoover, Lehi, UT (US); James Pack, Park City, UT (US)

(73) Assignee: RDG HOLDING, INC., Pleasant Grove, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/493,019

(22) Filed: Apr. 20, 2017

(65) Prior Publication Data

US 2017/0216352 A1 Aug. 3, 2017

Related U.S. Application Data

(63) Continuation of application No. 14/321,423, filed on Jul. 1, 2014, now abandoned.

(60) Provisional application No. 61/913,803, filed on Dec. 9, 2013, provisional application No. 61/887,898, filed on Oct. 7, 2013.

(51) Int. Cl.
| | |
|---|---|
| *A61K 33/20* | (2006.01) |
| *A61K 8/04* | (2006.01) |
| *A61K 8/20* | (2006.01) |
| *A61K 8/25* | (2006.01) |
| *A61K 8/19* | (2006.01) |
| *A61K 8/81* | (2006.01) |
| *A61K 9/00* | (2006.01) |
| *A61K 9/06* | (2006.01) |
| *A61K 33/00* | (2006.01) |
| *A61K 33/14* | (2006.01) |
| *A61K 47/02* | (2006.01) |
| *C25B 1/26* | (2006.01) |

(52) U.S. Cl.
CPC .............. *A61K 33/20* (2013.01); *A61K 8/042* (2013.01); *A61K 8/19* (2013.01); *A61K 8/20* (2013.01); *A61K 8/25* (2013.01); *A61K 8/8147* (2013.01); *A61K 9/0014* (2013.01); *A61K 9/06* (2013.01); *A61K 33/00* (2013.01); *A61K 33/14* (2013.01); *A61K 47/02* (2013.01); *C25B 1/26* (2013.01); *A61K 2800/48* (2013.01); *A61K 2800/83* (2013.01)

(58) Field of Classification Search
None
See application file for complete search history.

(56) References Cited

U.S. PATENT DOCUMENTS

| | | |
|---|---|---|
| 1,200,165 A | 10/1916 | Burgess |
| 4,236,992 A | 12/1980 | Themy |
| 4,316,787 A | 2/1982 | Themy |
| 4,671,955 A | 6/1987 | Palinczar |
| 4,787,980 A | 11/1988 | Ackermann et al. |
| 4,810,344 A | 3/1989 | Okazaki |
| 4,956,184 A | 9/1990 | Kross |
| 5,334,383 A | 8/1994 | Morrow |
| 5,507,932 A | 4/1996 | Robinson |
| 5,674,537 A | 1/1997 | Morrow |
| 6,007,686 A | 12/1999 | Welch et al. |
| 6,114,398 A | 9/2000 | Ratcliff |
| 6,117,285 A | 9/2000 | Welch et al. |
| 6,333,054 B1 | 12/2001 | Rogozinski |
| 6,726,091 B1 | 4/2004 | Ehrick et al. |
| 6,821,403 B1 | 11/2004 | Lundquist |
| 7,108,997 B2 | 9/2006 | Kettle |
| 7,691,249 B2 | 4/2010 | Daly et al. |
| 8,062,501 B2 | 11/2011 | Omasa |
| 8,323,252 B2 | 12/2012 | Alimi et al. |
| 8,518,382 B2 | 8/2013 | Speronello et al. |
| 8,673,297 B2 | 3/2014 | Speronello et al. |
| 8,784,900 B2 | 7/2014 | Northey |
| 9,072,793 B2 | 7/2015 | Eckert et al. |
| 9,175,141 B2 | 11/2015 | Wray et al. |
| 9,474,768 B1 | 10/2016 | Richards |
| 9,498,548 B2 | 11/2016 | Alimi |

(Continued)

FOREIGN PATENT DOCUMENTS

| | | |
|---|---|---|
| CN | 101163491 A | 4/2008 |
| CN | 102167997 | 6/2013 |

(Continued)

OTHER PUBLICATIONS

CDC, Salt vs. Sodium, https://www.cdc.gov/salt/sodium_toolkit.htm, retrieved online May 8, 2019 (Year: 2019).*
AlNashef et al. Electrochemical Generation of Superoxide in Room-Termperature Ionic Liquids. Electrochemical and Solid State Letters, 4 (11) D16-D18 (2001).
AlNashef et al. Superoxide Electrochemistry in an Ionic Liquid. Ind. Eng. Chem. Res. 2002, 41, 4475-4478.
Bielski et al. Reactivity of H02/02-Radicals in Aqueous Solution. J. Phys. Chem. Ref. Data, vol. 14, No. 4 1985.
Chen, "Novel technologies for the prevention and treatment of dental caries: a patent survey", Expert Opin Ther Pat. May 2010; 20(5): 681-694.
Hayann et al. Generation and stability of superoxide ion in tris(pentafluoroethyl) trifluorophosphate anion-based ionic liquids. J Fluorine Chem. vol. 142, 2012, 83-89.

(Continued)

*Primary Examiner* — Jennifer A Berrios
(74) *Attorney, Agent, or Firm* — Knobbe, Martens, Olson & Bear LLP

(57) ABSTRACT

Redox signaling gels are disclosed. Such gels include a composition with at least one reactive oxygen species (ROS) and a rheology modifier. Also presented herein is a process for making the gels which includes making the composition by taking the steps of purifying water to produce ultra-pure water, combining a salt to the ultra-pure water to create a salinated water, electrolyzing the salinated water at a temperature of 4.3 to 5.8° C. such that the electrolyzing is accomplished with an anode, cathode and power source such that the power source comprises a transformer and a rectifier and does not comprise a filter capacitor.

18 Claims, 24 Drawing Sheets

(56) References Cited

U.S. PATENT DOCUMENTS

| | | | |
|---|---|---|---|
| 9,833,406 B1 | 12/2017 | Richards | |
| 9,962,404 B2 | 5/2018 | Robinson et al. | |
| 2002/0114849 A1 | 8/2002 | Camper et al. | |
| 2002/0160053 A1* | 10/2002 | Yahagi | A61K 33/20 424/600 |
| 2002/0168387 A1 | 11/2002 | Young | |
| 2003/0185704 A1* | 10/2003 | Bernard | A01N 59/00 422/37 |
| 2004/0044220 A1 | 3/2004 | Bergeron, Jr. | |
| 2005/0089537 A1 | 4/2005 | Birnholz | |
| 2005/0196462 A1 | 9/2005 | Alimi | |
| 2006/0235350 A1 | 10/2006 | Alimi et al. | |
| 2006/0241546 A1 | 10/2006 | Alimi | |
| 2007/0021213 A1 | 1/2007 | Foe | |
| 2007/0172412 A1 | 7/2007 | Hratko et al. | |
| 2007/0261950 A1 | 11/2007 | Sato et al. | |
| 2007/0281008 A1 | 12/2007 | Lin et al. | |
| 2008/0003171 A1 | 1/2008 | Smith et al. | |
| 2008/0008621 A1 | 1/2008 | Masahiro et al. | |
| 2008/0160612 A1 | 7/2008 | Selkon | |
| 2009/0028811 A1 | 1/2009 | Potter | |
| 2009/0068122 A1 | 3/2009 | Shira et al. | |
| 2009/0148342 A1 | 6/2009 | Bromberg et al. | |
| 2009/0169646 A1 | 7/2009 | Bosch et al. | |
| 2009/0258083 A1 | 10/2009 | Calderon | |
| 2010/0012132 A1 | 1/2010 | Harrison et al. | |
| 2010/0078331 A1 | 4/2010 | Scherson | |
| 2010/0197748 A1 | 8/2010 | Schwarz et al. | |
| 2011/0052506 A1 | 3/2011 | Abel et al. | |
| 2011/0121110 A1 | 5/2011 | Field | |
| 2012/0046556 A1 | 2/2012 | Block | |
| 2012/0148516 A1 | 6/2012 | Abel | |
| 2012/0164235 A1 | 6/2012 | Northey | |
| 2013/0164228 A1 | 6/2013 | Stanislav et al. | |
| 2013/0168260 A1 | 7/2013 | Scherson et al. | |
| 2013/0236563 A1 | 9/2013 | Samuelson | |
| 2013/0243883 A1 | 9/2013 | Norton et al. | |
| 2013/0261534 A1* | 10/2013 | Niezgoda | A61M 1/0088 604/22 |
| 2014/0044800 A1 | 2/2014 | Robinson et al. | |
| 2014/0328946 A1 | 11/2014 | Northey | |
| 2014/0369953 A1 | 12/2014 | Purschwitz | |
| 2015/0017257 A1 | 1/2015 | Megumi et al. | |
| 2015/0093451 A1 | 4/2015 | Neiman | |
| 2015/0099010 A1 | 4/2015 | Hoover | |
| 2015/0118180 A1 | 4/2015 | Hoover | |
| 2015/0125543 A1 | 5/2015 | Croke et al. | |
| 2015/0246131 A1 | 9/2015 | Romanoschi et al. | |
| 2015/0250704 A1 | 9/2015 | Romanoschi et al. | |

FOREIGN PATENT DOCUMENTS

| | | |
|---|---|---|
| EP | 0335584 | 10/1989 |
| EP | 1886664 | 2/2008 |
| JP | 59-023888 | 2/1984 |
| JP | 08-010767 | 1/1996 |
| JP | 11-010153 | 1/1999 |
| JP | 2005-058848 | 3/2005 |
| JP | 2005-230280 | 9/2005 |
| JP | 2006-346203 | 12/2006 |
| WO | WO 9934773 | 7/1999 |
| WO | WO 2010004699 | 1/2010 |
| WO | WO 2011/014809 A1 | 2/2011 |
| WO | WO2011014809 * | 2/2011 |
| WO | WO 2015002932 | 3/2015 |
| WO | WO 2016100543 | 6/2016 |

OTHER PUBLICATIONS

Hayyan et al. Long term stability of superoxide ion in piperidinium, pyrrolidinium and phosphonium cations-based ionic liquids and its utilization in the destruction of chlorobenzenes. Journal of Electroanalytical Chemistry. vol. 664, 2012, 26-32.

Konaka et al. Irradiation of Titanium Dioxide Generates Both Singlet Oxygen and Superoxide Anion. Free Radical Biology & Medicine, vol. 27, Nos. 3/4, pp. 294-300, 1999.

Prasanth, "Antimicrobial Efficacy of Different Toothpastes and Mouthrinses: An In Vitro Study", Dent Res J (Isfahan), 2011 Spring, 8(2); 85-94.

"High purity, activated HClO Perfect Perio", http://amanodental.com/english/PerfectPerio-how-to-use.pdf, Nov. 2010.

Notice of Rejection in Japanese application No. 2016-522003, dated Sep. 4, 2018.

European Communication from the Examining Division, dated Oct. 18, 2017.

AlNashef et al., "Electrochemical Generation of Superoxide in Room-Termperature Ionic Liquids." *Electrochemical and Solid State Letters,* 4(11), pp. D16-D18, (2001).

AlNashef et al., "Superoxide Electrochemistry in an Ionic Liquid." *Industrial Engineering Chemistry Research* 2002, 41, 4475-4478.

Bielski et al., "Reactivity of HO2/O2-Radicals in Aqueous Solution." *Journal of Physical Chemical Reference Data,* vol. 14, No. 4, pp. 1041-1100, 1985.

Hayyan et al., "Generation and stability of superoxide ion in tris(pentafluoroethyl) triftuorophosphate anion-based ionic liquids." *Journal of Fluorine Chemistry,* vol. 142, Oct. 2012, pp. 83-89.

Hayyan et al., "Long term stability of superoxide ion in piperidinium, pyrrolidinium and phosphonium cations-based ionic liquids and its utilization in the destruction of chlorobenzenes." *Journal of Electroanalytical Chemistry,* vol. 664, Jan. 1, 2012, pp. 26-32.

Kahn et al., "Spin Traps: In Vitro Toxicity and Stability of Radical Adducts." *Free Radical Biology & Medicine,* vol. 34, No. 11, pp. 1473-1481, 2003.

Kariduraganavar et al., "Ion-exchange membranes: preparative methods for electrodialysis and fuel cell applications." *Desalination* 197 (2006) 225-246.

Konaka et al., "Irradiation of Titanium Dioxide Generates Both Singlet Oxygen and Superoxide Anion." *Free Radical Biology & Medicine,* vol. 27, Nos. 3/4, pp. 294-300, Feb. 23, 1999.

Zoulias et al., "A Review on Water Electrolysis." last modified Jan. 20, 2006 15:24.

\* cited by examiner

| Anode | | | Cathode | | | |
|---|---|---|---|---|---|---|
| + | | e−↑ | e−↓ | | | − |
| | | | | | | 1st Generation |
| −1.23 V: $O_2$ :$4H^+$ | 4e ↑ | $2H_2O$ | $2H^+$ | 2e ↓ | $H_2$ | :−0.00V |
| −0.40V: $O_2$ | 4e ↑ | $4OH^-$ | $2H_2O$ | 2e ↓ | $H_2$ $2OH^-$ | :−0.83V |
| −.89V: $ClO^-$ :$H_2O$ | 2e ↑ | $2OH^-$ $Cl^-$ | $2H_2O$ | 2e ↓ | $2H^+$ $H_2O_2$ | :1.76V |
| −1.36 V: $Cl_2$ | 2e ↑ | $2Cl^-$ | $Na^+$ | 1e ↓ | $Na_{(s)}$ | :−2.71V |
| | | | | | | 2nd Generation |
| −1.63V :2HClO :$2H^+$ | 2e ↑ | $Cl_2$ $2H_2O$ | $O_2$ | 1e ↓ | $O_2^{*-}$ | :−0.33V |
| −1.67V :$HClO_2$ :$2H^+$ | 2e ↑ | HClO $H_2O$ | $O_2$ $H^+$ | 1e ↓ | $HO_2^*$ | :−0.13V |
| −2.07V :$O_3$ :$2H^+$ | 2e ↑ | $O_2$ $H_2O$ | $O_2$ $H^+$ | 2e ↓ | $H_2O_2$ | :0.70V |
| −1.18V :$2ClO_3^-$ :$12H^+$ | 10e ↑ | $Cl_2$ $6H_2O$ | 2HClO $2H^+$ | 2e ↓ | $Cl_2$ $2H_2O$ | :1.63V |
| | | | | | | 3rd Generation+ |
| −1.19V :$ClO_2$ :$H^+$ | 1e ↑ | $HClO_2$ $H_2O$ | $HO_2^*$ | 1e ↓ | $H_2O_2$ | :1.51V |
| −1.18V :$ClO_3^-$ :$2H^+$ | 1e ↑ | $ClO_2$ $H_2O$ | $H_2$ | 2e ↓ | $2H^-$ | :−2.25V |

FIG. 2

FIG. 11
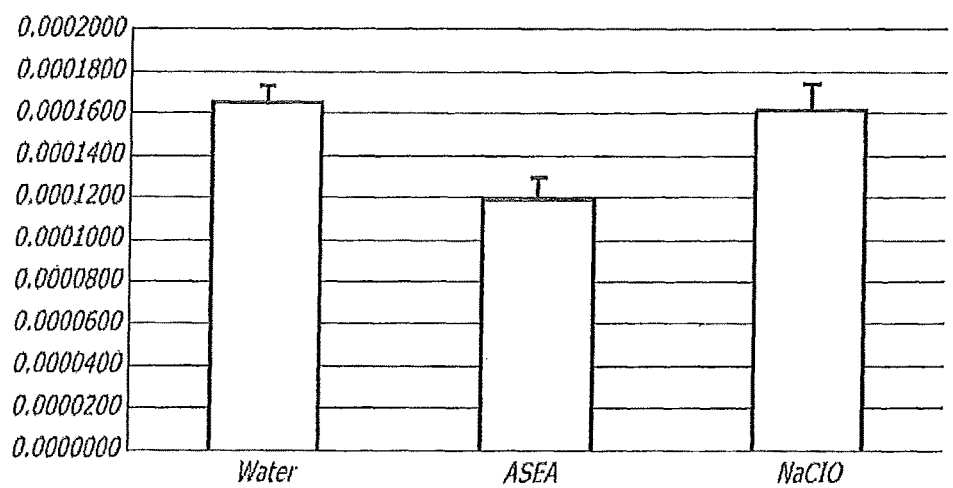
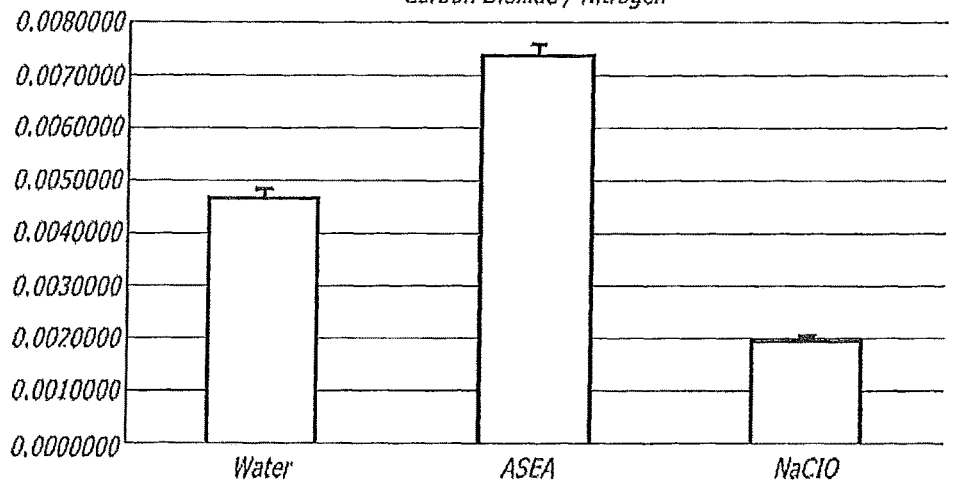
FIG. 12

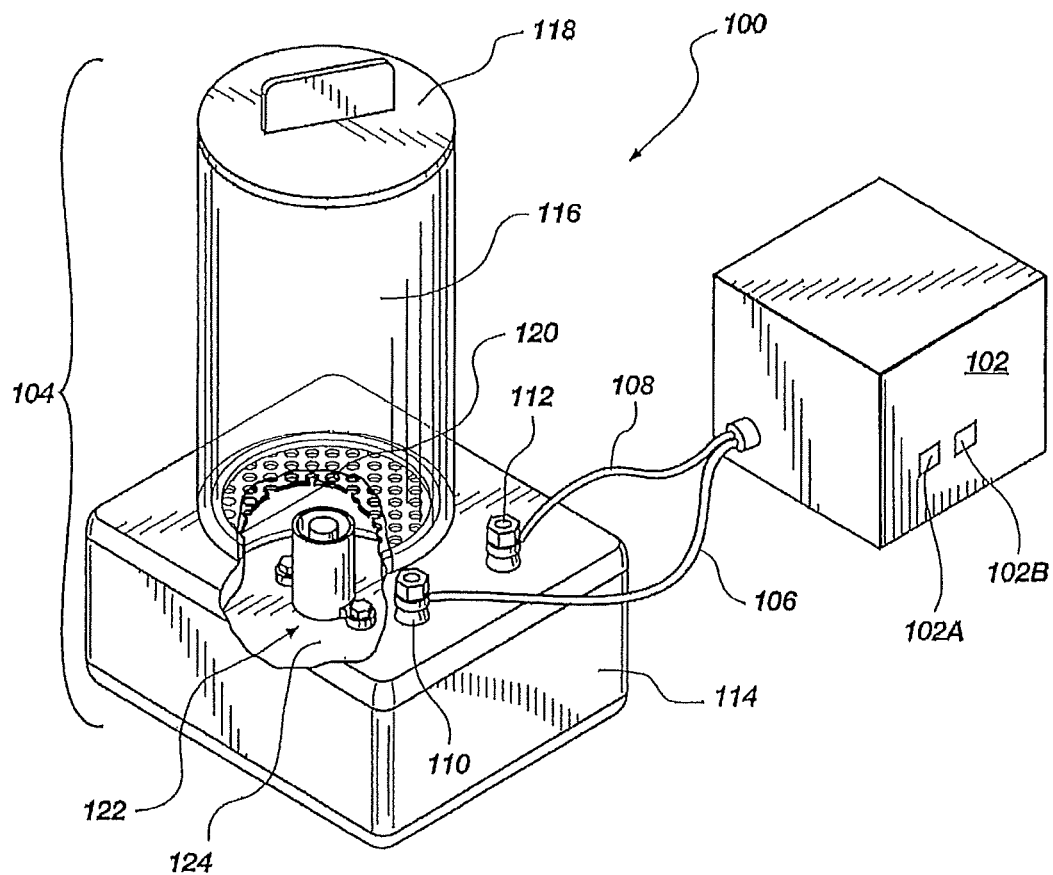
FIG 14
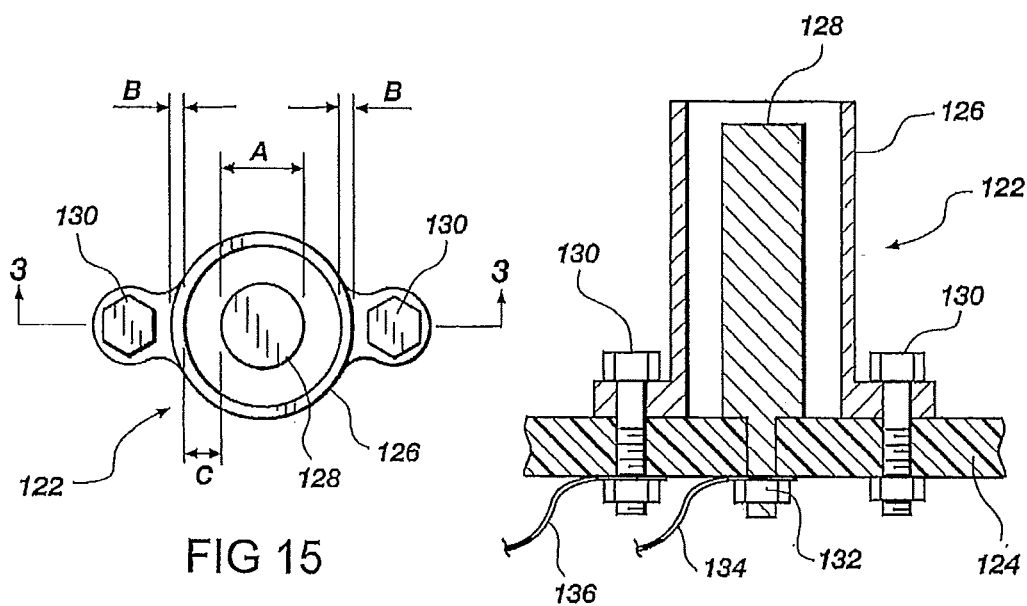
FIG 15
FIG 15a

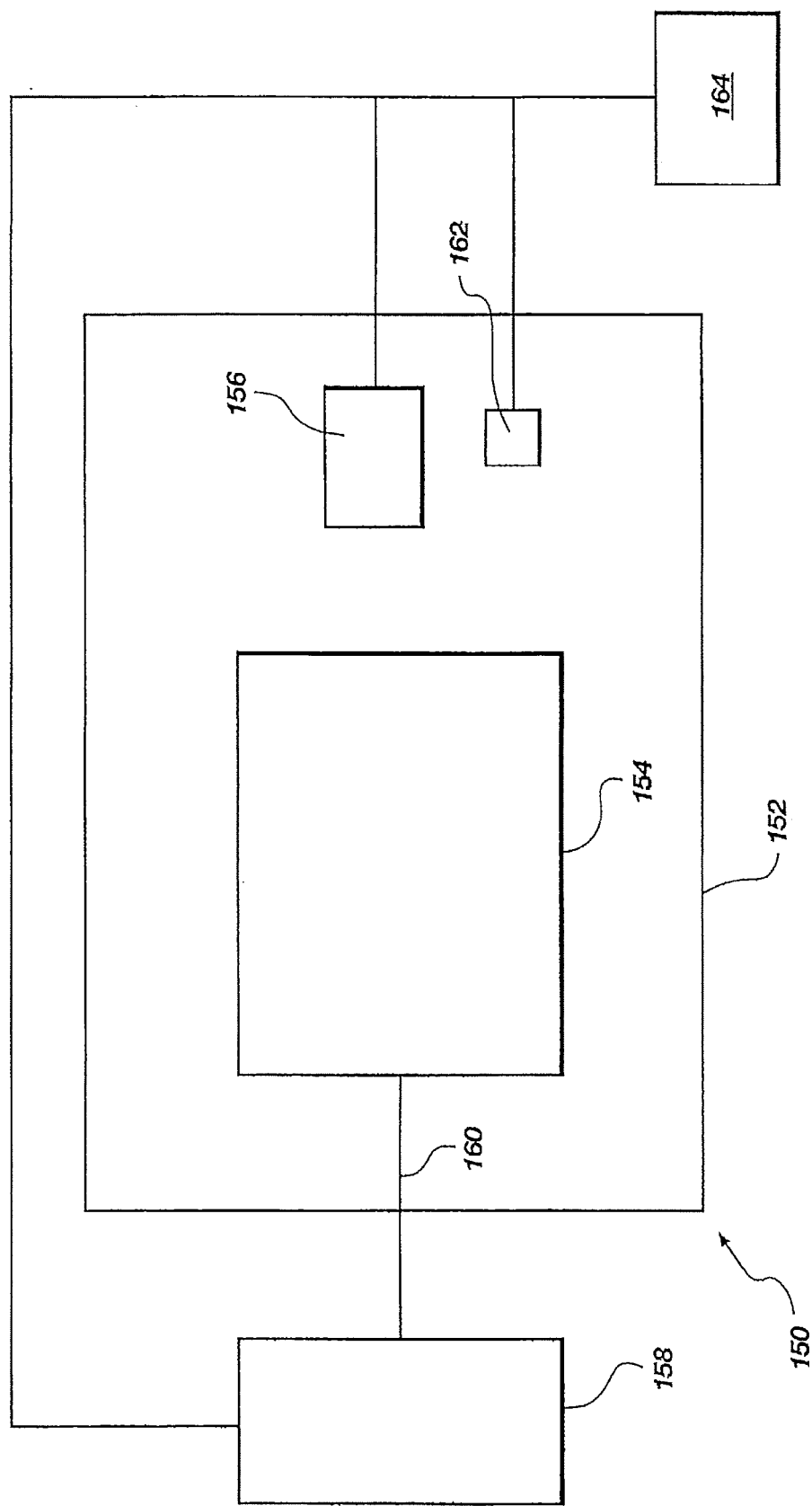

REDOX SIGNALING GEL FORMULATION

BACKGROUND OF THE INVENTION

Field of the Invention

The present invention relates generally to gels and methods of making gels.

Background

It has long been known that the electrolysis of fluids can result in useful products. Thus, various apparatus and methods have been proposed for electrolyzing saline solution, however, all of the previously available schemes present one or more drawbacks. Moreover, the industry has been struggling with a method to create a stabilized gel form of electrolyzed fluids.

For example U.S. Pat. No. 8,323,252 B2 to Alimi et al. teaches a gel formulation for the treatment of diabetic foot ulcer and is incorporated herein by reference in its entirety. Similarly, U.S. Patent Application No. 2012/0164235 A1 to Northey teaches a hydrogel comprising oxidative reductive potential water and is incorporated herein by reference in its entirety.

US Patent Publication No. 2011/0121110 A1 to Field is generally directed to an apparatus for making and discharging ORP water and is incorporated herein by reference in its entirety. The apparatus itself includes an electrode and a control circuit and a way to dispense of the ORP water.

U.S. Pat. No. 6,333,054 B1 to Rogozinski is generally directed to a gel made from an electrolytically derived hypochlorite solution and is incorporated herein by reference in its entirety. The gels that are used include Laponite.

US Patent Publication No. 2014/0044800 A1 to Robinson et al. is incorporated herein by reference in its entirety and is generally directed to electrolyzed water comprising reactive oxygen species.

For example U.S. Pat. No. 7,691,249 to Daly et al. teaches a method an apparatus for making electrolyzed water comprising an insulating end cap for a cylindrical electrolysis cell and is incorporated herein by reference in its entirety.

For example, U.S. Pat. Nos. 4,236,992 and 4,316,787 to Themy disclose an electrode, method and apparatus for electrolyzing dilute saline solutions to produce effective amounts of disinfecting agents such as chlorine, ozone and hydroxide ions. Both of these references are incorporated herein by reference in their entireties U.S. Pat. Nos. 5,674,537, 6,117,285 and 6,007,686 also teach electrolyzed fluids and are now incorporated herein by reference in their entireties.

U.S. Pat. No. 4,810,344 teaches a water electrolyzing apparatus including a plurality of electrolysis devices, each comprising an electrolysis vessel having a cathode and an anode oppose to each other and an electrolysis diaphragm partitioning the space between both of the electrodes wherein the plurality of devices are connected in a series such that only one of the two ionized water discharge channels of the devices constitutes a water supply channel to the device a the succeeding stage and is incorporated herein by reference in its entirety.

U.S. Pat. No. 7,691,249 is now incorporated herein by reference in its entirety and is directed to a method and apparatus for making electrolyzed water.

Methods for treatment of physiological fluids using electrolyzed solutions are set forth in U.S. Pat. No. 5,334,383 which is now incorporated herein by reference in its entirety teaches an electrolyzed saline solution, properly made and administered in vivo, as effective in the treatment of various infections brought on by invading antigens and particularly viral infections.

U.S. Pat. No. 5,507,932 which is now incorporated herein by reference in its entirety teaches an apparatus for electrolyzing fluids.

Described herein generally are aqueous formulations including at least one stable reactive and/or radical species.

U.S. Pat. No. 8,062,501 B2 is directed to a method for producing neutral electrolytic water containing OH, D2, HD and HDO as active elements and is incorporated herein by reference in its entirety.

There is a need for stabilized or contained superoxides, hydroxyl radicals and/or OOH* in an aqueous medium, without solvents or catalysts, outside the human body. The art teaches that superoxides, hydroxyl radicals and/or OOH* last for a very short amount of time. Even years after the priority date of this application, stabilizing superoxides in particular was proving difficult and inapplicable: Hayyan et al. Generation and stability of superoxide ion in tris(pentafluoroethyl) trifluorophosphate anion-based ionic liquids. Journal of Fluorine Chemistry. Volume 142, October 2012, Pages 83-89 and Hayyan et al. Long term stability of superoxide ion in piperidinium, pyrrolidinium and phosphonium cations-based ionic liquids and its utilization in the destruction of chlorobenzenes. Journal of Electroanalytical Chemistry. Volume 664, 1 Jan. 2012, Pages 26-32.

At the time the priority document was filed, superoxides were known to have a very short lifespan: Kahn et al. SPIN TRAPS: IN VITRO TOXICITY AND STABILITY OF RADICAL ADDUCTS. Free Radical Biology & Medicine, Vol. 34, No. 11, pp. 1473-1481, 2003, AlNashef et al. Electrochemical Generation of Superoxide In Room-Temperature Ionic Liquids. Electrochemical and Solid State Letters, 4 (11) D16-D18 (2001), AlNashef et al. Superoxide Electrochemistry in an Ionic Liquid. Ind. Eng. Chem. Res. 2002, 41, 4475-4478, Bielski et al. Reactivity of HO2/O2— Radicals in Aqueous Solution. J. Phys. Chem. Ref. Data, Vol. 14, No. 4 1985, Konaka et al. IRRADIATION OF TITANIUM DIOXIDE GENERATES BOTH SINGLET OXYGEN AND SUPEROXIDE ANION. Free Radical Biology & Medicine, Vol. 27, Nos. 3/4, pp. 294-300, 1999.

Typically, in the process of making electrolyzed water, membranes are considered required. Zhuang et al. Homogeneous blend membrane made from poly(ether sulphone) and poly(vinylpyrrolidone) and its application to water electrolysis. Journal of Membrane Science. Volume 300, Issues 1-2, 15 Aug. 2007, Pages 205-210, Sawada et al. Solid polymer electrolyte water electrolysis systems for hydrogen production based on our newly developed membranes, Part I: Analysis of voltage. Progress in Nuclear Energy, Volume 50, Issues 2-6, March-August 2008, Pages 443-448, Okada et al. Theory for water management in membranes for polymer electrolyte fuel cells: Part 1. The effect of impurity ions at the anode side on the membrane performances. Journal of Electroanalytical Chemistry Volume 465, Issue 1, 6 Apr. 1999, Pages 1-17, Okada et al. Theory for water management in membranes for polymer electrolyte fuel cells: Part 2. The effect of impurity ions at the cathode side on the membrane performances. Journal of Electroanalytical Chemistry, Volume 465, Issue 1, 6 Apr. 1999, Pages 18-29, Okada et al. Ion and water transport characteristics of Nafion membranes as electrolytes. Electrochimica Acta, Volume 43, Issue 24, 21 Aug. 1998, Pages 3741-3747, Zoulias et al. A Review on Water Electrolysis last modified 20 Jan. 2006 15:24, http://www.cres.gr/kape/publications/papers/dimosieyseis/ydrogen/

A%20REVIEW%20ON%20WATER%20-ELECTROLYSIS.pdf, Xu et al. Ion exchange membranes: state of their development and perspective. Journal of Membrane Science 263 (2005) 1-29, Kariduraganavar et al. Ion-exchange membranes: preparative methods for electrodialysis and fuel cell applications. Desalination 197 (2006) 225-246, Asawa et al. Material properties of cation exchange membranes for chloralkali electrolysis, water electrolysis and fuel cells. Journal of Applied Electrochemistry. July 1989, Volume 19, Issue 4, pp 566-570. However, the inventive product and process described herein is done without a separator or separating membrane/diaphragm.

Products comprising electrolyzed water and in particular, gel products, have been known to be unstable and unable to maintain a long shelf-life. This lack of stability effects the products functionality and benefits.

BRIEF SUMMARY OF THE INVENTION

The invention comprises a gel comprising reactive oxygen species. The inventive composition addresses and cures the problem of manufacturing a gel product with electrolyzed water that has a long shelf-life. Further, the instant invention teaches how to make a gel that maintains its stability and redox signaling functionality. The gel of the instant invention maintains its benefits as a cosmetic and topical pharmaceutical even after shipping and storage.

Reactive oxygen species (ROS) are of immense interest in medicine because there is compelling evidence linking them to aging, disease processes and the reduction of oxidative stress. Further, they are employed as microbicidal agents in the home, hospital and other settings. ROS include superoxides. There is a need in the art for a safe, effective, economical way of producing superoxides and employing them in the medical industries. Described herein is a product and a process for making products which contain these and other radicals and methods of using these ROS and other radicals in gel formulations.

Redox signaling deals with the action of a set of several simple reactive signaling molecules that are mostly produced by the mitochondria residing inside cells during the metabolism of sugars. These reactive signaling molecules are categorized into two general groups, Reactive Oxygen Species (ROS), which contain oxidants, and Reduced Species (RS), which contain reductants. These fundamental universal signaling molecules in the body are the simple but extremely important reactive signaling molecules that are formed from combinations of the atoms (Na, Cl, H, O, N) that are readily found in the saline bath that fills the inside of the cells (cytosol). All of the molecular mechanisms inside healthy cells float around in this saline bath and are surrounded by a balanced mixture of such reactive signaling molecules. A few examples of the more than 20 reactive molecules formed from these atoms inside the cell, some of which are discussed herein, are superoxide, hydrogen peroxide, hypochlorous acid and nitric oxide.

Such reactive signaling molecules are chemically broken down by specialized enzymes placed at strategic locations inside the cell. Some of these protective enzymes are classified as antioxidants such as Glutathione Peroxidase and Superoxide Dismutase. In a healthy cell, the mixtures of these reactive signaling molecules are broken down by the antioxidant enzymes at the same rate that they are produced by the mitochondria. As long as this homeostatic balance is maintained, the cell's chemistry is in balance and all is well.

When damage occurs to the cell, for any number of reasons, including bacterial or viral invasion, DNA damage, physical damage or toxins, this homeostatic balance is disturbed and a build-up of oxidants or reductants occurs in the cell. This condition is known as oxidative stress and it acts as a clear signal to the cell that something is wrong. The cell reacts to this signal by producing the enzymes and repair molecules necessary to attempt repairs to the damage and it also can send messengers to activate the immune system to identify and eliminate threats. If oxidative stress persists in the cell for more than a few hours, then the cell's repair attempts are considered unsuccessful and the cell kills and dismantles itself and is replaced by the natural cellular division of healthy neighboring cells.

On a cellular level, this is essentially the healthy tissue maintenance process: damaged cells are detected and repaired or replaced by healthy cells. This cellular repair and regeneration process is constantly taking place, millions of times an hour, in all parts of the body.

In one embodiment, the invention is directed to a gel formulation comprising;
a. a composition comprising at least one reactive oxygen species (ROS), and
b. a rheology modifier;
wherein the process of making the composition comprises the steps of purifying water to produce ultra-pure water, combining a salt to the ultra-pure water to create a salinated water, electrolyzing the salinated water at a temperature of 4.3 to 5.8° C. wherein the electrolyzing is accomplished with an anode, cathode and power source such that a) the power source comprises a transformer and a rectifier and does not comprise a filter capacitor and b) no membrane is used between the anode and cathode during the process of electrolyzing.

In another embodiment, the invention is directed to a gel formulation wherein the at least one reactive oxygen species (ROS) is a superoxide.

In another embodiment, the invention is directed to a gel formulation wherein the at least one reactive oxygen species (ROS) is hypochlorous acid or a salt thereof.

In another embodiment, the invention is directed to a gel formulation wherein the at least one reactive oxygen species (ROS) is present at an amount of at least 25% of its original concentration after 1 year.

In a further embodiment, the invention is directed to a gel formulation wherein the process is a scaled up process.

In a further embodiment, the invention is directed to a gel formulation wherein the salt is sodium chloride.

In yet a further embodiment, the invention is directed to a gel formulation wherein the process includes a pulsating voltage such that the voltage is 0 at least 30 times per second and the voltage remains positive at all times.

In yet a further embodiment, the invention is directed to a gel formulation wherein the gel has a pH between 6 and 9.

In yet a further embodiment, the invention is directed to a gel formulation wherein the composition comprises:
a. sodium present at a concentration of 1000 to 1400 ppm wherein the sodium is measured by inductively coupled plasma mass spectrometry (ICP-MS),
b. chloride present at a concentration from 1200 to 1600 ppm as wherein the chloride is measured by inductively coupled plasma mass spectrometry (ICP-MS) or chloride is present at a concentration from 0 to 1 ppm wherein the chloride is measured by 35Cl nuclear magnetic resonance (35Cl NMR),
c. hypochlorous acid present at a concentration of 16 to 24 ppm wherein the hypochlorous acid is measured by colorimetry or hypochlorous acid present at a concentration of 2300 to 2700 ppm wherein the hypochlorous acid is measured by 25Cl nuclear magnetic resonance (25Cl NMR), d. superoxide radical present at a concentration of 94 uM wherein the superoxide radical is measured by 5-(Diisopropoxyphosphoryl)-5-1-pyrroline-N-oxide nuclear magnetic resonance (DIPPMPO-NMR) or no superoxide radical, and e. hydroxyl radical present at a concentration of 241 uM wherein the hydroxyl xeradical is measured by DIPPMPO-NMR or hydroxyl radical present at a concentration of 0 to 10 ppm wherein the hydroxyl radical is measured by mass spectrometry (MS) or no hydroxyl radical.

In one embodiment, the invention is directed to a gel formulation wherein the sodium, chloride, hypochlorous acid, superoxide radical and hydroxyl radical are measured less than one year after the composition was made.

In one embodiment, the invention is directed to a gel formulation wherein the sodium, chloride, hypochlorous acid, superoxide radical and hydroxyl radical are present at any time within 1 year after the composition was made.

In one embodiment, the invention is directed to a gel formulation wherein the sodium, chloride, hypochlorous acid, superoxide and hydroxyl radical are measured at different times.

In one embodiment, the invention is directed to a gel formulation wherein the sodium, chloride, hypochlorous acid, superoxide radical and hydroxyl radical are measured at the same time.

In one embodiment, the invention is directed to a gel formulation wherein the rheology modifier comprises $SiO_2$, MgO, $Li_2O$, and $Na_2O$.

In one embodiment, the invention is directed to a gel formulation wherein the rheology modifier comprises a crosslinked acrylic acid polymer.

In one embodiment, the invention is directed to a gel formulation wherein the composition has an electron paramagnetic resonance (EPR) spectrum as shown in FIG. 13.

BRIEF DESCRIPTION OF THE DRAWINGS

FIG. 2 illustrates an example diagram of the generation of various molecules at the electrodes. The molecules written between the electrodes depict the initial reactants and those on the outside of the electrodes depict the molecules/ions produced at the electrodes and their electrode potentials.

FIG. 11 illustrates ozone/nitrogen ratios for a composition described herein compared to water and NaClO (the composition is labeled "ASEA").

FIG. 12 illustrates the carbon dioxide to nitrogen ratio of a composition as described herein compared to water and NaClO (the composition is labeled "ASEA").

FIG. 14 is a perspective view of a first presently preferred embodiment of an apparatus for making the present invention.

FIG. 15 is a detailed top view of the electrode assembly represented in FIG. 14.

FIG. 15A is a side cross sectional view of the electrode assembly represented in FIG. 15 taken along line 3-3 in FIG. 15.

FIG. 16 is a block diagram of a second presently preferred embodiment of an apparatus for making the present invention.

DETAILED DESCRIPTION OF THE INVENTION

Figure 1:
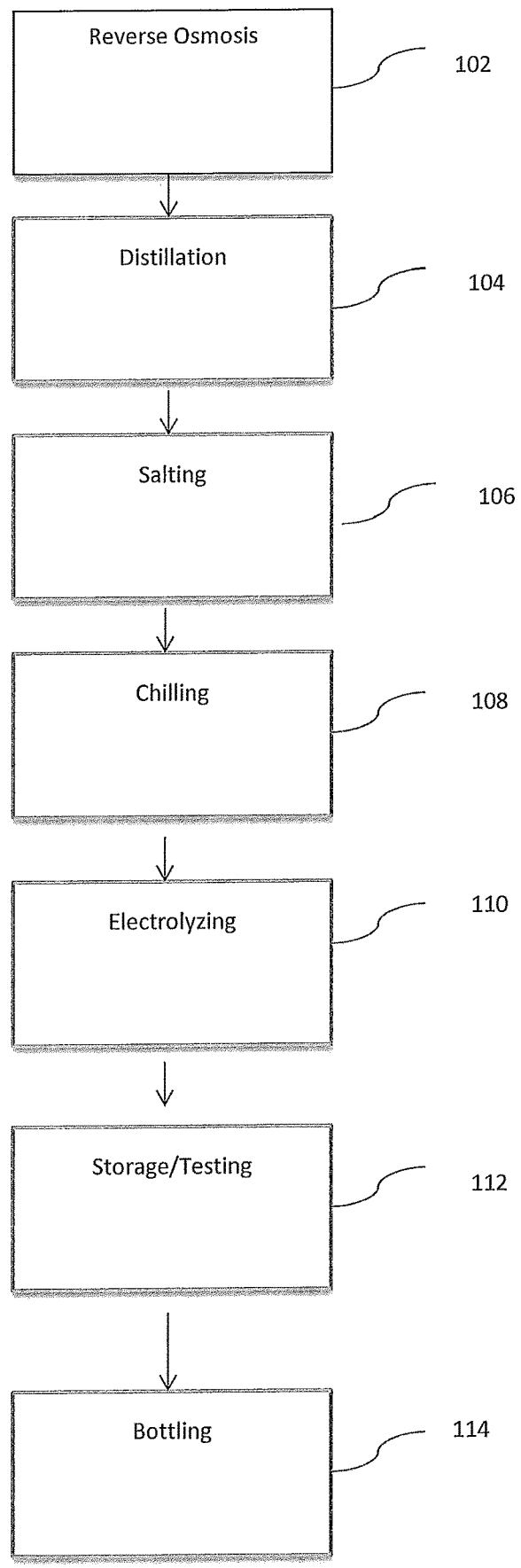
FIG. 1 is a flow chart of a process as described herein.

Described herein are formulations including gels or hydrogels that generally include at least one redox signaling agent (RXN). RXNs can include, but are not limited to superoxides: $O_2^{*-}$, $HO_2^*$; hypochlorites: $OCl^-$, HOCl, NaOCl; hypochlorates: $HClO_2$, $ClO_2$, $HClO_3$, $HClO_4$; oxygen derivatives: $O_2$, $O_3$, $O_4^{*-}$, $1O$; hydrogen derivatives: $H_2$, $H^-$; hydrogen peroxide: $H_2O_2$; hydroxyl free radical: $OH^{*-}$; ionic compounds: $Na^+$, $Cl^-$, $H^+$, $OH^-$, NaCl, HCl, NaOH; chlorine: $Cl_2$; water clusters: $n*H_2O$—induced dipolar layers around ions and combinations thereof. Some RXNs are electron acceptors and some are electron donors.

Gels and hydrogels can be made from ingredients including aqueous ingredients and rheology modifiers. Rheology is the study of the flow of matter, or fluids such as Newtonian fluids, but also as 'soft solids' or solids under conditions in which they respond with plastic flow rather than deforming elastically in response to an applied force (http://en.wikipedia.org/wiki/Rheology Retrieved 17 Oct. 2013). Rheology modifiers are used in the cosmetic industry to affect the look and feel of cosmetics as well as to impart beneficial properties on these cosmetics. Rheology modifiers can be used as desired by the end user and can be chosen based on their desired characteristics and compatibility with the redox signaling composition.

Rheology modifiers, also called thickening agents, viscosity modifiers or gelling agents, can be acrylic acid-based polymers, which can include high molecular weight, crosslinked, acrylic acid-based polymers, e.g., having the following general structure:

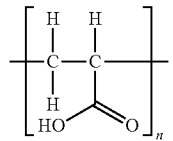

Such polymers are sold under the tradename Carbopol®. Carbopol® polymers are generally supplied as rheology modifiers for use thickeners, suspending agents, and stabilizers in a variety of personal care products, pharmaceuticals, and household cleaners. Carbopol® polymers may be used in either solid (e.g., powder) or liquid form.

The acrylic acid-based polymers suitable for use in the invention may be homopolymers or copolymers. Suitable homopolymers may be crosslinked, preferably with allyl sucrose or allylpentaerythritol. Suitable copolymers of acrylic acid can be modified by long chain (C10-C30) alkyl acrylates and can be crosslinked, e.g., with allylpentaerythritol. Carbopol® polymers are preferably neutralized in order to achieve maximum viscosity. As supplied, Carbopol® polymers can exist as dry, tightly coiled acidic molecules, held in a coiled structure by hydrogen bonds. Once dispersed in water, or another solvent, such polymer can begin to hydrate and partially uncoil. One way to achieve maximum thickening from Carbopol® polymers is by converting the acidic polymer into a salt. This is easily achieved by neutralizing with a common base such as sodium hydroxide (NaOH) or triethanolamine (TEA) to "uncoil" the long chain polymer and provide an effective thickening form. Additional neutralizers include Sodium hydroxide, ammonium hydroxide, potassium hydroxide, arginine, aminomethyl propanol, tetrahydroxypropyl ethylenediamine, triethanolamine, tromethamine, PEG-15 Cocamine, diisopropanolamine and triisopropanolamine.

The amount of neutralizing agent will depend on the desired characteristics of the gel/hydrogel product and will depend on the type of neutralizing agent. For example, the amount of neutralizing agent can be described as a ratio of neutralizer to Carbopol® (Base:Carbopol®) and can be present in an ratio of from 0.1:1 to 10:1. Preferably, the neutralizer is present in an amount of 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or 10 parts neutraliser to 1 part Carbopol®. More preferably, the neutralizing agent is NaOH and is present in a ratio of 2.3:1 (neutralizer:Carbopol®). These amounts can be approximate and can be modified to achieve specific characteristics desired or required in the composition.

Suitable thickening agents preferably will yield the desired viscosity for the formulation, as well as other characteristics, such as appearance, shear resistance, ion resistance, and thermal stability. For example, Carbopol® 934 is preferred for a formulation that is either a suspension or emulsion (rather than a clear gel) with a viscosity greater than 3000 centipoise (cps). Carbopol® 974P may alternatively be used for its advantageous bioadhesive properties.

A preferable Carbopol® is Carbopol® Ultrez 30.

Other rheology modifiers include any suitable metal silicate gelling agent and may be used in the hydrogel formulation of the present invention. Typically, a metal silicate gelling agent is used, wherein the metal is an alkali metal, an alkaline earth metal, or a combination thereof. Suitable alkali metals or alkaline earth metals include, but are not limited to, lithium, sodium, potassium, magnesium, calcium, and the like. In a preferred embodiment, the metal silicate gelling agent is a sodium magnesium silicate or a derivative thereof. In a most preferred embodiment, the metal silicate gelling agent is sodium magnesium fluorosilicate.

Rheology modifiers can be present in the inventive hydrogel formulation in any suitable amount. Generally, the amount of modifier is from about 0.1% by weight to about 10% by weight, based on the weight of the formulation. Preferably, the amount of modifier is from about 1.0% to about 5% by weight. More preferably, the amount of modifier is 0.1%, 0.2%, 0.3%, 0.4%, 0.5%, 0.6%, 0.70%, 0.80%, 0.9%, 10%, 1.10%, 1.2%, 1.3%, 1.4%, 1.5%, 1.6%, 1.70%, 1.80%, 1.9%, 2%, 2.10%, 2.2%, 2.3%, 2.4%, 2.5%, 2.6%, 2.70%, 2.80/0, 2.9%, 3%, 3.10%, 3.2%, 3.3%, 3.4%, 3.5%, 3.6%, 3.70%, 3.80%, 3.9%, 4%, 4.10%, 4.2%, 4.3%, 4.4%, 4.5%, 4.6%, 4.7%, 4.8%, 4.9%, or 5% by weight. Most preferably, the amount of modifier is 1% or 2% by weight. These weight percentages can be approximate and can be modified to achieve specific characteristics desired or required in the composition.

The hydrogel formulation of the present invention may optionally include a buffering agent. Any suitable buffering agent may be employed to yield and maintain the desired pH of the formulation. Buffers suitable for use in the hydrogel formulations described herein include, but are not limited to, salts and acids of acetate, glutamate, citrate, tartrate, benzoate, lactate, histidine or other amino acids, gluconate, phosphate, malate, succinate, formate, propionate, and carbonate. Other buffering agents are generally known in the art (see, e.g., Handbook of Cosmetic and Personal Care Additives, 2nd ed., Ashe et al. eds. (2002), and Handbook of Pharmaceutical Excipients, 4th ed., Rowe et al. eds. (2003)). Suitable buffering agents may be either in liquid or solid form. In a preferred embodiment, the buffering agent is an acid or salt of a phosphate compound. In a more preferred embodiment, the buffering agent is sodium phosphate. The sodium phosphate employed herein can be any suitable form of sodium phosphate including, for example, monobasic sodium phosphate, dibasic sodium phosphate, disodium phosphate or combinations thereof. A preferred phosphate can be tetrasodium pyrophosphate.

When present, any suitable amount of buffering agent may be included in the formulation of the invention. Generally, the amount of buffering agent present in the inventive hydrogel formulations is from about 0.01 weight-percent to about 5.0 weight-percent, based on the weight of the formulation. Preferably, the buffering agent is present in an amount of from about 0.1 weight-percent to about 1.0 weight-percent.

The hydrogel formulations may further contain additional components such as colorants, fragrances, buffers, physiologically acceptable carriers and/or excipients, and the like. Examples of suitable colorants include, but are not limited to, titanium dioxide, iron oxides, carbazole violet, chromium-cobalt-aluminum oxide, 4-Bis[(2-hydroxyethyl) amino]-9,10-anthracenedione bis(2-propenoic)ester copolymers, and the like. Any suitable fragrance can be used.

The pH of the hydrogel formulation of the present invention is generally from about 3 to about 9. Typically, the pH of the hydrogel formulation is from 5.0 to 7.0. Preferably, the pH of the hydrogel formulation is from 5.6 to 7.0.

The viscosity of the hydrogel formulation can be any suitable viscosity such that the formulation can be topically administered to a patient. In one embodiment, the viscosity of the hydrogel formulation is in the range of about 1,000 to about 100,000 centipoise (cP). More particularly, the viscosity of the hydrogel is 1,000 cP, 2,000 cP, 3,000 cP, 4,000 cP, 5,000 cP, 10,000 cP, 15,000 cP, 20,000 cP, 25,000 cP, 30,000 cP, 35,000 cP, 40,000 cP, 45,000 cP, 50,000 cP, 55,000 cP, 60,000 cP, 65,000 cP, 70,000 cP, 75,000 cP, 80,000 cP, 85,000 cP, 90,000 cP, or 95,000 cP. Preferably, the viscosity of the hydrogel is in the range of about 1,000 cP to about 20,000 cP. More preferably, the viscosity of the hydrogel is in the range of about 12,000 cP to about 20,000 cP. These viscosity ranges can be approximate and can be modified to achieve specific characteristics desired or required in the composition.

The hydrogel is made with a composition. The gel or hydrogel comprises a composition and a rheology modifier. The composition may be a redox signaling composition and can be produced as described herein. Methods of producing these disclosed compositions can include one or more of the steps of (1) preparation of an ultra-pure solution of sodium chloride in water, (2) temperature control and flow regulation through a set of inert catalytic electrodes and (3) a modulated electrolytic process that results in the formation of such stable molecular moieties and complexes; the RS and ROS. In one embodiment, such a process includes all these steps.

A general example of one such method of making redox signaling compositions is described as comprising: electrolyzing salinated water having a salt concentration of about 2.8 g NaCl/L, using a set of electrodes with an amperage of about 3 amps, to form composition, wherein the water is at or below room temperature during 3 minutes of electrolyzing.

Another general example of one such method of making therapeutic compositions is described as comprising: electrolyzing salinated water having a salt concentration of about 9.1 g NaCl/L, using a set of electrodes with an amperage of about 3 amps, to form a composition, wherein the water is at or below room temperature during 3 minutes of electrolyzing.

The weight percentage of the redox signaling composition in the inventive gel can be from 50 wt % to 99.9 wt %. More preferably, the weight percentage of the redox signaling composition is present from 90 to 99.1% by weight or from 95 to 99.1%. More preferably, the amount of redox signaling composition is present at 95.1%, 95.2%, 95.3%, 95.4%, 95.5%, 95.6%, 95.7%, 95.8%, 95.9%, 96%, 96.1%, 96.2%, 96.3%, 96.4%, 96.5%, 96.6%, 96.7%, 96.8%, 96.9%, 97%, 97.1%, 97.2%, 97.3%, 97.4%, 97.5%, 97.6%, 97.7%, 95.8%, 97.9%, 98%, 98.1%, 98.2%, 98.3%, 98.4%, 98.5%, 98.6%, 98.7%, 98.8%, 98.9%, 99%, 99.1%, 99.2%, 99.3%, 99.4%, 99.5%, 99.6%, 99.7%, 99.8%, 99.9%, Most preferably, the amount of the redox signaling composition is 98% or 99% by weight. These weight percentages can be approximate and can be modified to achieve specific characteristics desired or required in the composition.

Water can be supplied from a variety of sources, including but not limited to municipal water, filtered water, nanopure water, or the like. With this in mind, a step in such a process is shown in FIG. 1 wherein the optional reverse osmosis procedure is shown as 102.

In one embodiment, contaminants can be removed from a commercial source of water by the following procedure: water flows through an activated carbon filter to remove the aromatic and volatile contaminants and then undergoes Reverse Osmosis (RO) filtration to remove dissolved solids and most organic and inorganic contaminants. The resulting filtered RO water can contain less than about 8 ppm of dissolved solids. Most of the remaining contaminants can be removed through a distillation process, resulting in dissolved solid measurements less than 1 ppm. In addition to removing contaminants, distillation may also serve to condition the water with the correct structure and Oxidation Reduction Potential (ORP) to facilitate the oxidative and reductive reaction potentials on the platinum electrodes in the subsequent electro-catalytic process.

Ultra-pure refers to the water which has a total dissolved solids count of less than 10 ppm. The total dissolved solids count of less than 10 ppm can be a result of reverse osmosis and/or distillation. Other known processes for water purification can also be used to reduce the amount of total dissolved solids.

The reverse osmosis process can vary, but can provide water having a total dissolved solids content of less than about 10 ppm, about 9 ppm, about 8 ppm, about 7 ppm, about 6 ppm, about 5 ppm, about 4 ppm, about 3 ppm, about 2 ppm, about 1 ppm, or the like.

The reverse osmosis process can be performed at a temperature of about 5° C., about 10° C., about 15° C., about 20° C., about 25° C., about 30° C., about 35° C., or the like. The reverse osmosis step can be repeated as needed to achieve a particular total dissolved solids level. Whether the optional reverse osmosis step is utilized, an optional distillation step 104 can be performed.

Other means of reducing contaminants include filtration and/or purification such as by utilizing deionization, carbon filtration, double-distillation, electrodeionization, resin filtration such as with Milli-Q purification, microfiltration, ultrafiltration, ultraviolet oxidation, electrodialysis, or combinations thereof.

The distillation process can vary, but can provide water having a total dissolved solids content of less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like. The temperature of the distillation process can be performed at a temperature of about 5° C., about 10° C., about 15° C., about 20° C., about 25° C., about 30° C., about 35° C., or the like.

The distillation step can be repeated as needed to achieve a particular total dissolved solids level. After water has been subjected to reverse osmosis, distillation, both, or neither, the level of total dissolved solids in the water can be less than about 5 ppm, about 4 ppm, about 3 ppm, about 2 ppm, about 1 ppm, about 0.9 ppm, about 0.8 ppm, about 0.7 ppm, about 0.6 ppm, about 0.5 ppm, about 0.4 ppm, about 0.3 ppm, about 0.2 ppm, about 0.1 ppm, or the like.

The reverse osmosis, distillation, both, or neither, can be preceded by a carbon filtration step. Purified water can be used directly with the systems and methods described herein.

After water has been subjected to reverse osmosis, distillation, both or neither, or any other purification step as described herein, a salt is added to the water in a salting step 106 of FIG. 1. The salt can be unrefined, refined, caked, de-caked, or the like. In one embodiment, the salt is sodium chloride (NaCl). In some embodiments, the salt can include an additive. Salt additives can include, but are not limited to potassium iodide, sodium iodidie, sodium iodate, dextrose, sodium fluoride, sodium ferrocyanide, tricalcium phosphate, calcium carbonate, magnesium carbonate, fatty acids, magnesium oxide, silicone dioxide, calcium silicate, sodium aluminosilicate, calcium aluminosilicate, ferrous fumarate, iron, or folic acid. Any of these additives can be added at this point or at any point during the described process. For example, the above additives can be added just prior to bottling.

The saline generally should be free from contaminants, both organic and inorganic, and homogeneous down to the molecular level. In particular, metal ions can interfere with the electro-catalytic surface reactions, and thus it may be helpful for metals to be avoided. In one embodiment, a brine solution is used to salinate the water. The brine solution can have a NaCl concentration of about 540 g NaCl/gal, such as 537.5 g NaCl/gal.

In another embodiment, the process can be applied to any ionic, soluble salt mixture, especially with those containing chlorides. In addition to NaCl, other non-limiting examples include LiCl, HCl, $CuCl_2$, $CuSO_4$, KCl, MgCl, $CaCl_2$, sulfates and phosphates. For example, strong acids such as sulfuric acid ($H_2SO_4$), and strong bases such as potassium hydroxide (KOH), and sodium hydroxide (NaOH) are frequently used as electrolytes due to their strong conducting abilities. Preferably the salt is sodium chloride (NaCl). A brine solution can be used to introduce the salt into the water. The amount of brine or salt needs will be apparent to one of ordinary skill in the art.

Salt can be added to water in the form of a brine solution. To mix the brine solution, a physical mixing apparatus can be used or a circulation or recirculation can be used. In one embodiment, pure pharmaceutical grade sodium chloride is dissolved in the prepared distilled water to form a 15 wt % sub-saturated brine solution and continuously re-circulated and filtered until the salt has completely dissolved and all particles >0.1 microns are removed. This step can take several days. The filtered, dissolved brine solution is then injected into tanks of distilled water in about a 1:352 ratio (salt:water) in order to form a 0.3% saline solution. In one embodiment, a ratio 10.75 g of salt per 1 gallon of water can be used to form the composition. In another embodiment, 10.75 g of salt in about 3-4 g of water, such as 3,787.5 g of water can be used to form the composition. This solution then can be allowed to re-circulate and diffuse until homogeneity at the molecular scale has been achieved. The brine solution can have a NaCl concentration of about 540 g NaCl/gal, such as 537.5 g NaCl/gal.

Brine can then be added to the previously treated water or to fresh untreated water to achieve a NaCl concentration of between about 1 g NaCl/gal water and about 25 g NaCl/gal water, between about 8 g NaCl/gal water and about 12 g NaCl/gal water, or between about 4 g NaCl/gal water and about 16 g NaCl/gal water. In a preferred example, the achieved NaCl concentration is 2.8 g/L of water. In another preferred example, the achieved NaCl concentration is 9.1 g/L of water. Once brine is added to water at an appropriate amount, the solution can be thoroughly mixed. The temperature of the liquid during mixing can be at room temperature or controlled to a desired temperature or temperature range.

To mix the solution, a physical mixing apparatus can be used or a circulation or recirculation can be used. The salt solution can then be chilled in a chilling step 108 of FIG. 1.

For large amounts of composition, various chilling and cooling methods can be employed. For example cryogenic cooling using liquid nitrogen cooling lines can be used. Likewise, the solution can be run through propylene glycol heat exchangers to achieve the desired temperature. A preferred method of chilling can be done by having the electrolysis process done in a walk in freezer. The chilling time can vary depending on the amount of liquid, the starting temperature and the desired chilled temperature.

Products from the anodic reactions can be effectively transported to the cathode to provide the reactants necessary to form the stable complexes on the cathode surfaces. Maintaining a high degree of homogeneity in the fluids circulated between the catalytic surfaces can also be helpful. A constant flow of about 2-8 mL/cm2 per sec can be used, with typical mesh electrode distances 2 cm apart in large tanks. This flow can be maintained, in part, by the convective flow of gasses released from the electrodes during electrolysis.

The mixed solution, chilled or not, can then undergo electrochemical processing through the use of at least one electrode in an electrolyzing step 110 of FIG. 1. Each electrode can be or include a conductive metal. Metals can include, but are not limited to copper, aluminum, titanium, rhodium, platinum, silver, gold, iron, a combination thereof or an alloy such as steel or brass. The electrode can be coated or plated with a different metal such as, but not limited to aluminum, gold, platinum or silver. In an embodiment, each electrode is formed of titanium and plated with platinum. The platinum surfaces on the electrodes by themselves can be optimal to catalyze the required reactions. Rough, double layered platinum plating can assure that local "reaction centers" (sharply pointed extrusions) are active and that the reactants not make contact with the underlying electrode titanium substrate.

In one embodiment, rough platinum-plated mesh electrodes in a vertical, coaxial, cylindrical geometry can be optimal, with, for example, not more than 2.5 cm, not more than 5 cm, not more than 10 cm, not more than 20 cm, or not more than 50 cm separation between the anode and cathode. The amperage run through each electrode can be between about 2 amps and about 15 amps, between about 4 amps and about 14 amps, at least about 2 amps, at least about 4 amps, at least about 6 amps, or any range created using any of these values. In one embodiment, 7 amps is used with each electrode. In one example, 1 amp is run through the electrodes. In one example, 2 amps are run through the electrodes. In one example, 3 amps are run through the electrodes. In one example, 4 amps are run through the electrodes. In one example, 5 amps are run through the electrodes. In one example, 6 amps are run through the electrodes. In one example, 7 amps are run through the electrodes. In a preferred example, 3 amps are run through the electrodes.

The amperage can be running through the electrodes for a sufficient time to electrolyze the saline solution. The solution can be chilled during the electrochemical process. The solution can also be mixed during the electrochemical process. This mixing can be performed to ensure substantially complete electrolysis.

Electric fields between the electrodes can cause movement of ions. Negative ions can move toward the anode and positive ions toward the cathode. This can enable exchange of reactants and products between the electrodes. In some embodiments, no barriers are needed between the electrodes.

After amperage has been run through the solution for a sufficient time, an electrolyzed solution is created. The solution can be stored and or tested for particular properties in storage/testing step 112 of FIG. 1. In one embodiment, the homogenous saline solution is chilled to about 4.8±0.5° C. Temperature regulation during the entire electro-catalytic process is typically required as thermal energy generated from the electrolysis process itself may cause heating. In one embodiment, process temperatures at the electrodes can be constantly cooled and maintained at about 4.8° C. throughout electrolysis.

The temperature of the solution at the time or duration of the electrolysis can be below 10° C. In a preferred embodiment, the temperature of the solution at the time or duration of the electrolysis is 10° C. or 9° C. or 8° C. or 7° C. or 6° C. or 5° C. or 4° C. or 3° C. or 2° C. or 1° C. or −1° C. or −2° C. or −3° C. or −4° C. or −5° C. or −6° C. or −7° C. or −8° C. or −9° C. or −10° C. The temperature can be within a range as well such as between 1 to 10° C. or, 3 to 7° C. or 4-6° C. Preferably the temperature during electrolysis is from 4 to 6° C. Most preferably, the temperature during electrolysis is from 4.5 to 5.8° C.

After amperage has been run through the solution for a sufficient time, an electrolyzed solution is created with beneficial properties, such as antifungal properties. The solution can have a pH of about 7.4. In some embodiments, the pH is greater than 7.3. In some embodiments, the pH is not acidic. In other embodiments, the solution can have a pH less than about 7.5. The pH may not be basic. The solution can be stored and or tested for particular properties in a storage/testing step 112 of FIG. 1.

The end products of this electrolytic process can react within the saline solution to produce many different chemical entities. The compositions and composition described herein can include one or more of these chemical entities, known as redox signaling agents or RXNs.

The chlorine concentration of the electrolyzed solution can be between about 5 ppm and about 34 ppm, between about 10 ppm and about 34 ppm, or between about 15 ppm and about 34 ppm. In one embodiment, the chlorine concentration is about 32 ppm.

The saline concentration in the electrolyzed solution can be, for example, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition can then be bottled in a bottling step 114 of FIG. 1. The composition can be bottled in plastic bottles having volumes of about 4 oz, about 8 oz, about 16 oz, about 32 oz, about 48 oz, about 64 oz, about 80 oz, about 96 oz, about 112 oz, about 128 oz, about 144 oz, about 160 oz, or any range created using any of these values. The plastic bottles can also be plastic squeezable pouches having similar volumes. In one embodiment, plastic squeezable pouches can have one way valves to prevent leakage of the composition, for example, during athletic activity.

During bottling, solution from an approved batch can be pumped through a 10 micron filter (e.g., polypropylene) to remove any larger particles from tanks, dust, hair, etc. that might have found their way into the batch. In other embodiments, this filter need not be used. Then, the solution can be pumped into the bottles, the overflow going back into the batch.

Bottles generally may not contain any dyes, metal specks or chemicals that can be dissolved by acids or oxidating agents. The bottles, caps, bottling filters, valves, lines and heads used can be specifically be rated for acids and oxidating agents. Caps and with organic glues, seals or other components sensitive to oxidation may be avoided, as these could neutralize and weaken the product over time.

The bottles and pouches used herein can aid in preventing decay of free radical species found within the compositions. In other embodiments, the bottles and pouches described do not further the decay process. In other words, the bottles and pouches used can be inert with respect to the radical species in the compositions. In one embodiment, a container (e.g., bottle and/or pouch) can allow less than about 10% decay/month, less than about 9% decay/month, less than about 8% decay/month, less than about 7% decay/month, less than about 6% decay/month, less than about 5% decay/month, less than about 4% decay/month, less than about 3% decay/month, less than about 2% decay/month, less than about 1% decay/month, between about 10% decay/month and about 1% decay/month, between about 5% decay/month and about 1% decay/month, about 10% decay/month, about 9% decay/month, about 8% decay/month, about 7% decay/month, about 6% decay/month, about 5% decay/month, about 4% decay/month, about 3% decay/month, about 2% decay/month, or about 1% decay/month of free radicals in the composition. In one embodiment, a bottle can only result in about 3% decay/month of superoxide. In another embodiment, a pouch can only result in about 4% decay/month of superoxide.

Large batches or scaled up batches of gel can be made. Above, the process of making large batches of composition, including redox signaling compositions, is discussed. To make large batches or scaled up batches of gel, the desired ratio of composition and rheology modifier can be used. The gel can then be put in containers or kits that are compatible with the gel.

A direct current, DC, power source is used to electrolyze water.

The saline solution can be electrolyzed for an amount of time required based on the particular results desired. For example, the saline solution can be electrolyzed from about 1 minute to about 5 days. Preferably, the saline solution can be electrolyzed from about 20 minutes to about 2 days. More preferably, the saline solution is electrolyzed for 1-60 minutes for every 1 L, 10-40 minutes for every 1 L, or 20-30 minutes for every 1 L. For example, the saline solution can be electrolyzed for 1 minute, 2 minutes, 3 minutes, 4 minutes, 5 minutes, 6 minutes, 7 minutes, 8 minutes, 9 minutes, 10 minutes, 11 minutes, 12 minutes, 13 minutes, 14 minutes, 15 minutes, 16 minutes, 17 minutes, 18 minutes, 19 minutes, 20 minutes, 21 minutes, 22 minutes, 23 minutes, 24 minutes, 25 minutes, 26 minutes, 27 minutes, 28 minutes, 29 minutes, 30 minutes, 31 minutes, 32 minutes, 33 minutes, 34 minutes, 35 minutes, 36 minutes, 37 minutes, 38 minutes, 39 minutes, 40 minutes, 41 minutes, 42 minutes, 43 minutes, 44 minutes, 45 minutes, 46 minutes, 47 minutes, 48 minutes, 49 minutes, 50 minutes, 51 minutes, 52 minutes, 53 minutes, 54 minutes, 55 minutes, 56 minutes, 57 minutes, 58 minutes, 59 minutes or 60 minutes for each 1 L of saline solution. The saline solution can be electrolyzed for any amount of time in between the from 1 to 60 minutes for every 1 L of saline solution. For example, the saline solution can be electrolyzed for a time between 1 and 2 minutes or for a time between 2 to 3 minutes etc. For example, the saline solution can be electrolyzed for about 1 minute, about 2 minutes, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, about 15 minutes, about 16 minutes, about 17 minutes, about 18 minutes, about 19 minutes, about 20 minutes, about 21 minutes, about 22 minutes, about 23 minutes, about 24 minutes, about 25 minutes, about 26 minutes, about 27 minutes, about 28 minutes, about 29 minutes, about 30 minutes, about 31 minutes, about 32 minutes, about 33 minutes, about 34 minutes, about 35 minutes, about 36 minutes, about 37 minutes, about 38 minutes, about 39 minutes, about 40 minutes, about 41 minutes, about 42 minutes, about 43 minutes, about 44 minutes, about 45 minutes, about 46 minutes, about 47 minutes, about 48 minutes, about 49 minutes, about 50 minutes, about 51 minutes, about 52 minutes, about 53 minutes, about 54 minutes, about 55 minutes, about 56 minutes, about 57 minutes, about 58 minutes, about 59 minutes or about 60 minutes for each 1 L of saline solution. Most preferably the saline solution is electrolyzed for 15 to 25 minutes or any time in between. For example, the saline solution is electrolyzed for about 15 to about 25 minutes or any time in between.

The variables of voltage, amps, frequency, time and current required depend on the compound and/or ion themselves and their respective bond strengths. To that end, the variables of voltage, amps, frequency, time and current are compound and/or ion dependent and are not limiting factors. That notwithstanding, the voltage used can be less than 40V, such as 30V or 20V or 10V or any voltage in between. The voltage can also modulate and at any time vary within a range of from 1 to 40V or from 10 to 30V or from 20 to 30V. In one embodiment, the voltage can range during a single cycle of electrolyzing. The range can be from 1 to 40V or from 10 to 30V or from 20 to 30V. These ranges are non-limiting but are shown as examples.

Waveforms with an AC ripple also referred to as pulse or spiking waveforms include: any positive pulsing currents such as pulsed waves, pulse train, square wave, sawtooth wave, spiked waveforms, pulse-width modulation (PWM), pulse duration modulation (PDM), single phase half wave rectified AC, single phase full wave rectified AC or three phase full wave rectified for example.

A bridge rectifier may be used. Other types of rectifiers can be used such as Single-phase rectifiers, Full-wave rectifiers, Three-phase rectifiers, Twelve-pulse bridge, Voltage-multiplying rectifiers, filter rectifier, a silicon rectifier, an SCR type rectifier, a high-frequency (RF) rectifier, an inverter digital-controller rectifier, vacuum tube diodes, mercury-arc valves, solid-state diodes, silicon-controlled rectifiers and the like. Pulsed waveforms can be made with a transistor regulated power supply, a dropper type power supply, a switching power supply and the like.

A transformer may be used. Examples of transformers that can be used include center tapped transformers, Auto-transformer, Capacitor voltage transformer, Distribution transformer, power transformer, Phase angle regulating transformer, Scott-T transformer, Polyphase transformer, Grounding transformer, Leakage transformer, Resonant transformer, Audio transformer, Output transformer, Laminated core Toroidal Autotransformer, Variable autotransformer, Induction regulator, Stray field transformer, Polyphase transformer, Grounding transformer, Leakage transformers, Resonant transformer, Constant voltage transformer, Ferrite core Planar transformer Oil cooled transformer, Cast resin transformer, Isolating transformer, Instrument transformer, Current transformer, Potential transformer Pulse transformer transformer Air-core transformer, Ferrite-core transformer, Transmission-line transformer, Balun Audio transformer, Loudspeaker transformer, Output transformer, Small signal transformer, Interstage coupling transformers, Hedgehog or Variocoupler.

Pulsing potentials in the power supply of the production units can also be built in. Lack of filter capacitors in the rectified power supply can cause the voltages to drop to zero a predetermined amount of times per second. For example, at 60 Hz the voltage can spike 120 times per second, resulting in a hard spike when the alternating current in the house power lines changes polarity. This hard spike, under Fourier transform, can emit a large bandwidth of frequencies. In essence, the voltage is varying from high potential to zero 120 times a second. In other embodiments, the voltage can vary from high potential to zero about 1,000 times a second, about 500 times a second, about 200 times a second, about 150 times a second, about 120 times a second, about 100 times a second, about 80 times a second, about 50 times a second, about 40 times a second, about 20 times a second, between about 200 times a second and about 20 times a second, between about 150 times a second and about 100 times a second, at least about 100 times a second, at least about 50 times a second, or at least about 120 times a second. This power modulation can allow the electrodes sample all voltages and also provides enough frequency bandwidth to excite resonances in the forming molecules themselves. The time at very low voltages can also provide an environment of low electric fields where ions of similar charge can come within close proximity to the electrodes. All of these factors together can provide a possibility for the formation of stable complexes capable of generating and preserving ROS free radicals. In one embodiment, the pulsing potentials can vary based on the desired functional parameters and capabilities of the apparatus and equipment and to that end can vary from very high potentials to low potentials and from very high frequencies to very low frequencies. In one embodiment, the voltage potential must go down to zero periodically. The voltage can go to 0V as many times per second as is physically possible. In some embodiments, the voltage is 0V between 100 and 200 times per second. In a preferred embodiment, the voltage goes down to 0V 120 times per second.

In some embodiments, there is no limit to the how high the voltage potential can go. For example, the voltage potential can pulse from 0V to 40V. In some embodiments, the voltage range can change or be changed so that the range changes as often or as little as desired within any given amount of time.

This pulsing waveform model can be used to stabilize superoxides, hydroxyl radicals and OOH* from many different components and is not limited to any particular variable such as voltage, amps, frequency, flux (current density) or current. The variables are specific to the components used. For example, water and NaCl can be combined which provide molecules and ions in solution. A 60 Hz current can be used, meaning that there are 60 cycles/120 spikes in the voltage (V) per second or 120 times wherein the V is 0 each second. When the V goes down to 0 it is believe that the 0 V allows for ions to drift apart/migrate and reorganize before the next increase in V. It is theorized that this spiking in V allows for and promotes a variable range of frequencies influencing many different types of compounds and/or ions so that this process occurs.

In one embodiment, periodic moments of 0 volts are required. Again, when the V goes down to 0 it is believe that the 0 V allows for ions to drift apart/migrate and reorganize before the next increase in V. Therefore, without being bound to theory, it is believed that this migration of ions facilitates the $1^{st}$, $2^{nd}$, and $3^{rd}$ generations of species as shown in FIG. 2. Stabilized superoxides, such as $O_2^{*-}$, are produced by this method.

In another embodiment, the V is always either 0 V or a positive potential.

Diodes may also be used. The V may drop to 0 as many times per second as the frequency is adjusted. As the frequency is increased the number of times the V drops is increased.

When the ions are affected by the electricity from the electrodes, they change. Without being bound by theory, it is believed that the electricity alters the state of some of the ions/compounds. This alteration results in the pushing of electrons out of their original orbit and/or spin state into a higher energy state and/or a single spin state. This electrolysis provides the energy to form free radicals which are ultimately formed during a multi-generational cycling of reactants and products during the electrolysis process. In other words, compounds and/or ions are initially electrolyzed so that the products that are formed are then themselves reacted with other compounds and/or ions and/or gas to form a second generation of reactants and products. This generational process then happens again so that the products from the second generation react with other compounds and/or ions in solution when the voltage spikes again.

The redox potential can be about 840 mV.

The frequency can be from 1 Hz to infinity or to 100 MHz. Preferably, the frequency is from 20 Hz to 100 Hz. More preferably, the frequency is from 40 Hz to 80 Hz. Most preferably, the frequency is 60 Hz.

In another embodiment, the frequency changes during the course of the electrolyzing process. For example, the frequency at any given moment is in the range from 20 Hz to 100 Hz. In another more preferred embodiment, the frequency at any given moment is in the range from 40 Hz to 80 Hz.

Again referencing FIG. 2, FIG. 2 illustrates an example diagram of the generation of various molecules at the electrodes, the molecules written between the electrodes depict the initial reactants and those on the outside of the electrodes depict the molecules/ions produced at the electrodes and their electrode potentials. The diagram is broken into generations where each generation relies on the products of the subsequent generations.

The end products of this electrolytic process can react within the saline solution to produce many different chemical entities. The compositions described herein can include one or more of these chemical entities. These end products can include, but are not limited to superoxides: $O2^*-$, $HO2^*$; hypochlorites: $OCl-$, $HOCl$, $NaOCl$; hypochlorates: $HClO2$, $ClO2$, $HClO3$, $HClO4$; oxygen derivatives: $O2$, $O3$, $O4^*-$, $1O$; hydrogen derivatives: $H2$, $H-$; hydrogen peroxide: $H2O2$; hydroxyl free Radical: $OH^*-$; ionic compounds: $Na+$, $Cl-$, $H+$, $OH-$, $NaCl$, $HCl$, $NaOH$; chlorine: $Cl2$; and water clusters: $n*H2O$—induced dipolar layers around ions, several variations.

In one embodiment, the composition can include at least one species such as $O2$, $H2$, $Cl2$, $OCl-$, $HOCl$, $NaOCl$, $HClO2$, $ClO2$, $HClO3$, $HClO4$, $H2O2$, $Na+$, $Cl-$, $H+$, $H$, $OH-$, $O3$, $O4^*$, $1O$, $OH^*-$, $HOCl-O2^*-$, $HOCl-O3$, $O2^*$, $HO2^*$, $NaCl$, $HCl$, $NaOH$, water clusters, or a combination thereof.

In one embodiment, the composition can include at least one species such as $H2$, $Cl2$, $OCl-$, $HOCl$, $NaOCl$, $HClO2$, $ClO2$, $HClO3$, $HClO4$, $H2O2$, $O3$, $O4^*$, $1O2$, $OH^*-$, $HOCl-O2^*-$, $HOCl-O3$, $O2^*$, $HO2^*$, water clusters, or a combination thereof.

In one embodiment, the composition can include at least one species such as $HClO3$, $HClO4$, $H2O2$, $O3$, $O4^*$, $1O2$, $OH^*-$, $HOCl-O2^*-$, $HOCl-O3$, $O2^*$, $HO2^*$, water clusters, or a combination thereof.

In one embodiment, the composition can include at least $O2^*-$ and $HOCl$.

In one embodiment, the composition can include $O2$. In one embodiment, the composition can include $H2$. In one embodiment, the composition can include $Cl2$. In one embodiment, the composition can include $OCl-$. In one embodiment, the composition can include $HOCl$. In one embodiment, the composition can include $NaOCl$. In one embodiment, the composition can include $HClO2$. In one embodiment, the composition can include $ClO2$. In one embodiment, the composition can include $HClO3$. In one embodiment, the composition can include $HClO4$. In one embodiment, the composition can include $H2O2$. In one embodiment, the composition can include $Na+$. In one embodiment, the composition can include $Cl-$. In one embodiment, the composition can include $H+$. In one embodiment, the composition can include $H$. In one embodiment, the composition can include $OH-$. In one embodiment, the composition can include $O3$. In one embodiment, the composition can include $O4^*$. In one embodiment, the composition can include $1O2$. In one embodiment, the composition can include $OH^*-$. In one embodiment, the composition can include $HOCl-O2^*-$. In one embodiment, the composition can include $HOCl-O3$. In one embodiment, the composition can include $O2^*-$. In one embodiment, the composition can include $HO2^*$. In one embodiment, the composition can include $NaCl$. In one embodiment, the composition can include $HCl$. In one embodiment, the composition can include $NaOH$. In one embodiment, the composition can include water clusters. Embodiments can include combinations thereof.

In some embodiments, hydroxyl radicals can be stabilized in the composition by the formation of radical complexes. The radical complexes can be held together by hydrogen bonding. Another radical that can be present in the composition is an $OOH^*$ radical. Still other radical complexes can include a nitroxyl-peroxide radical ($HNO-HOO^*$) and/or a hypochlorite-peroxide radical ($HOCl-HOO^*$).

The composition is stable which means, among other things, that the active agents are present, measurable or detected throughout the lifespan of the composition. In one embodiment, the active agent(s) or active ingredient(s) are superoxides and/or hydroxyl radicals. For example, the invention may be expressed as a composition wherein at least some percentage of the active ingredient(s) is present in the composition after a certain number of years, such as wherein at least 95% of the active ingredient(s) is present in the composition after 2 years, wherein at least 90% of the active ingredient(s) is present in the composition after 3 years, wherein at least 85% of the active ingredient(s) is present in the composition after 4 years, wherein at least 80% of the active ingredient(s) is present in the composition after 5 years, wherein at least 75% of the active ingredient(s) is present in the composition after 6 years, wherein at least 70% of the active ingredient(s) is present in the composition after 7 years, wherein at least 65% of the active ingredient(s) is present in the composition after 8 years, wherein at least 60% of the active ingredient(s) is present in the composition after 9 years, wherein at least 55% of the active ingredient(s) is present in the composition after 10 years and the like.

Stable oxygen radicals can remain stable for about 3 months, about 6 months, about 9 months, about 12 months, about 15 months, about 18 months, about 21 months, between about 9 months and about 15 months, between about 12 months and about 18 months, at least about 9 months, at least about 12 months, at least about 15 months, at least about 18 months, about 24 months, about 30 months, about 50 months, about 100 months, about 200 months, about 300 months, about 400 months, about 500 months, about 1000 months, about 2000 months, or longer.

Stable oxygen radicals can be substantially stable. Substantially stable can mean that the stable oxygen radical can remain at a concentration greater than about 75% relative to the concentration on day 1 (day 1 meaning on the day or at the time it was produced), greater than about 80%, greater than about 85%, greater than about 90%, greater than about 95%, greater than about 96%, greater than about 97%, greater than about 98%, or greater than about 99% over a given time period as described above. For example, in one embodiment, the stable oxygen is at a concentration greater than about 95% relative to day 1 for at least 1 year. In another embodiment, the at least one oxygen radical is at a concentration greater than about 98% for at least 1 year.

Stable can mean that the stable oxygen radical can remain at a concentration greater than about 75% relative to the concentration on day 1 or the day is was produced, greater than about 80% relative to the concentration on day 1 or the day is was produced, greater than about 85% relative to the concentration on day 1 or the day is was produced, greater than about 90% relative to the concentration on day 1 or the day is was produced, greater than about 95% relative to the concentration on day 1 or the day is was produced, greater than about 96% relative to the concentration on day 1 or the day is was produced, greater than about 97% relative to the concentration on day 1 or the day is was produced, greater than about 98% relative to the concentration on day 1 or the day is was produced, or greater than about 99% relative to the concentration on day 1 or the day is was produced over a given time period as described above. For example, in one embodiment, the stable oxygen is at a concentration greater than about 95% relative to day 1 for at least 1 year. In another embodiment, the at least one oxygen radical is at a concentration greater than about 98% for at least 1 year.

Stability as used herein can also refer to the amount of a particular specie when compared to a reference sample. In some embodiments, the reference sample can be made in 1 L vessels with 0.9% isotonic solution electrolyzed with 3 Amps at 40° F., for 3 mins. In another embodiment, the reference sample can be made according to a process as otherwise described herein. The reference standard can also be bottled directly off the processing line as a "fresh" sample.

In other embodiments, the at least one oxygen radical is greater than about 86% stable for at least 4 years, greater than about 79% stable for at least 6 years, greater than about 72% stable for at least 8 years, greater than about 65% stable for at least 10 years, or 100% stable for at least 20 years.

In still other embodiments, the at least one oxygen radical is greater than about 95% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 96% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 97% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 98% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is greater than about 99% stable for at least 2 years, at least 3 years, at least 4 years, at least 5 years, at least 6 years, at least 7 years, at least 8 years, at least 9 years, at least 10 years, at least 15 years, or at least 20 years. In still other embodiments, the at least one oxygen radical is 100% stable for at least 2 years, at least 3 years, at least 4 years, at least 5 years, at least 6 years, at least 7 years, at least 8 years, at least 9 years, at least 10 years, at least 15 years, or at least 20 years.

The stability of oxygen radicals can also be stated as a decay rate over time. Decay of superoxides is described in Ong, Ta-Chung, "Detailed Mechanistic and Optimization of the Photochemical Production Method of Superoxide" (2007). Honors Theses. Paper 267. http://digitalcommons.colby.edu/honorstheses/267_Retrieved_14_August_2013 which is incorporated herein in its entirety. Substantially stable can mean a decay rate less than 1% per month, less than 2% per month, less than 3% per month, less than 4% per month, less than 5% per month, less than 6% per month, less than 10% per month, less than 3% per year, less than 4% per year, less than 5% per year, less than 6% per year, less than 7% per year, less than 8% per year, less than 9% per year, less than 10% per year, less than 15% per year, less than 20% per year, less than 25% per year, between less than 3% per month and less than 7% per year.

In other embodiments, stability can be expressed as a half-life. A half-life of the stable oxygen radical can be about 6 months, about 1 year, about 2 years, about 3 years, about 4 years, about 5 years, about 10 years, about 15 years, about 20 years, about 24 years, about 30 years, about 40 years, about 50 years, greater than about 1 year, greater than about 2 years, greater than about 10 years, greater than about 20 years, greater than about 24 years, between about 1 year and about 30 years, between about 6 years and about 24 years, or between about 12 years and about 30 years.

Reactive species' concentrations in the life enhancing solutions, detected by fluorescence photo spectroscopy, may not significantly decrease in time. Mathematical models show that bound HOCl—*O2— complexes are possible at room temperature. Molecular complexes can preserve volatile components of reactive species. For example, reactive species concentrations in whole blood as a result of molecular complexes may prevent reactive species degradation over time.

Reactive species can be further divided into "reduced species" (RS) and "reactive oxygen species" (ROS). Reactive species can be formed from water molecules and sodium chloride ions when restructured through a process of forced electron donation. Electrons from lower molecular energy configurations in the salinated water may be forced into higher, more reactive molecular configurations. The species from which the electron was taken can be "electron hungry" and is called the RS and can readily become an electron acceptor (or proton donor) under the right conditions such as $H_2O_2$ or $O_2$. The species that obtains the high-energy electron can be an electron donor and is called the ROS and may energetically release these electrons under the right conditions.

When an energetic electron in ROS is unpaired it is called a "radical". ROS and RS can recombine to neutralize each other by the use of a catalytic enzyme. Three elements, (1) enzymes, (2) electron acceptors, and (3) electron donors can all be present at the same time and location for neutralization to occur.

Depending on the parameters used to produce the composition, different components can be present at different concentrations. In one embodiment, the composition can include about 0.1 ppt, about 0.5 ppt, about 1 ppt, about 1.5 ppt, about 2 ppt, about 2.5 ppt, about 3 ppt, about 3.5 ppt, about 4 ppt, about 4.5 ppt, about 5 ppt, about 6 ppt, about 7 ppt, about 8 ppt, about 9 ppt, about 10 ppt, about 20 ppt, about 50 ppt, about 100 ppt, about 200 ppt, about 400 ppt, about 1,000 ppt, between about 0.1 ppt and about 1,000 ppt, between about 0.1 ppt and about 100 ppt, between about 0.1 ppt and about 10 ppt, between about 2 ppt and about 4 ppt, at least about 0.1 ppt, at least about 2 ppt, at least about 3 ppt, at most about 10 ppt, or at most about 100 ppt of OCl—. In some embodiments, OCl— can be present at 3 ppt. In other embodiments, OCl— can be present at 1 to 100 ppm or from 10 to 30 ppm or from 16 to 24 ppm. In particular embodiments, OCl— is present at 16 ppm, 17 ppm, 18 ppm, 19 ppm, 20 ppm, 21 ppm, 22 ppm, 23 pm, 24 ppm or 25 ppm. In other embodiments, OCl— can be the predominant chlorine containing species in the composition.

In order to determine the relative concentrations and rates of production of each of these during electrolysis, certain general chemical principles can be helpful:

1) A certain amount of Gibbs free energy is required for construction of the molecules; Gibbs free energy is proportional to the differences in electrode potentials listed in FIG. 2. Reactions with large energy requirements are less likely to happen, for example an electrode potential of −2.71V (compared to Hydrogen reduction at 0.00V) is required to make sodium metal:

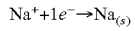
$Na^+ + 1e^- \rightarrow Na_{(s)}$

Such a large energy difference requirement makes this reaction less likely to happen compared to other reactions with smaller energy requirements. Electron(s) from the electrodes may be preferentially used in the reactions that require lesser amounts of energy, such as the production of hydrogen gas.

2) Electrons and reactants are required to be at the same micro-locality on the electrodes. Reactions that require several reactants may be less likely to happen, for example:

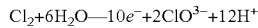
$Cl_2 + 6H_2O - 10e^- + 2ClO_3^- + 12H^+$ requires that 6 water molecules and a Cl2 molecule to be at the electrode at the same point at the same time and a release of 10 electrons to simultaneously occur. The probability of this happening generally is smaller than other reactions requiring fewer and more concentrated reactants to coincide, but such a reaction may still occur.

3) Reactants generated in preceding generations can be transported or diffuse to the electrode where reactions happen. For example, dissolved oxygen (O2) produced on the anode from the first generation can be transported to the cathode in order to produce superoxides and hydrogen peroxide in the second generation. Ions can be more readily transported: they can be pulled along by the electric field due to their electric charge. In order for chlorates, to be generated, for example, HClO2 can first be produced to start the cascade, restrictions for HClO2 production can also restrict any subsequent chlorate production. Lower temperatures can prevent HClO2 production.

Stability and concentration of the above products can depend, in some cases substantially, on the surrounding environment. The formation of complexes and water clusters can affect the lifetime of the moieties, especially the free radicals.

In a pH-neutral aqueous solution (pH around 7.0) at room temperature, superoxide free radicals (O2*-) have a half-life of 10's of milliseconds and dissolved ozone (O3) has a half-life of about 20 min. Hydrogen peroxide (H2O2) is relatively long-lived in neutral aqueous environments, but this can depend on redox potentials and UV light. Other entities such as HCl and NaOH rely on acidic or basic environments, respectively, in order to survive. In pH-neutral solutions, H+ and OH— ions have concentrations of approximately 1 part in 10,000,000 in the bulk aqueous solution away from the electrodes. H— and 1O can react quickly. The stability of most of these moieties mentioned above can depend on their microenvironment.

Superoxides and ozone can form stable Van de Waals molecular complexes with hypochlorites. Clustering of polarized water clusters around charged ions can also have the effect of preserving hypochlorite-superoxide and hypochlorite-ozone complexes. Such complexes can be built through electrolysis on the molecular level on catalytic substrates, and may not occur spontaneously by mixing together components. Hypochlorites can also be produced spontaneously by the reaction of dissolved chlorine gas (Cl2) and water. As such, in a neutral saline solution the formation of on or more of the stable molecules and complexes may exist: dissolved gases: O2, H2, Cl2; hypochlorites: OCl—, HOCl, NaOCl; hypochlorates: HClO2, ClO2, HClO3, HClO4; hydrogen peroxide: H2O2; ions: Na+, Cl—, H+, H—, OH—; ozone: O3, O4*-; singlet oxygen: 1O; hydroxyl free radical: OH*—; superoxide complexes: HOCl—O2*-; and ozone complexes: HOCl—O3. One or more of the above molecules can be found within the compositions and composition described herein.

A complete quantum chemical theory can be helpful because production is complicated by the fact that different temperatures, electrode geometries, flows and ion transport mechanisms and electrical current modulations can materially change the relative/absolute concentrations of these components, which could result in producing different distinct compositions. As such, the selection of production parameters can be critical. The amount of time it would take to check all the variations experimentally may be prohibitive.

The chlorine concentration of the electrolyzed solution can be about 5 ppm, about 10 ppm, about 15 ppm, about 20 ppm, about 21 ppm, about 22 ppm, about 23 ppm, about 24 ppm, about 25 ppm, about 26 ppm, about 27 ppm, about 28 ppm, about 29 ppm, about 30 ppm, about 31 ppm, about 32 ppm, about 33 ppm, about 34 ppm, about 35 ppm, about 36 ppm, about 37 ppm, about 38 ppm, less than about 38 ppm, less than about 35 ppm, less than about 32 ppm, less than about 28 ppm, less than about 24 ppm, less than about 20 ppm, less than about 16 ppm, less than about 12 ppm, less than about 5 ppm, between about 30 ppm and about 34 ppm, between about 28 ppm and about 36 ppm, between about 26 ppm and about 38 ppm, between about 20 ppm and about 38 ppm, between about 5 ppm and about 34 ppm, between about 10 ppm and about 34 ppm, or between about 15 ppm and about 34 ppm. In one embodiment, the chlorine concentration is about 32 ppm. In another embodiment, the chlorine concentration is less than about 41 ppm.

In some embodiments, the chloride species can be present from 1400 to 1650 ppm. In a particular embodiment, the chloride species can be present from 1400 to 1500 ppm or from 1500 to 1600 ppm or from 1600 to 1650 ppm. In other embodiments, the chloride anion can be present in an amount that is predetermined based on the amount of NaCl added to the initial solution.

In some embodiments, the sodium species can be present from 1000 to 1400 ppm. In a particular embodiment, the sodium species can be present from 1100 to 1200 ppm or from 1200 to 1300 ppm or from 1300 to 1400 ppm. For example, the sodium species can be present at 1200 ppm. In other embodiments, the sodium anion can be present in an amount that is predetermined based on the amount of NaCl added to the initial solution.

The saline concentration in the electrolyzed solution can be about 0.10% w/v, about 0.11% w/v, about 0.12% w/v, about 0.13% w/v, about 0.14% w/v, about 0.15% w/v, about 0.16% w/v, about 0.17% w/v, about 0.18% w/v, about 0.19% w/v, about 0.20% w/v, about 0.30% w/v, about 0.40% w/v, about 0.50% w/v, about 0.60% w/v, about 0.70% w/v, between about 0.10% w/v and about 0.20% w/v, between about 0.11% w/v and about 0.19% w/v, between about 0.12% w/v and about 0.18% w/v, between about 0.13% w/v and about 0.17% w/v, or between about 0.14% w/v and about 0.16% w/v.

The composition generally can include electrolytic and/or catalytic products of pure saline that mimic redox signaling molecular compositions of the native salt water compounds found in and around cells. The composition can be fine-tuned to mimic or mirror molecular compositions of different biological media. The composition can have reactive species other than chlorine present. As described, species present in the compositions and compositions described herein can include, but are not limited to $O_2$, $H_2$, $Cl_2$, $OCl-$, $HOCl$, $NaOCl$, $HClO_2$, $ClO_2$, $HClO_3$, $HClO_4$, $H_2O_2$, $Na+$, $Cl-$, $H+$, $H-$, $OH-$, $O_3$, $O_4*-$, $1O$, $OH*-$, $HOCl-O_2*-$, $HOCl-O_3$, $O_2*$, $HO_2*$, $NaCl$, $HCl$, $NaOH$, and water clusters: $n*H_2O$—induced dipolar layers around ions, several variations.

In some embodiments, substantially no organic material is present in the compositions described. Substantially no organic material can be less than about 0.1 ppt, less than about 0.01 ppt, less than about 0.001 ppt or less than about 0.0001 ppt of total organic material.

The composition can be stored and bottled as needed to ship to consumers. The composition can have a shelf life of about 5 days, about 30 days, about 3 months, about 6 months, about 9 months, about 1 year, about 1.5 years, about 2 years, about 3 years, about 5 years, about 10 years, at least about 5 days, at least about 30 days, at least about 3 months, at least about 6 months, at least about 9 months, at least about 1 year, at least about 1.5 years, at least about 2 years, at least about 3 years, at least about 5 years, at least about 10 years, between about 5 days and about 1 year, between about 5 days and about 2 years, between about 1 year and about 5 years, between about 90 days and about 3 years, between about 90 days and about 5 year, or between about 1 year and about 3 years.

Quality Assurance testing can be done on every batch before the batch can be approved for bottling or can be performed during or after bottling. A 16 oz. sample bottle can be taken from each complete batch and analyzed. Determinations for presence of contaminants such as heavy metals or chlorates can be performed. Then pH, Free and Total Chlorine concentrations and reactive molecule concentrations of the active ingredients can be analyzed by fluorospectroscopy methods. These results can be compared to those of a standard solution which is also tested along side every sample. If the results for the batch fall within a certain range relative to the standard solution, it can be approved. A chemical chromospectroscopic MS analysis can also be run on random samples to determine if contaminants from the production process are present.

The gel or hydrogel can be applied topically. The topical product can be applied in ounce units such as from 0.5 oz to 20 oz or as desired by the user. When administered, it can be administered once, twice, three times, four times or more a day. Each administration can be about 1 oz, about 2 oz, about 3 oz, about 4 oz, about 5 oz, about 6 oz, about 7 oz, about 8 oz, about 9 oz, about 10 oz, about 11 oz, about 12 oz, about 16 oz, or about 20 oz. In one embodiment, the composition can be administered at a rate of about 4 oz twice a day.

In other embodiments, the administration can be acute or long term. For example, the composition can be administered for a day, a week, a month, a year or longer. In other embodiments, the composition can simply be applied as needed.

Example 1

Figure 3:
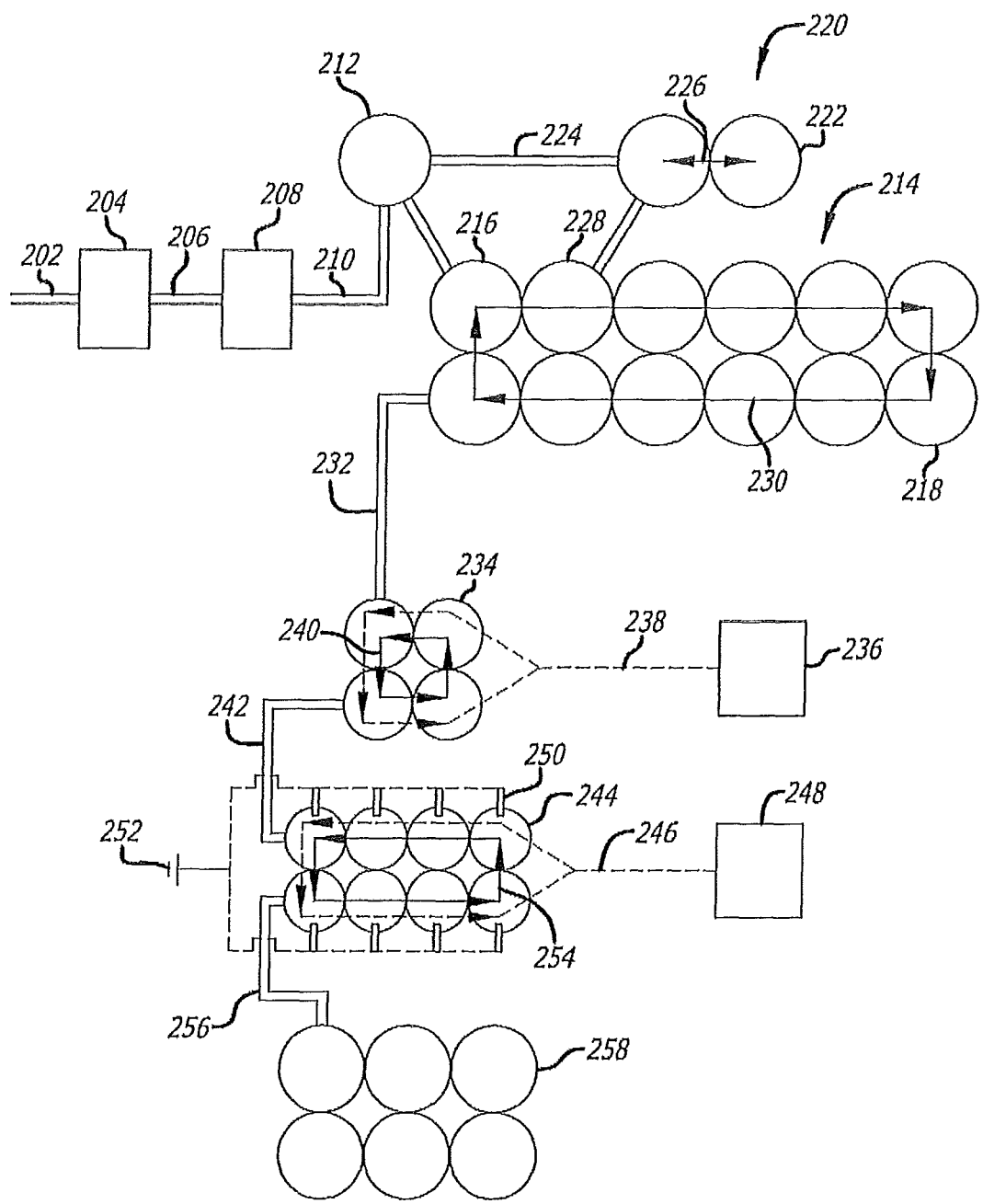
FIG. 3 illustrates a plan view of a process and system for producing a composition according to the present description.

Example 1 demonstrates a process for producing a composition comprising at least one reduced species (RS) and at least one reactive oxygen species (ROS). Specifically, FIG. 3 illustrates a plan view of a process and system for producing a redox signaling composition comprising redox signaling agents according to the present description. One skilled in the art understands that changes can be made to the system to alter the composition, and these changes are within the scope of the present description.

Incoming water 202 can be subjected to reverse osmosis system 204 at a temperature of about 15-20° C. to achieve purified water 206 with about 8 ppm of total dissolved solids. Purified water 206, is then fed at a temperature of about 15-20° C. into distiller 208 and processed to achieve distilled water 210 with about 0.5 ppm of total dissolved solids. Distilled water 210 can then be stored in tank 212.

Figure 4:
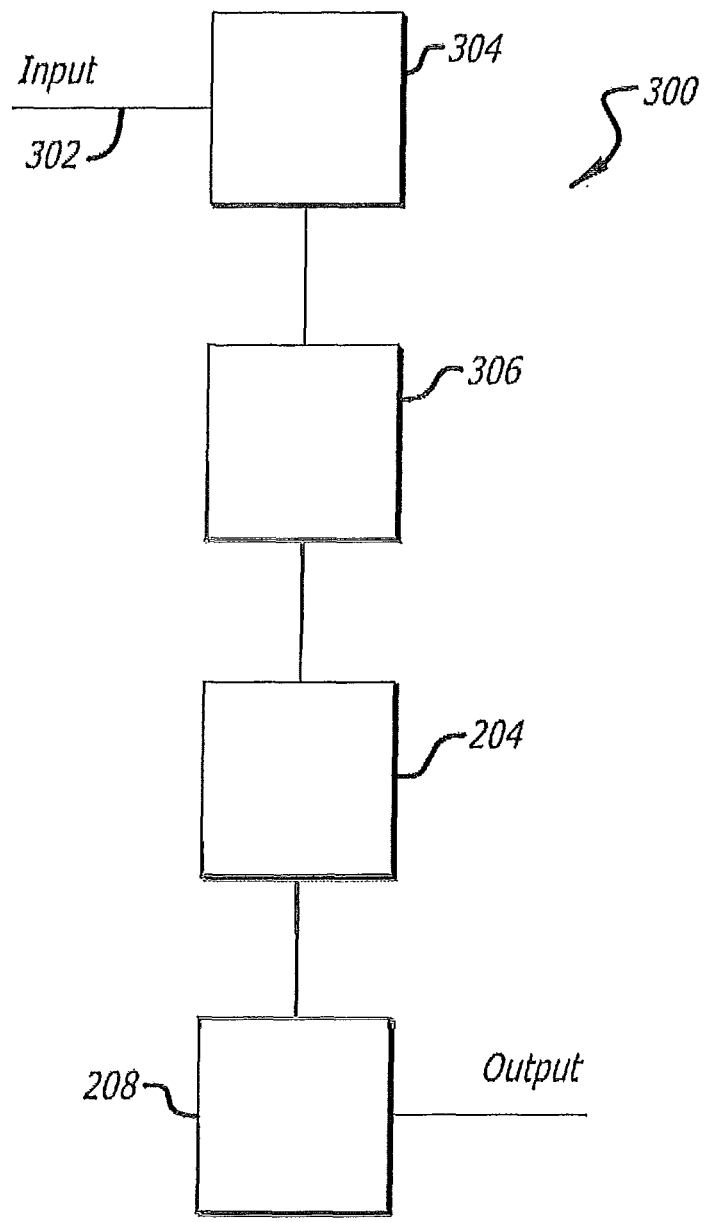
FIG. 4 illustrates an example system for preparing water for further processing into a composition described herein.

FIG. 4 illustrates an example system for preparing water for further processing into a therapeutic composition. System 300 can include a water source 302 which can feed directly into a carbon filter 304. After oils, alcohols, and other volatile chemical residuals and particulates are removed by carbon filter 304, the water can be directed to resin beds within a water softener 306 which can remove dissolved minerals. Then, as described above, the water can pass through reverse osmosis system 204 and distiller 208.

Referring again to FIG. 3, distilled water 210 can be gravity fed as needed from tank 212 into saline storage tank cluster 214 using line 216. Saline storage tank cluster 214 in one embodiment can include twelve tanks 218. Each tank 218 can be filled to about 1,300 gallons with distilled water 210. A handheld meter can be used to test distilled water 210 for salinity.

Saline storage tank cluster 214 is then salted using a brine system 220. Brine system 220 can include two brine tanks 222. Each tank can have a capacity of about 500 gallons. Brine tanks 222 are filled to 475 gallons with distilled water 210 using line 224 and then NaCl is added to the brine tanks 222 at a ratio of about 537.5 g/gal of liquid. At this point, the water is circulated 226 in the brine tanks 222 at a rate of about 2,000 gal/hr for about 4 days.

Prior to addition of brine to tanks 218, the salinity of the water in tanks 218 can be tested using a handheld conductivity meter such as an YSI ECOSENSE® ecp300 (YSI Inc., Yellow Springs, Ohio). Any corrections based on the salinity measurements can be made at this point. Brine solution 228 is then added to tanks 218 to achieve a salt concentration of about 10.75 g/gal. The salted water is circulated 230 in tanks 218 at a rate of about 2,000 gal/hr for no less than about 72 hours. This circulation is performed at room temperature. A handheld probe can again be used to test salinity of the salinated solution. In one embodiment, the salinity is about 2.8 ppth.

In one method for filling and mixing the salt water in the brine holding tanks, the amount of liquid remaining in the tanks is measured. The amount of liquid remaining in a tank is measured by recording the height that the liquid level is from the floor that sustains the tank, in centimeters, and referencing the number of gallons this height represents. This can be done from the outside of the tank if the tank is semi-transparent. The initial liquid height in both tied tanks can also be measured. Then, after ensuring that the output valve is closed, distilled water can be pumped in. The amount of distilled water that is being pumped into a holding tank can then be calculated by measuring the rise in liquid level: subtracting the initial height from the filled height and then multiplying this difference by a known factor.

The amount of salt to be added to the tank is then calculated by multiplying 11 grams of salt for every gallon of distilled water that has been added to the tank. The salt can be carefully weighed out and dumped into the tank.

The tank is then agitated by turning on the recirculation pump and then opening the top and bottom valves on the tank. Liquid is pumped from the bottom of the tank to the top. The tank can be agitated for three days before it may be ready to be processed.

After agitating the tank for more than 6 hours, the salinity is checked with a salinity meter by taking a sample from the tank and testing it. Salt or water can be added to adjust the salinity within the tanks. If either more water or more salt is added then the tanks are agitated for 6 more hours and tested again. After about three days of agitation, the tank is ready to be processed.

Salinated water 232 is then transferred to cold saline tanks 234. In one embodiment, four 250 gal tanks are used. The amount of salinated water 232 moved is about 1,000 gal. A chiller 236 such as a 16 ton chiller is used to cool heat exchangers 238 to about 0-5° C. The salinated water is circulated 240 through the heat exchangers which are circulated with propylene glycol until the temperature of the salinated water is about 4.5-5.8° C. Chilling the 1,000 gal of salinated water generally takes about 6-8 hr.

Cold salinated water 242 is then transferred to processing tanks 244. In one embodiment, eight tanks are used and each can have a capacity of about 180 gal. Each processing tank 244 is filled to about 125 gal for a total of 1,000 gal. Heat exchangers 246 are again used to chill the cold salinated water 242 added to processing tanks 244. Each processing tank can include a cylinder of chilling tubes and propylene glycol can be circulated. The heat exchangers can be powered by a 4-5 ton chiller 248. The temperature of cold salinated water 242 can remain at 4.5-5.8° C. during processing.

Prior to transferring aged salt water to processing tanks, the aged salt water can be agitated for about 30 minutes to sufficiently mix the aged salt water. Then, the recirculation valves can then be closed, the appropriate inlet valve on the production tank is opened, and the tank filled so that the salt water covers the cooling coils and comes up to the fill mark (approximately 125 gallons).

Once the aged salt water has reached production temperature, the pump is turned off but the chiller left on. The tank should be adequately agitated or re-circulated during the whole duration of electrochemical processing and the temperature should remain constant throughout.

Each processing tank 244 includes electrode 250. Electrodes 250 can be 3 inches tall circular structures formed of titanium and plated with platinum. Electrochemical processing of the cold salinated water can be run for 8 hr. A power supply 252 is used to power the eight electrodes (one in each processing tank 244) to 7 amps each for a total of 56 amps. The cold salinated water is circulated 254 during electrochemical processing at a rate of about 1,000 gal/hr.

An independent current meter can be used to set the current to around 7.0 Amps. Attention can be paid to ensure that the voltage does not exceed 12V and does not go lower than 9V. Normal operation can be about 10V. Alternatively, normal operation can be at 1V, 2V, 3V, 4V, 5V, 6V, 7V, 8V, 9V, 10V, 11V or 12V.

A run timer can be set for a prescribed time (about 4.5 to 5 hours). Each production tank can have its own timer and/or power supply. Electrodes should be turned off after the timer has expired.

The production tanks can be checked periodically. The temperature and/or electrical current can be kept substantially constant. At the beginning, the electrodes can be visible from the top, emitting visible bubbles. After about 3 hours, small bubbles of un-dissolved oxygen can start building up in the tank as oxygen saturation occurs, obscuring the view of the electrodes. A slight chlorine smell can be normal.

After the 8 hour electrochemical processing is complete, life enhancing water 256 has been created with a pH of about 6.8-8.2 and 32 ppm of chlorine. The composition 256 is transferred to storage tanks 258. The product ASEA can be made by this process. Preferably, the product ASEA is made by the process of this Example 1.

Example 2

Characterization of a Solution Produced as Described in Example 1

A composition produced as described in Example 1 was analyzed using a variety of different characterization techniques. ICP/MS and 35Cl NMR were used to analyze and quantify chlorine content. Headspace mass spectrometry analysis was used to analyze adsorbed gas content in the composition. 1H NMR was used to verify the organic matter content in the composition. 31P NMR and EPR experiments utilizing spin trap molecules were used to explore the composition for free radicals.

The composition was received and stored at about 4° C. when not being used.

Chlorine NMR

Sodium hypochlorite solutions were prepared at different pH values. 5% sodium hypochlorite solution had a pH of 12.48. Concentrated nitric acid was added to 5% sodium hypochlorite solution to create solutions that were at pH of 9.99, 6.99, 5.32, and 3.28. These solutions were then analyzed by NMR spectroscopy. The composition had a measured pH of 8.01 and was analyzed directly by NMR with no dilutions.

NMR spectroscopy experiments were performed using a 400 MHz Bruker spectrometer equipped with a BBO probe.

35Cl NMR experiments were performed at a frequency of 39.2 MHz using single pulse experiments. A recycle delay of 10 seconds was used, and 128 scans were acquired per sample. A solution of NaCl in water was used as an external chemical shift reference. All experiments were performed at room temperature.

Figure 5:
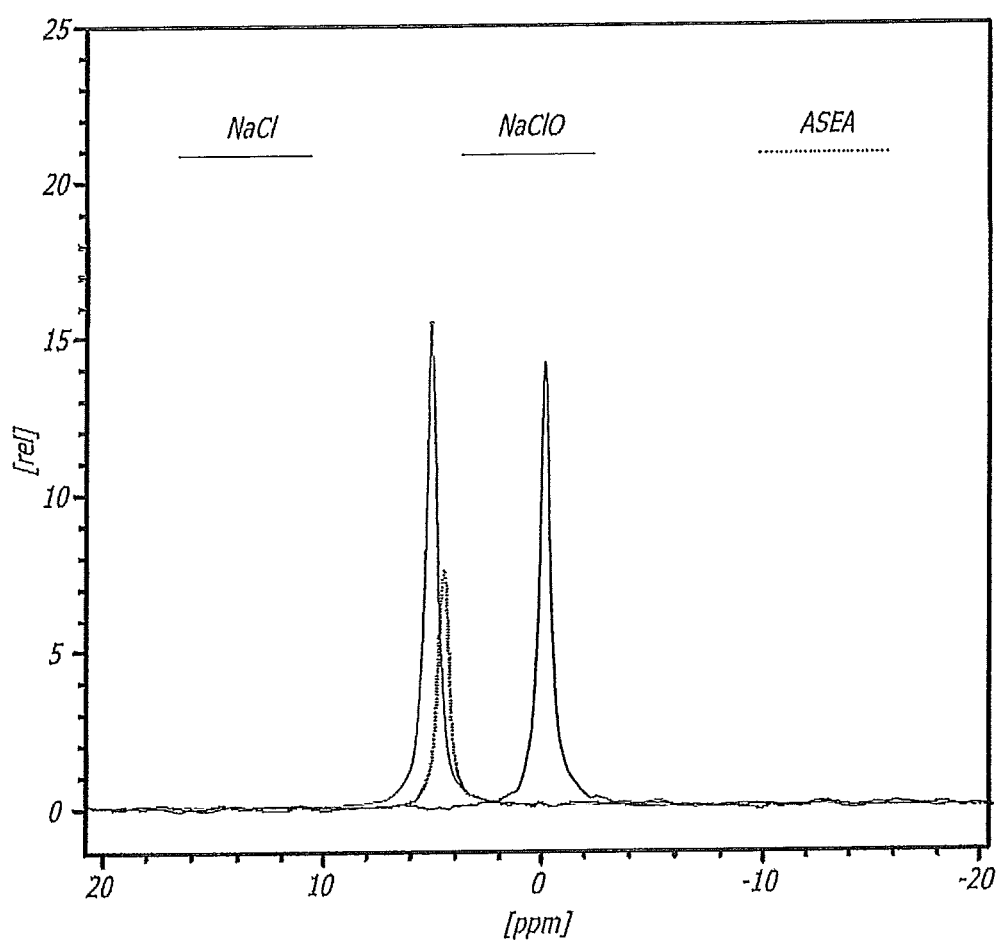
FIG. 5 illustrates a Cl35 spectrum of NaCl, NaClO solution at a pH of 12.48, and a composition described herein (the composition is labeled "ASEA").

35Cl NMR spectra were collected for NaCl solution, NaClO solutions adjusted to different pH values, and the composition. FIG. 5 illustrates a Cl35 spectrum of NaCl, NaClO solution at a pH of 12.48, and the composition. The chemical shift scale was referenced by setting the Cl— peak to 0 ppm. NaClO solutions above a pH=7 had identical spectra with a peak at approximately 5.1 ppm. Below pH of 7.0, the ClO— peak disappeared and was replaced by much broader, less easily identifiable peaks. The composition was presented with one peak at approximately 4.7 ppm, from ClO— in the composition. This peak was integrated to estimate the concentration of ClO— in the composition, which was determined to be 2.99 ppt or 0.17 M of ClO— in the composition.

Proton NMR

An ASEA sample was prepared by adding 550 μL of ASEA and 50 μL of D2O (Cambridge Isotope Laboratories) to an NMR tube and vortexing the sample for 10 seconds. 1H NMR experiments were performed on a 700 MHz Bruker spectrometer equipped with a QNP cryogenically cooled probe. Experiments used a single pulse with pre-saturation on the water resonance experiment. A total of 1024 scans were taken. All experiments were performed at room temperature.

Figure 6:
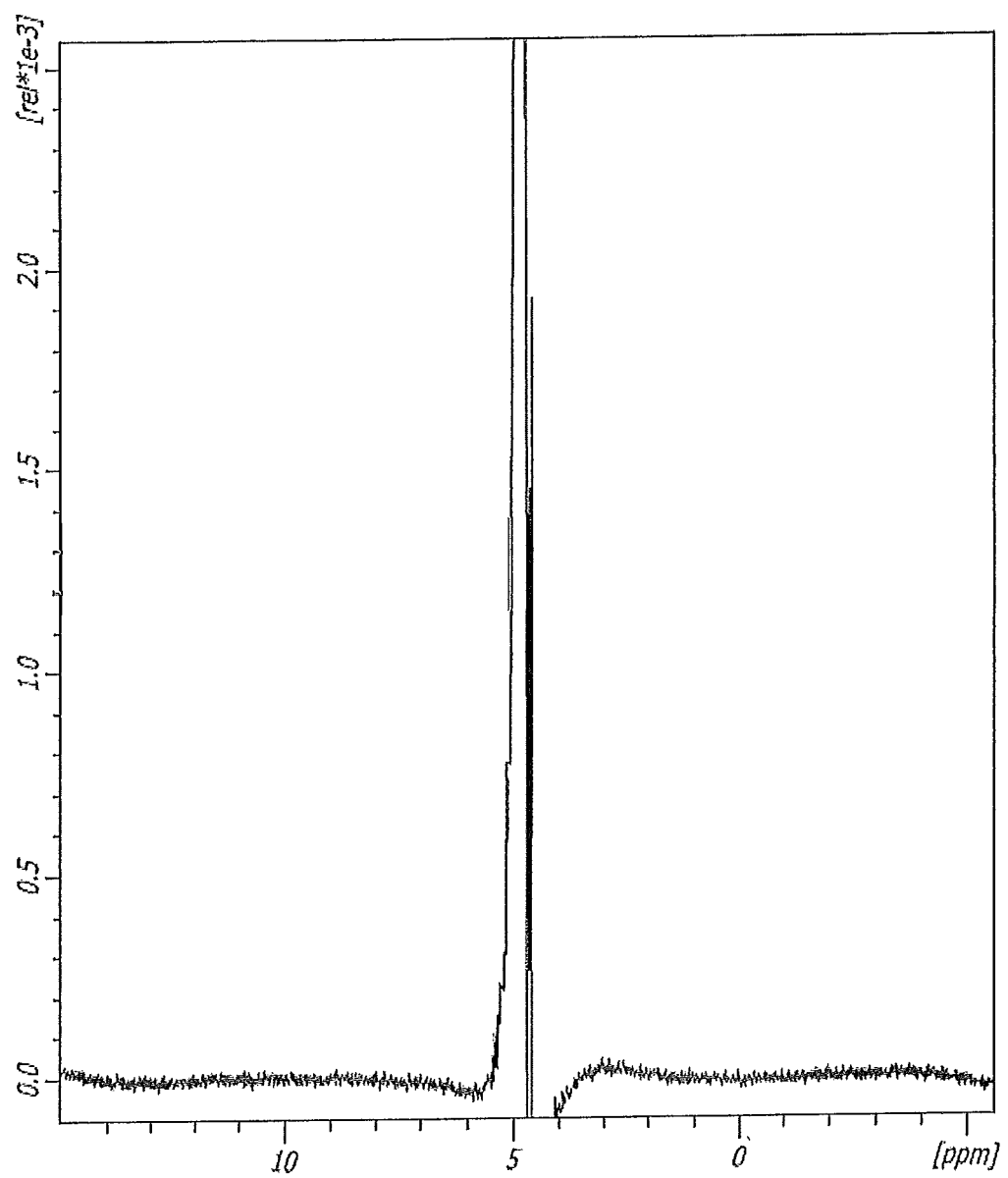
FIG. 6 illustrates a 1H NMR spectrum of a composition of the present disclosure.

A 1H NMR spectrum of the composition was determined and is presented in FIG. 6. Only peaks associated with water were able to be distinguished from this spectrum. This spectrum show that very little if any organic material can be detected in the composition using this method.

Phosphorous NMR and Mass Spectrometry

DIPPMPO (5-(Diisopropoxyphosphoryl)-5-1-pyrroline-N-oxide) (VWR) samples were prepared by measuring about 5 mg of DIPPMPO into a 2 mL centrifuge tube. This tube then had 550 μL of either the composition or water added to it, followed by 50 μL of D2O. A solution was also prepared with the composition but without DIPPMPO. These solutions were vortexed and transferred to NMR tubes for analysis. Samples for mass spectrometry analysis were prepared by dissolving about 5 mg of DIPPMPO in 600 μL of the composition and vortexing, then diluting the sample by adding 100 μL of sample and 900 μL of water to a vial and vortexing.

NMR experiments were performed using a 700 MHz Bruker spectrometer equipped with a QNP cryogenically cooled probe. Experiments performed were a single 30° pulse at a 31P frequency of 283.4 MHz. A recycle delay of 2.5 seconds and 16384 scans were used. Phosphoric acid was used as an external standard. All experiments were performed at room temperature.

Mass spectrometry experiments were performed by directly injecting the ASEA/DIPPMPO sample into a Waters/Synapt Time of Flight mass spectrometer. The sample was directly injected into the mass spectrometer, bypassing the LC, and monitored in both positive and negative ion mode.

Figure 7:
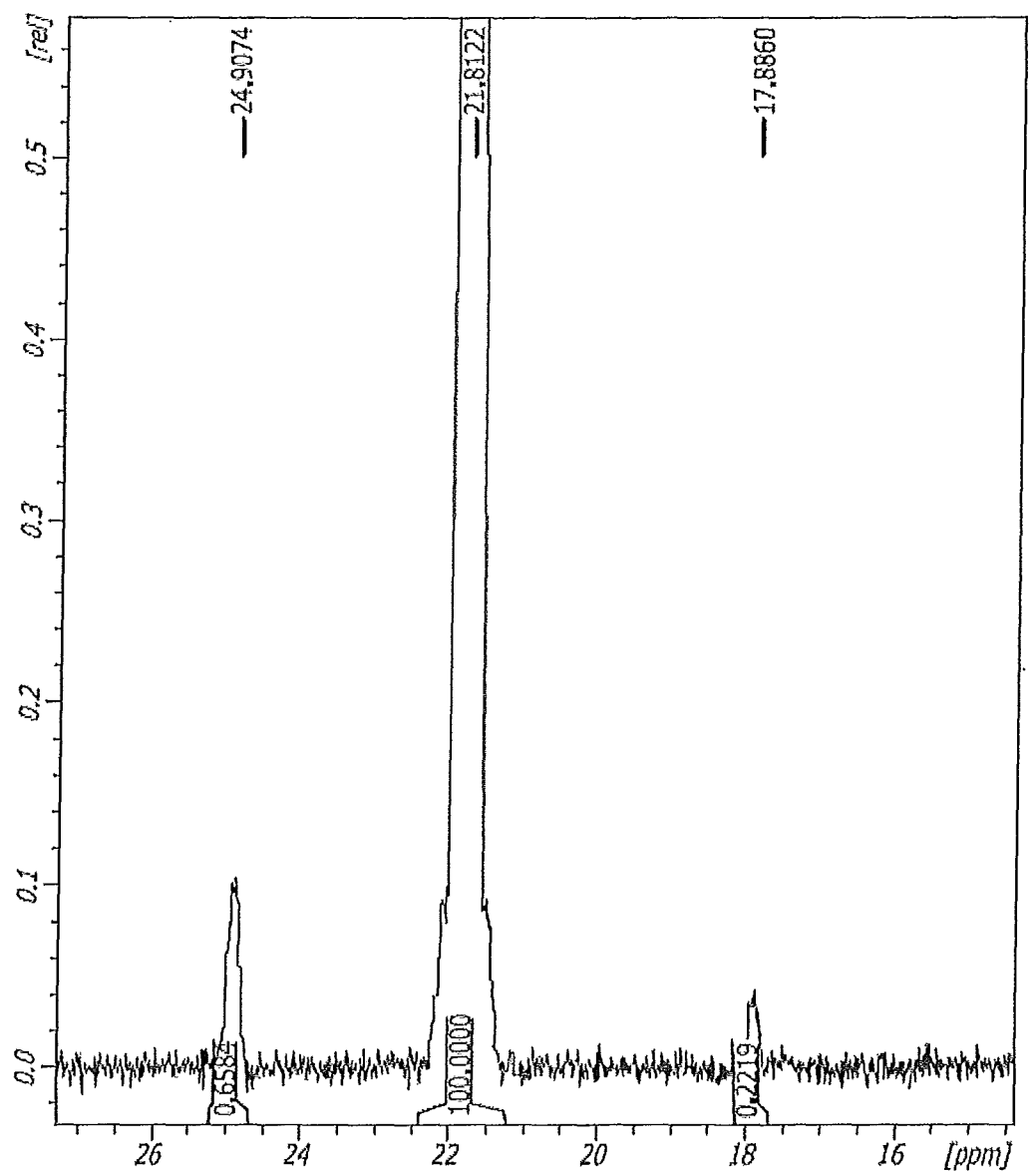
FIG. 7 illustrates a 31P NMR spectrum of DIPPMPO combined with a composition described herein.

31P NMR spectra were collected for DIPPMPO in water, the composition alone, and the composition with DIPPMPO added to it. An external reference of phosphoric acid was used as a chemical shift reference. FIG. 7 illustrates a 31P NMR spectrum of DIPPMPO combined with the composition. The peak at 21.8 ppm was determined to be DIPPMPO and is seen in both the spectrum of DIPPMPO with the composition (FIG. 7) and without the composition (not pictured). The peak at 24.9 ppm is most probably DIPPMPO/OH. as determined in other DIPPMPO studies. This peak may be seen in DIPPMPO mixtures both with and without the composition, but is detected at a much greater concentration in the solution with the composition. In the DIPPMPO mixture with the composition, there is another peak at 17.9 ppm. This peak may be from another radical species in the composition such as OOH. or possibly a different radical complex. The approximate concentrations of spin trap complexes in the composition/DIPPMPO solution are as follows:

| Solution | Concentration |
| --- | --- |
| DIPPMPO | 36.6 mM |
| DIPPMPO/OH• | 241 μM |
| DIPPMPO/radical | 94 μM |

Figure 8:
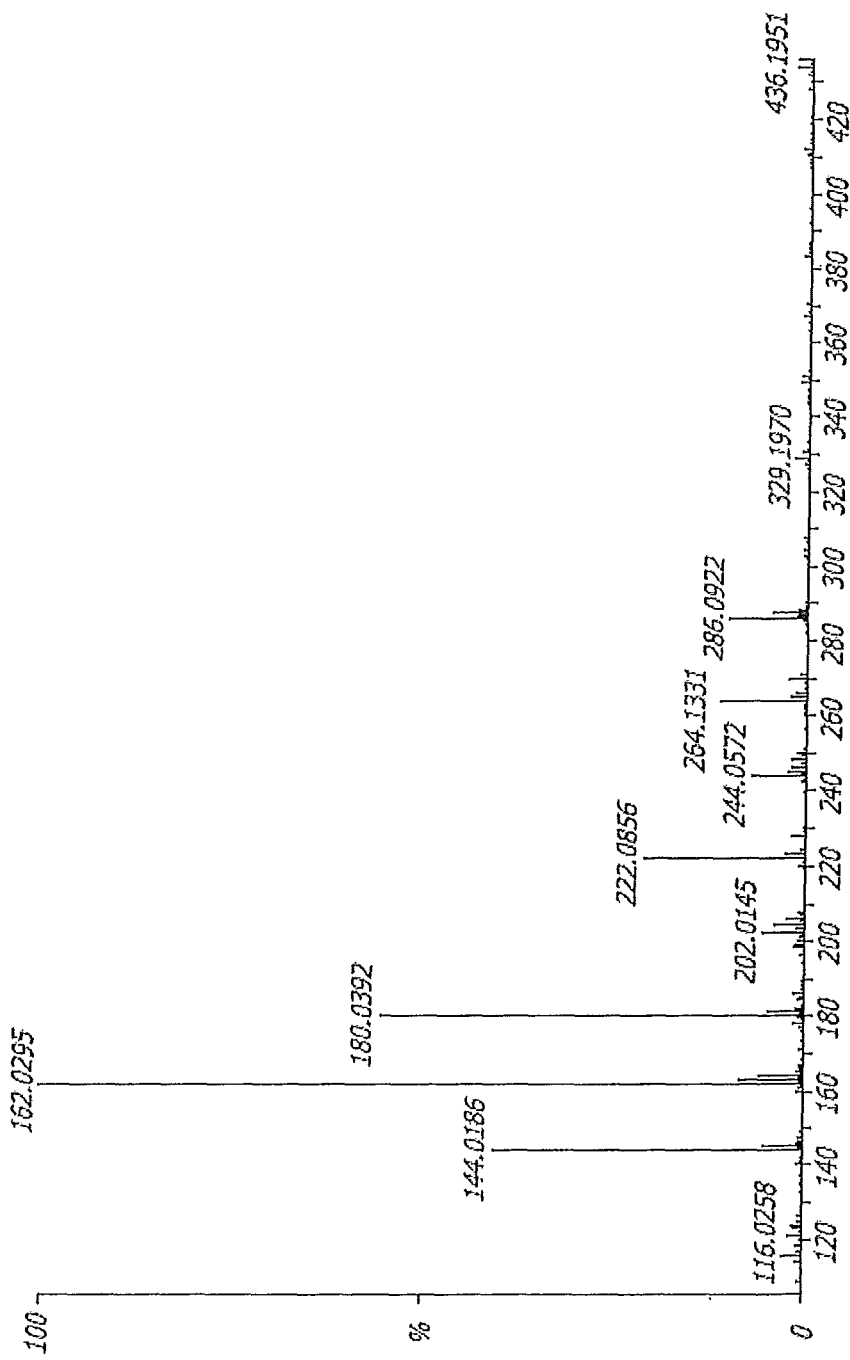
FIG. 8 illustrates a positive ion mode mass spectrum showing a parent peak and fragmentation pattern for DIPPMPO with m/z peaks at 264, 222, and 180.

Mass spectral data was collected in an attempt to determine the composition of the unidentified radical species. The mass spectrum shows a parent peak and fragmentation pattern for DIPPMPO with m/z peaks at 264, 222, and 180, as seen in FIG. 8. FIG. 8 also shows peaks for the DIPPMPO/Na adduct and subsequent fragments at 286, 244, and 202 m/z. Finally, FIG. 8 demonstrates peaks for one DIPPMPO/radical complex with m/z of 329. The negative ion mode mass spectrum also had a corresponding peak at m/z of 327. There are additional peaks at 349, 367, and 302 at a lower intensity as presented in FIG. 8. None of these peaks could be positively confirmed. However, there are possible structures that would result in these mass patterns. One possibility for the peak generated at 329 could be a structure formed from a radical combining with DIPPMPO. Possibilities of this radical species include a nitroxyl-peroxide radical (HNO—HOO.) that may have formed in the composition as a result of reaction with nitrogen from the air. Another peak at 349 could also be a result of a DIPPMPO/radical combination. Here, a possibility for the radical may be hypochlorite-peroxide (HOCl—HOO.). However, the small intensity of this peak and small intensity of the corresponding peak of 347 in the negative ion mode mass spectrum indicate this could be a very low concentration impurity and not a compound present in the ASEA composition.

ICP/MS Analysis

Samples were analyzed on an Agilent 7500 series inductively-coupled plasma mass spectrometer (ICP-MS) in order to confirm the hypochlorite concentration that was determined by NMR. A stock solution of 5% sodium hypochlorite was used to prepare a series of dilutions consisting of 300 ppb, 150 ppb, 75 ppb, 37.5 ppb, 18.75 ppb, 9.375 ppb, 4.6875 ppb, 2.34375 ppb, and 1.171875 ppb in deionized Milli-Q water. These standards were used to establish a standard curve.

Based on NMR hypochlorite concentration data, a series of dilutions was prepared consisting of 164.9835 ppb, 82.49175 ppb, 41.245875 ppb, 20.622937 ppb, 10.311468 ppb, and 5.155734 ppb. These theoretical values were then compared with the values determined by ICP-MS analysis. The instrument parameters were as follows:

| Elements analyzed | $^{35}Cl, ^{37}Cl$ |
| --- | --- |
| # of points per mass | 20 |
| # of repetitions | 5 |

-continued

| Elements analyzed | $^{35}Cl, ^{37}Cl$ |
|---|---|
| Total acquisition time | 68.8 s |
| Uptake speed | 0.50 rps |
| Uptake time | 33 s |
| Stabilization time | 40 s |
| Tune | No Gas |
| Nebulizer flow rate | 1 mL/min |
| Torch power | 1500 W |

The results of the ICP-MS analysis are as follows:

| Dilution | Measured Concentration (ppb) | Concentration by NMR (ppb) |
|---|---|---|
| 1 | 81 | 82 |
| 2 | 28 | 41 |
| 3 | 24 | 21 |
| 4 | 13 | 10 |
| 5 | 8 | 5 |

Dilutions were compared graphically to the ICP-MS signals and fit to a linear equation (R2=0.9522). Assuming linear behavior of the ICP-MS signal, the concentration of hypochlorite in the composition was measured to be 3.02 ppt. Concentration values were determined by calculating the concentration of dilutions of the initial composition and estimating the initial composition hypochlorite concentration to be 3 ppt (as determined from 35Cl NMR analysis). The ICP-MS data correlate well with the 35Cl NMR data, confirming a hypochlorite concentration of roughly ⅓% (3 ppt). It should be noted that ICP-MS analysis is capable of measuring total chlorine atom concentration in solution, but not specific chlorine species. The NMR data indicate that chlorine predominantly exists as ClO— in the composition.

Gas Phase Quadrupole MS

Sample Prep

Three sample groups were prepared in triplicate for the analysis: 1) Milli-Q deionized water 2) the composition, and 3) 5% sodium hypochlorite standard solution. The vials used were 20 mL headspace vials with magnetic crimp caps (GERSTEL). A small stir bar was placed in each vial (VWR) along with 10 mL of sample. The vials were capped, and then placed in a Branson model 5510 sonicator for one hour at 60° C.

The sonicator was set to degas which allowed for any dissolved gasses to be released from the sample into the headspace. After degassing, the samples were placed on a CTC PAL autosampler equipped with a heated agitator and headspace syringe. The agitator was set to 750 rpm and 95° C. and the syringe was set to 75° C. Each vial was placed in the agitator for 20 min prior to injection into the instrument. A headspace volume of 2.5 mL was collected from the vial and injected into the instrument.

Instrument Parameters

The instrument used was an Agilent 7890A GC system coupled to an Agilent 5975C EI/CI single quadrupole mass selective detector (MSD) set up for electron ionization. The GC oven was set to 40° C. with the front inlet and the transfer lines being set to 150° C. and 155° C. respectively. The carrier gas used was helium and it was set to a pressure of 15 PSI.

The MSD was set to single ion mode (SIM) in order to detect the following analytes:

| Analyte | Mass |
|---|---|
| Water | 18 |
| Nitrogen | 28 |
| Oxygen | 32 |
| Argon | 40 |
| Carbon Dioxide | 44 |
| Chlorine | 70 |
| Ozone | 48 |

The ionization source temperature was set to 230° C. and the quadrupole temperature was set to 150° C. The electron energy was set to 15 V.

Mass spectrometry data was obtained from analysis of the gas phase headspace of the water, the composition, and hypochlorite solution. The raw area counts obtained from the mass spectrometer were normalized to the area counts of nitrogen in order to eliminate any systematic instrument variation. Both nitrogen and water were used as standards because they were present in equal volumes in the vial with nitrogen occupying the headspace and water being the solvent. It was assumed that the overall volume of water and nitrogen would be the same for each sample after degassing. In order for this assumption to be correct, the ratio of nitrogen to water should be the same for each sample. A cutoff value for the percent relative standard deviation (% RSD) of 5% was used. Across all nine samples, a % RSD of 4.2 was observed. Of note, sample NaClO-3 appears to be an outlier, thus, when removed, the % RSD drops to 3.4%.

Figure 9:
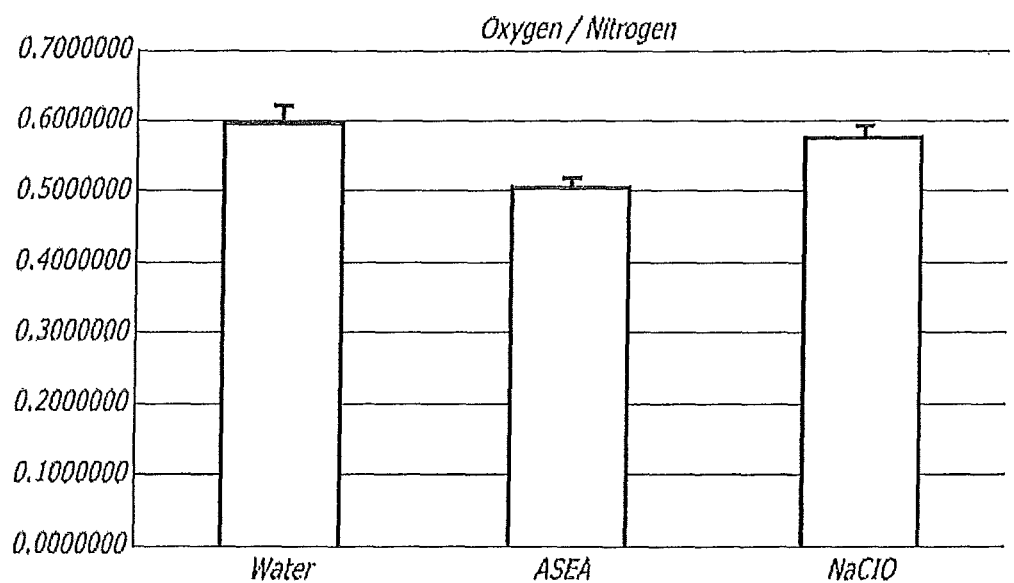
FIG. 9 illustrates oxygen/nitrogen ratios for a composition described herein compared to water and NaClO (the composition is labeled "ASEA").
Figure 10:
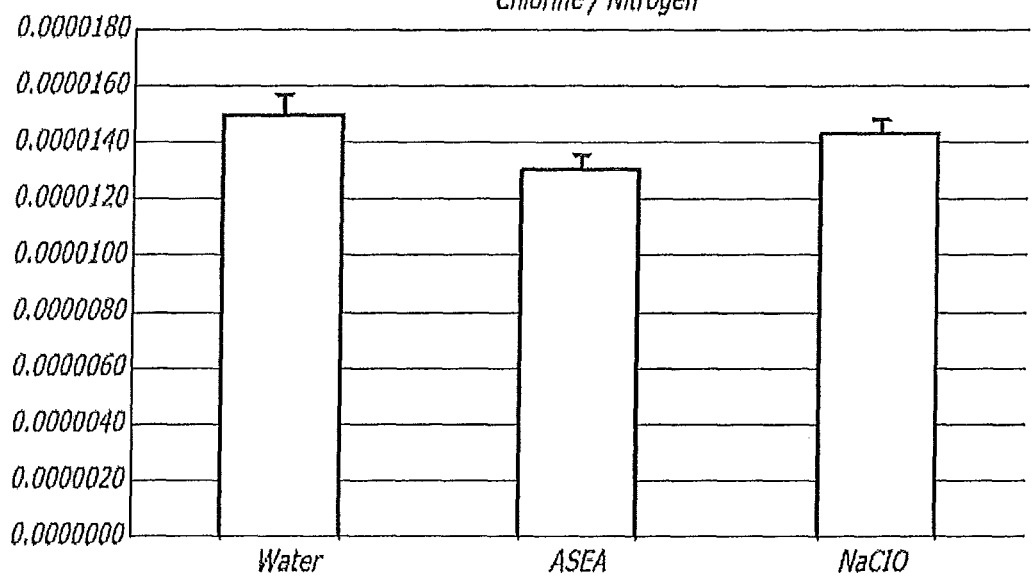
FIG. 10 illustrates chlorine/nitrogen ratios for a composition described herein compared to water and NaClO (the composition is labeled "ASEA").

FIGS. 9-11 illustrate oxygen/nitrogen, chlorine/nitrogen, and ozone/nitrogen ratios. It appears that there were less of these gases released from the composition than from either water or nitrogen. It should be noted that the signals for both ozone and chlorine were very weak. Thus, there is a possibility that these signals may be due to instrument noise and not from the target analytes.

FIG. 12 illustrates the carbon dioxide to nitrogen ratio. It appears that there may have been more carbon dioxide released from the composition than oxygen. However, it is possible that this may be due to background contamination from the atmosphere.

Based on the above, more oxygen was released from both water and sodium hypochlorite than the composition.

EPR

Two different composition samples were prepared for EPR analysis. The composition with nothing added was one sample. The other sample was prepared by adding 31 mg of DIPPMPO to 20 mL of the composition (5.9 mM), vortexing, and placing the sample in a 4° C. refrigerator overnight. Both samples were placed in a small capillary tube which was then inserted into a normal 5 mm EPR tube for analysis.

EPR experiments were performed on a Bruker EMX 10/12 EPR spectrometer. EPR experiments were performed at 9.8 GHz with a centerfield position of 3500 Gauss and a sweepwidth of 100 Gauss. A 20 mW energy pulse was used with modulation frequency of 100 kHz and modulation amplitude of 1 G. Experiments used 100 scans. All experiments were performed at room temperature.

Figure 13:
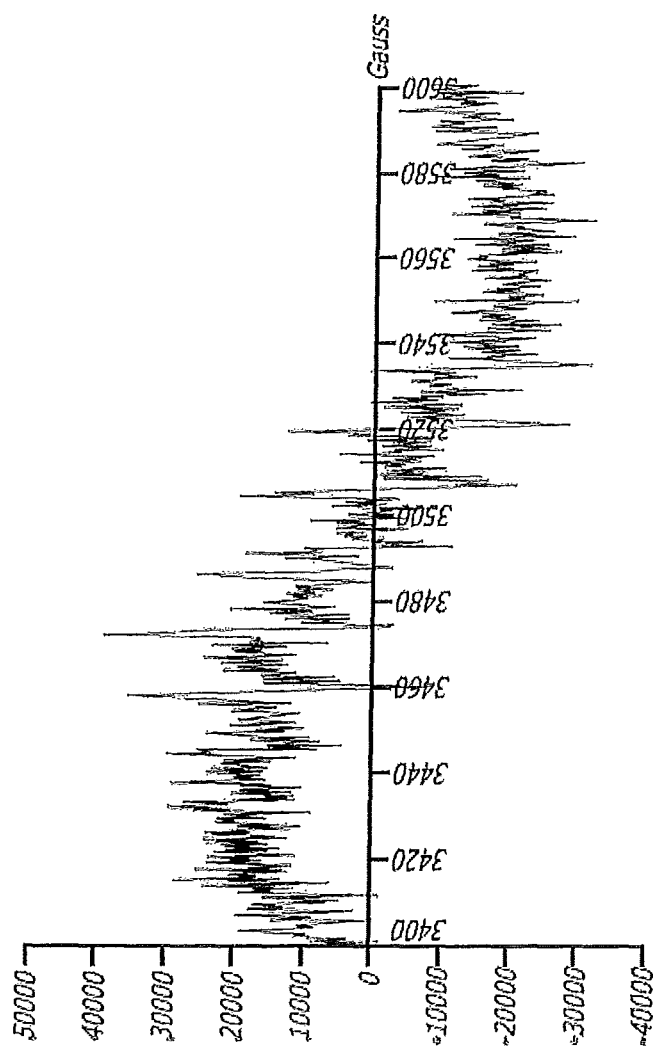
FIG. 13 illustrates an EPR splitting pattern of DIPPMOP/ASEA mixture (the composition in a certain embodiment is "ASEA").

EPR analysis was performed on the composition with and without DIPPMPO mixed into the solution. FIG. 13 shows the EPR spectrum generated from DIPPMPO mixed with the composition. The composition alone showed no EPR signal after 100 scans (not presented). FIG. 13 illustrates an EPR splitting pattern for a free electron. This electron appears to be split by three different nuclei. The data indicate that this is a characteristic splitting pattern of OH. radical interacting with DMPO (similar to DIPPMPO). This pattern can be described by 14N splitting the peak into three equal peaks and 1H three bonds away splitting that pattern into two equal triplets. If these splittings are the same, it leads to a quartet splitting where the two middle peaks are twice as large as the outer peaks. This pattern may be seen in FIG. 13 twice, with the larger peaks at 3457 and 3471 for one quartet and 3504 and 3518 for the other quartet. In this case, the 14N splitting and the 1H splitting are both roughly 14G, similar to an OH* radical attaching to DMPO. The two quartet patterns in FIG. 13 are created by an additional splitting of 47G. This splitting is most likely from coupling to 31P, and similar patterns have been seen previously. The EPR spectrum in FIG. 13 indicates that there is a DIPPMPO/OH. radical species in the solution.

Example 3

This example describes a process and system for producing a redox signaling composition comprising redox signaling agents according to the present description. Electrolyzed fluid can be made in different types of vessels as long as the proper power sourced is used. One example of an apparatus that was used to make electrolyzed solution for treating fungal infections is that referred to in FIGS. 14-18.

Referring first to FIG. 14, which is a perspective view of a first presently preferred embodiment of the present invention generally represented at 100, includes a power supply 102 and a fluid receptacle represented at 104. The fluid receptacle 104 includes a base 114 upon which is attached a fluid vessel 116. The base 114 can preferably be fabricated from an insulative plastic material. The fluid vessel 116 is preferably fabricated from an inert clear plastic material which is compatible with biological processes as available in the art.

A lid 118 is provided to cover the fluid vessel 116 and keep contaminants out of the fluid vessel 116. A screen 120 is positioned to prevent foreign objects, which might accidentally fall into the fluid vessel 116, from falling to the bottom of the fluid vessel 116. The saline solution which is to be treated is placed into the fluid vessel 116, and the lid 118 placed, for the necessary period of time after which the electrolyzed saline solution can be withdrawn from the fluid vessel 116, for example into a syringe, for use. The fluid vessel 116 is sealed at its bottom by a floor 124 which is attached to the interior of the base 114.

An electrode assembly, generally represented at 122, is attached to the floor 124 so that any fluid in the fluid vessel is exposed to the electrode assembly 122. The electrode assembly 122 is electrically connected to the power supply 102 via terminals 110 and 112 and cables 106 and 108, respectively. The power supply 102 should deliver a controlled voltage and current to the electrode assembly 122 when fluid is placed into the fluid vessel 116. The voltage and current applied to the electrode assembly 122 will vary according to the fluid being electrolyzed. A control for setting and measuring the voltage 102A and a control for setting and measuring the current 102B is provided in the power supply. In accordance with the present invention, a low voltage of less than about 30 volts DC is used. Exemplary voltage and current values, and the advantages which accrue when using the preferred voltage and current values, will be explained shortly.

FIG. 15 is a top view of the electrode assembly 122 represented in FIG. 14. The electrode assembly 122 preferably comprises a cylindrical inner electrode 128 and a cylindrical outer electrode 126. The inner electrode 128 is preferably solid or any hollow in the inner electrode is sealed so that fluid does not enter any such hollow. The cylindrical shape of the inner electrode 128 and the outer electrode 126 is preferred and results in better performance than obtained with electrodes of other shapes, e.g., elongated flat panels.

The diameter A of the inner electrode 128 is preferably about one-half inch but the diameter A of the inner electrode can be selected by those skilled in the art in accordance with the particular application for the electrode using the information contained herein. The outer electrode 126 should be of a generally cylindrical shape and preferably be fabricated from titanium or niobium having a thickness (indicated at B in FIG. 15) which ensures that the inner electrode is shielded from potentially physical damage. As will be appreciated, titanium and niobium provide the advantage of resistance against corrosion which further prevents the introduction of harmful substances into the fluid being electrolyzed.

Still referring to FIG. 15, the space, indicated at C, between the inner electrode 128 and the outer electrode 126 does not exceed a maximum value. In contrast to previously available devices which separate the electrodes by greater distances and then utilize higher voltages to obtain the desired electrolyzation, the present invention keeps the electrode spacing small and obtains improved performance over other schemes. It is preferred that the space between the inner electrode 128 and the outer electrode 126 be not more than about one-half (½) inch; it is more preferred that the space between the inner electrode 128 and the outer electrode 126 be not more than about three-eights (⅜) inch; and, it is most preferred that the space between the inner electrode 128 and the outer electrode 126 be not more than about one-quarter (¼) inch.

Reference will next be made to FIG. 15A which is a side cross sectional view of the electrode assembly taken along line 3-3 in FIG. 15. As seen in FIG. 15A, the outer electrode 126 extends above the inner electrode 128 to provide improved electrical performance and physical protection. The outer electrode 126 is attached to the floor 124 by way of bolts 130, which extend through bores provided in the floor 124, and accompanying nuts. An electrical connection is made to the outer electrode 126 by a lead 136 attached to the bolt and nut. The lead 136 is attached to one of the terminals 110 or 112. Similarly, an electrical connection is made to the inner electrode 128 by a lead 134 which is held in place by a nut attached to a threaded stud extending from the bottom of the inner electrode and through a bore provided in the floor 124. The lead 134 is attached to the remaining one of the terminals 110 or 112. The leads 134 and 136 are kept insulated from any fluid which is present in the fluid vessel 116.

It is preferred that the inner electrode 128 function as the anode while the outer electrode function as the cathode when electrolyzing fluids and the power supply 102 and the terminals 110 and 112 should be properly arranged to carry this out.

It is recognized in the art that the anode is subject to destructive forces during electrolysis. In the prior art, the anode of an electrode assembly may dissolve to the point of being inoperative and may need to be replaced very often. Critically, as the anode of an electrode assembly dissolves, the metallic components of the anode are dispersed into the fluid. If the fluid is a saline solution which will be used to treat physiological fluids, toxic substances dispersed into the solution, such as the materials comprising the anode, may be harmful or dangerous to the person who expects to be benefited from the treatment.

Of all the possible materials for fabrication of the anode, the art recognizes that platinum is the least likely to be dissolved when used as an anode. Unfortunately, the cost of platinum precludes the use of an anode which consists entirely of platinum. Thus, it is common in the art to utilize another metal as a base for the anode with a layer of platinum being placed on surfaces which contact the fluid to be electrolyzed.

The present invention advantageously utilizes an inner electrode 128, i.e., an anode, which includes a base of titanium, and even more preferably niobium (also known as columbium), upon which a layer of platinum is provided wherever fluid contacts the anode. Significantly, niobium is a relatively good electrical conductor having a conductivity which is about three times greater than the conductivity of titanium. Moreover, if the base metal is exposed to the fluid, such as if a pinhole defect develops, toxic products are not produced by the contact between niobium and the fluid. Moreover, the high breakdown voltage in saline solution of the oxide which forms when a niobium base receives a layer of platinum provides further advantages of the present invention.

Upon a base of niobium, a layer of platinum is formed on the anode. The layer of platinum is preferably formed using a technique referred to in the art as brush electrodeposition which can be carried out by those skilled in the art using the information set forth herein. Other techniques can also be used to form the platinum layer, such as tank (immersion) electrodeposition, vapor deposition, and roll bonding, but brush electrodeposition is preferred because of its superior adhesion and resulting less porosity than other economically comparable techniques.

The thickness of the platinum layer is preferably greater than about 0.02 mils and is most preferably greater than about 0.06 mils, and up to about 0.20 mils. The combination of using niobium as a base for the anode of the electrode assembly and utilizing brush electrodeposition provides that the platinum layer can be much thinner than otherwise possible and still provide economical and reliable operation. It will be appreciated by those skilled in the art, that even with an anode fabricated in accordance with the present invention replacement of the anode, which preferably comprises the inner electrode 128 represented in FIG. 15A, may be necessary after a period of use. The construction of the embodiments of the present invention facilitate replacement of the inner electrode 128 and the outer electrode 126 when it becomes necessary.

Represented in FIG. 16 is a block diagram of a second presently preferred embodiment, generally represented at 150, of the present invention. The embodiment represented in FIG. 16 is particularly adapted for treating large quantities of saline solution. Represented in FIG. 16 is a tank 152 in which the saline solution is electrolyzed. An electrode assembly 154 is provided in the tank and is preferably immersed into the solution. A power supply 158, capable of providing sufficient current at the proper voltage, is connected to the electrode assembly via a cable 160.

Also represented in FIG. 16 is a circulation device 156 which optionally functions to circulate the solution within the tank 152. A sensor 162 is also optionally provided to measure the progress of the electrolyzation of the solution in the tank 152, for example by measuring the pH of the solution. The sensor may preferably be an ion selective electrode which can be chosen from those available in the art. Other sensors, for example chlorine, ozone, and temperature sensors, may also be included within the scope of the present invention. A control unit 164 is optionally provided to coordinate the operation of the power supply 158, the circulation device 156, and the sensor 162 in order to obtain the most efficient operation of the apparatus 150.

It will be appreciated that devices such as power supply 158, circulation device 158, sensor 162, and control unit 164 can be readily obtained from sources in the industry and adapted for use with embodiments of the present invention by those skilled in the art using the information contained herein. In particular, the control unit 164 is preferably a digital microprocessor based device accompanied by appropriate interfaces all allowing for accurate control of the operation of the apparatus 150. It is also within the scope of the present invention to include structures to prevent contamination of the treated solution by contact with nonsterile surfaces and by airborne pathogens both during treatment and while the fluid is being transferred to the apparatus and being withdrawn from the apparatus.

Figure 17:
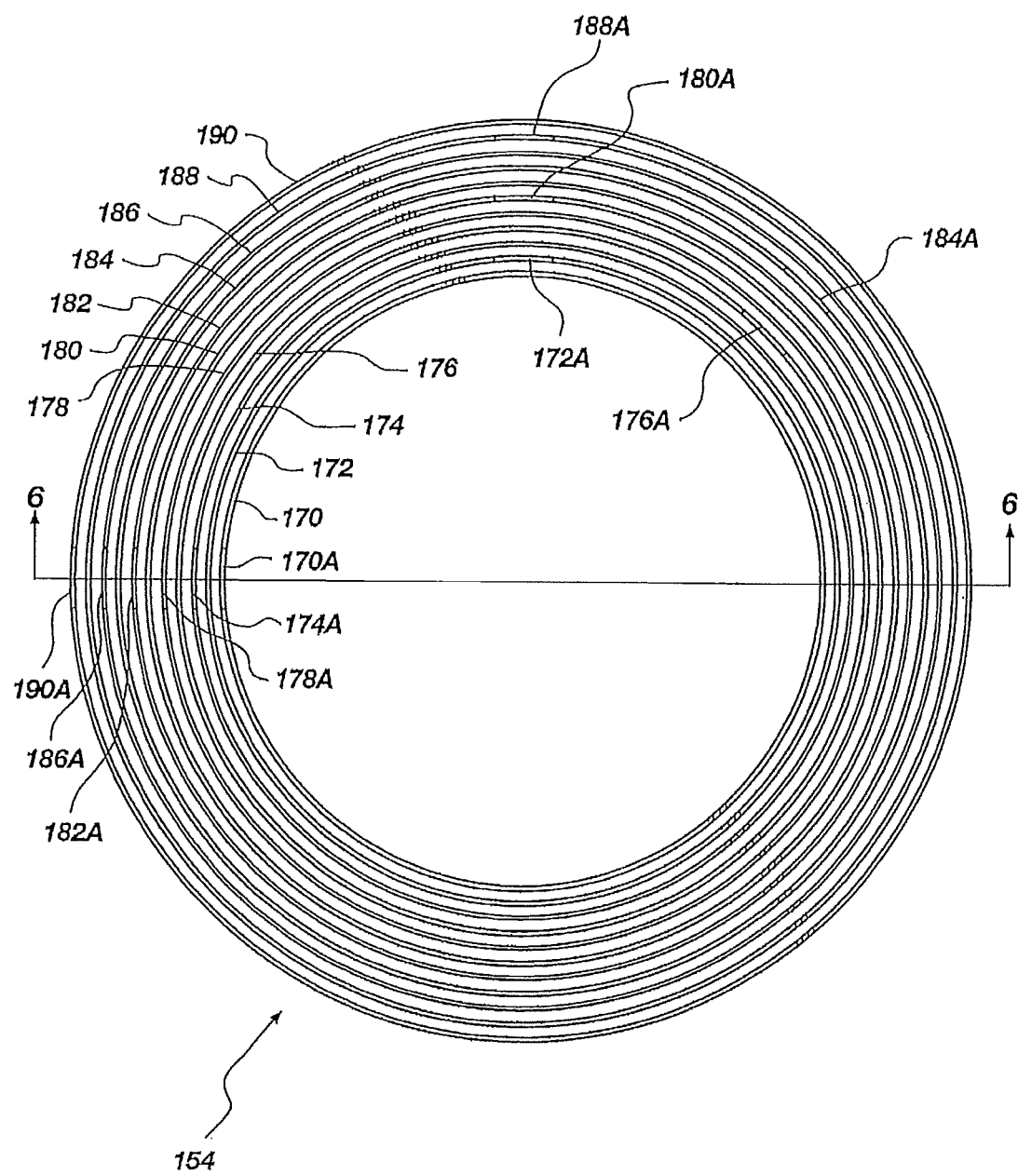
FIG. 17 is a top view of an electrode assembly preferred for use in the apparatus represented in FIG. 16.
Figure 18:
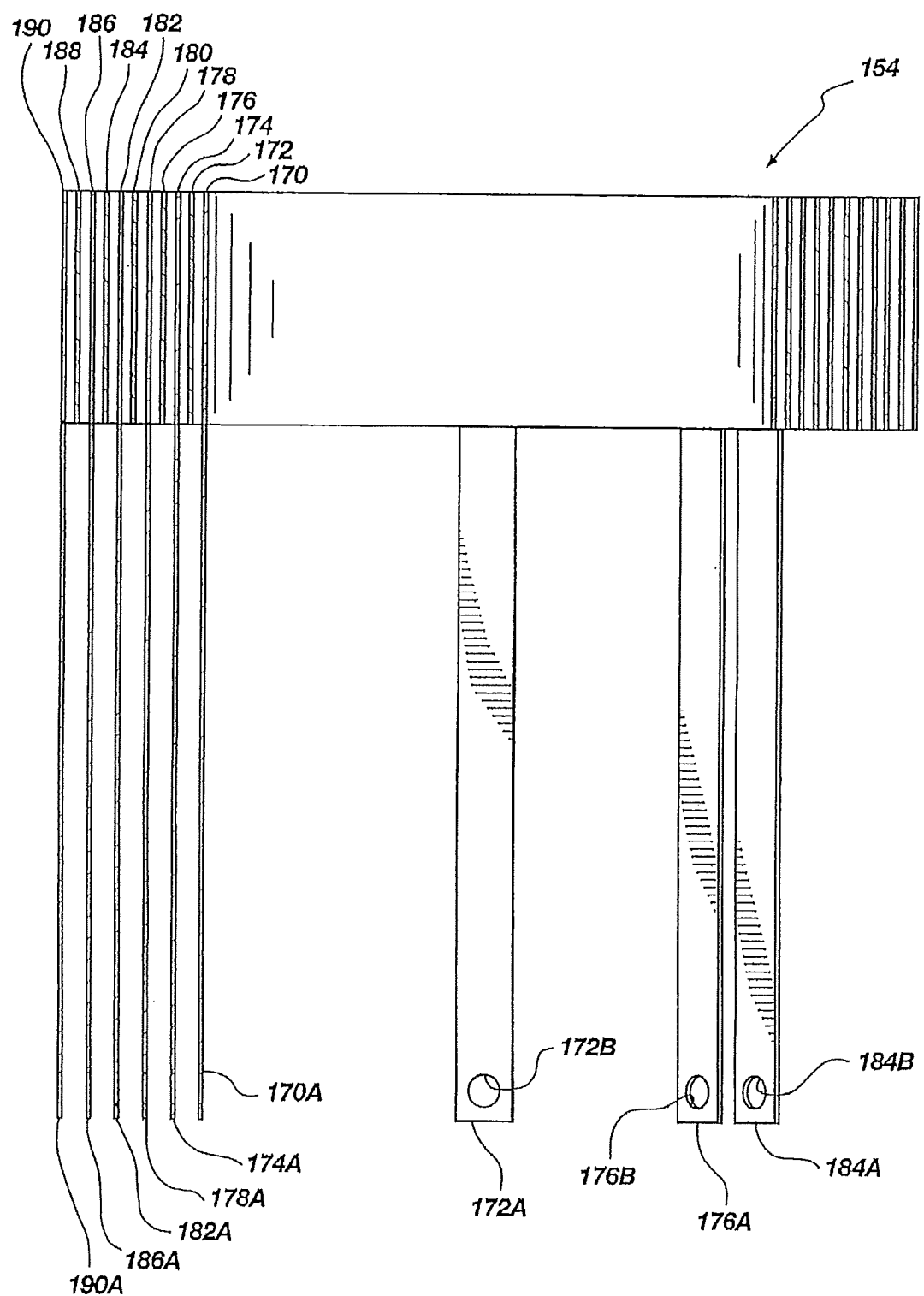
FIG. 18 is a cross sectional view taken along line 6-6 of FIG. 17.

Reference will next be made to FIGS. 17 and 18 which are a top view and cross sectional view, respectively, of an electrode assembly, generally represented at 154, which is preferred for use in the apparatus represented in FIG. 16. As can be seen best in FIG. 17, the electrode assembly 154 includes a plurality of concentrically arranged anodes and cathodes. The cylindrical shape and concentric arrangement of the electrodes represented in FIG. 17 provides for the most efficient operation. The number of electrodes which are included can be selected according to the application of the apparatus. For example, the number of electrodes may be six, seven, eight, the eleven represented in FIGS. 17 and 18, or more.

In FIG. 17, electrodes 170, 174, 178, 182, 186, and 190 preferably function as cathodes and are preferably fabricated in accordance with the principles set forth above in connection with the outer electrode represented at 126 in FIGS. 14-15A. Furthermore, in FIG. 17 electrodes 172, 176, 180, 184, and 188 function as anodes and are preferably fabricated in accordance with the principles set forth above in connection with the inner electrode represented at 128 in FIGS. 14-15A.

In the cross sectional side view of FIG. 18 a plurality of tabs extend from the cylindrical electrodes 170, 172, 174, 176, 178, 180, 182, 184, 186, and 190 to facilitate making an electrical connection thereto. Provided below in the following Table are the relationship between the tabs illustrated in FIG. 18 and the electrodes.

| Relationship between the tabs illustrated in FIG. 18 | | |
| --- | --- | --- |
| Electrode | Tab | Function |
| 170 | 170A | Cathode |
| 172 | 172A | Anode |
| 174 | 174A | Cathode |
| 176 | 176A | Anode |
| 178 | 178A | Cathode |
| 180 | 180A (Not illustrated in FIG. 18) | Anode |
| 182 | 182A | Cathode |
| 184 | 184A | Anode |
| 186 | 186A | Cathode |
| 188 | 188A | Anode |
| 190 | 190A (Not illustrated in FIG. 18) | Cathode |

Using the tabs 170A, 172A, 174A, 176A, 178A, 180A, 182A, 184A, 186A, 188A, and 190A, those skilled in the art can provide the necessary electrical connections to the electrodes 170, 172, 174, 176, 178, 180, 182, 184, 186, and 190 and can also provide numerous structures to prevent contact between the tabs and the fluid to be treated. Each of the tabs illustrated in FIG. 18 are provided with an aperture, such as those represented at 172B, 176B, and 184B, which receive a wiring connector.

While the apparatus described in Example 3 herein has many uses, the most preferred use of the apparatus described herein is subjecting sterile saline solution to electrolysis. The electrolyzed saline solution can then be used to treat a patient. The saline solution preferably has an initial concentration in the range from about 0.25% to about 1.0% NaCl which is about one-fourth to full strength of normal or isotonic saline solution. According to Taber's Cyclopedic Medical Dictionary, E. A. Davis, Co. 1985 Ed., an "isotonic saline" is defined as a 0.16 M NaCl solution or one containing approximately 0.95% NaCl; a "physiological salt solution" is defined as a sterile solution containing 0.85% NaCl and is considered isotonic to body fluids and a "normal saline solution;" a 0.9% NaCl solution which is considered isotonic to the body. Therefore, the terms "isotonic," "normal saline," "balanced saline," or "physiological fluid" are considered to be a saline solution containing in the range from about 0.85% to about 0.95% NaCl. Moreover, in accordance with the present invention, a saline solution may be subjected to electrolysis at concentrations in the range from about 0.15% to about 1.0%.

It is preferred that one of the above described saline solutions be diluted with sterile distilled water to the desired concentration, preferably in the range from about 0.15% to about 0.35% prior to treatment in accordance with the present invention. This dilute saline solution is subjected to electrolysis using the embodiments of the present invention at a voltage, current, and time to produce an appropriately electrolyzed solution as will be described shortly. It is presently preferred to carry out the electrolysis reaction at ambient temperatures. In a more preferred embodiment the saline solution used with the apparatus of Example 3 is 9.1 g NaCl/1 L of water. In another preferred embodiment the saline solution used with the apparatus of Example 3 is 2.8 gNaCl/1 L of water.

The voltage and current values provided herein are merely exemplary and the voltage and current values which are used, and the time the saline solution is subject to electrolysis, is determined by many variables, e.g., the surface area and efficiency of the particular electrode assembly and the volume and/or concentration of saline solution being electrolyzed. For electrode assemblies having a different surface area, greater volumes of saline solution, or higher concentrations of saline solutions the voltage, current, or time may be higher and/or longer than those exemplary values provided herein. In accordance with the present invention, it is the generation of the desired concentration of ozone and active chlorine species which is important. Electrolyzation of the saline solution also results in other products of the electrolysis reaction including members selected from the group consisting of hydrogen, sodium and hydroxide ions. It will be appreciated that the interaction of the electrolysis products results in a solution containing bioactive atoms, radicals or ions selected from the group consisting of chlorine, ozone, hydroxide, hypochlorous acid, hypochlorite, peroxide, oxygen and perhaps others along with corresponding amounts of molecular hydrogen and sodium and hydrogen ions.

In order to arrive at the preferred end product, electrolyzed saline solution using the apparatus illustrated in FIGS. 14-15A, about a 0.33% (about one third physiologically normal) saline solution is placed in the fluid vessel 116 (FIG. 14) and the apparatus is operated for about 5 to 15 minutes with a voltage between the electrodes being maintained in the range from about 10 volts to about 20 volts with a current flow maintained in the range from about 5 to about 20 amps.

In one example, the cell described in Example 3 operated for 1 hour at 40 C using 3 Amps with a saline solution of less than 0.35% saline.

In one example, the cell described in Example 3 operated for 1 hour at 40 C using 3 Amps with a saline solution of less than 1.0% saline.

In one example, the cell described in Example 3 operated for 3 minutes at 23 C using 3 Amps with a saline solution of less than 0.35% saline.

In one example, the cell described in Example 3 operated for 3 minutes at 23 C using 3 Amps with a saline solution of less than 1.0% saline.

As one example of the use of the embodiment of FIGS. 14-15A, a 0.225% saline solution is subjected to a current of 3 amperes at 20 volts (DC) for a period of three minutes. A 17 ml portion of this electrolyzed solution is aseptically diluted with 3 mls of a sterile 5% saline resulting in a finished isotonic electrolyzed saline having an active ozone content of 12.+−.2 mg/L and an active chlorine species content of 60.+−.4 ppm at a pH of 7.4.

It will be appreciated that the low voltages used in accordance with the present invention are preferably not greater than forty (40) volts DC or an equivalent value if other than direct current is used. More preferably, the voltages used in accordance with the present invention is not more than about thirty (30) volts DC. The use of low voltages avoids the problem of production of undesirable products in the fluid which can result when higher voltages are used. In accordance with the present invention, the close spacing of the electrodes facilitates the use of low voltages.

In another example, to show that the embodiment of FIGS. 14-15 can be used to effectively carry out electrolysis in saline solutions up to about 1% in concentration, the electrolysis reaction is carried out at saline concentrations of 0.3, 0.6 and 0.9%, respectively. The active chlorine species $Cl_2$ and ozone $O_3$ contents were measured and are provided in the table below:

| $Cl_2$ and $O_3$ Content from Salines at Varying Concentrations | | |
|---|---|---|
| Saline Concentration (% NaCl) | $Cl_2$ Concentration (ppm) | $O_3$ Concentration (mg/mL) |
| 0.3 | 129 | 21.8 |
| 0.6 | 161 | 26.6 |
| 0.9 | 168 | 28.0 |

As can be seen from the above table, the resulting electrolyzed saline solution includes active components which are within the parameters required for effective treatment.

It will be appreciated that the features of the present invention, including the close electrode spacing, the low voltages used, and the materials used to fabricate the electrodes, result in an apparatus which provides unexpectedly better results than the previously available devices and schemes.

Example 4

A saline solution was made with the apparatus of Example 3 wherein the solution was electrolyzed for 3 min at 3 amps and such that the solution being electrolyzed had 9.1 g NaCl/L of purified water. The product made accordingly is called RXN-1. The RXN-1 product was tested for superoxides and hypochlorites as described herein. Specifically, the presence of superoxides was tested with the Nanodrop 3300 and R-phycoerytherin (R-PE) as the reagent and the presence of hypochlorites was tested with the Nanodrop 3300 and aminophenyl fluorescein (APF) as the reagent. The tests revealed the presence of both superoxides as well as hypochlorites. The superoxides were tested as an amount relative to the amount of superoxides that are present in a sample made according to Example 1. That is, superoxides were tested as an amount relative to the amount of superoxides when a total of 1,000 gallons of salinated water was electrolyzed with a total of 56 amps running through the electrodes and further wherein the electrolyzing occurred at 4.5-5.8° C. The amount of superoxides present in the RXN-1 product was 130% of the amount of superoxides present in a sample made according to Example 1. Similarly, the hypochlorites were tested as an amount relative to the amount of hypochlorites that are present in a sample made according to Example 1. That is, hypochlorites were tested as an amount relative to the amount of hypochlorites when a total of 1,000 gallons of salinated water was electrolyzed with a total of 56 amps running through the electrodes and further wherein the electrolyzing occurred at 4.5-5.8° C. The amount of hypochlorites present in the RXN-1 product was 82% of the amount of hypochlorites present in a sample made according to Example 1.

Example 5

A saline solution was made with the apparatus of Example 3 wherein the solution was electrolyzed for 3 min at 3 amps and such that the solution being electrolyzed had 2.8 g NaCl/L of purified water. The product made accordingly is called RXN-2. The RXN-2 product was tested for superoxides and hypochlorites as described herein. Specifically, the presence of superoxides was tested with the Nanodrop 3300 and R-phycoerytherin (R-PE) as the reagent and the presence of hypochlorites was tested with the Nanodrop 3300 and aminophenyl fluorescein (APF) as the reagent. The tests revealed the presence of both superoxides as well as hypochlorites. The superoxides were tested as an amount relative to the amount of superoxides that are present in a sample made according to Example 1. That is, superoxides were tested as an amount relative to the amount of superoxides when a total of 1,000 gallons of salinated water was electrolyzed with a total of 56 amps running through the electrodes and further wherein the electrolyzing occurred at 4.5-5.8° C. The amount of superoxides present in the RXN-2 product was 120% of the amount of superoxides present in a sample made according to Example 1. Similarly, the hypochlorites were tested as an amount relative to the amount of hypochlorites that are present in a sample made according to Example 1. That is, hypochlorites were tested as an amount relative to the amount of hypochlorites when a total of 1,000 gallons of salinated water was electrolyzed with a total of 56 amps running through the electrodes and further wherein the electrolyzing occurred at 4.5-5.8° C. The amount of hypochlorites present in the RXN-2 product was 80% of the amount of hypochlorites present in a sample made according to Example 1.

Power Sources

As described in detail above, a DC (direct current) is used to electrolyze water. To prepare a direct current for electrolyzation, readily available electricity, such as that which comes from a wall socket, is brought to a terminal strip. This terminal strip, also known as a terminal block, acts like a surge protector allowing a number of electrical connections from the strip to other devices. For example, the terminal strip can be an interface for electrical circuits. The terminal strip can be connected to a ground and/or a current transformer. A transformer can be used to measure electric currents. The terminal strip can also be connected to a potentiometer. The potentiometer measures voltage across an electrical system and can be used to aid in adjusting the voltage. For example a dial can be connected to the potentiometer so that the operator may adjust the voltage as desired.

Another transformer can be connected to the potentiometer, which can then be operably connected to a rectifier. Rectifiers in general convert alternating current (AC) to direct current (DC). One specific type of rectifier which suits the invention well is a bridge rectifier. Converting the waveform into one with a constant polarity increases the voltage output. This waveform is called a full wave rectified signal. Once the waveform and voltage are configured as desired, the DC shunt can provide a means for bringing electricity to different devices such as the electrodes, monitors and other operational instruments.

Figure 19:
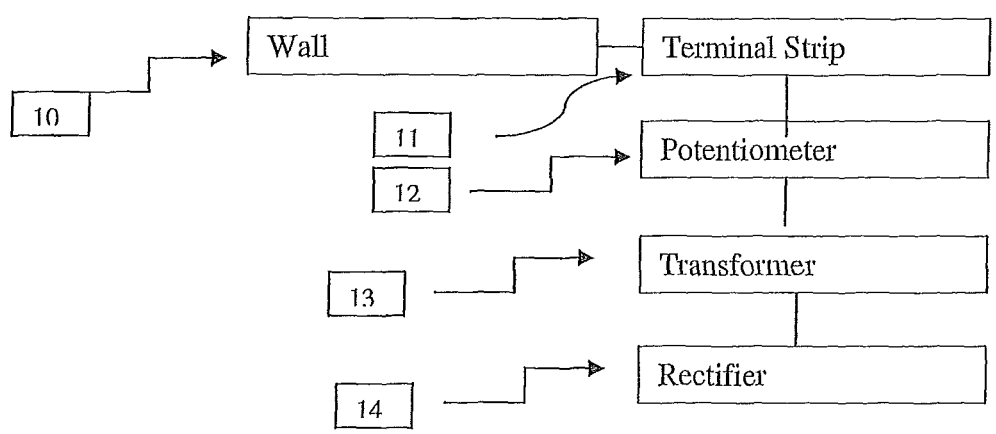
FIG. 19 Illustrates a block diagram of a power source.

FIG. 19 diagrams an example of a power source which can be used in the invention. Electricity comes in from the wall 10 and is met by a terminal strip 11. Terminal strip 11 is in operable communication with a potentiometer 12, and a current transformer 13. Potentiometer 12 is in operable communication with the transformer 13. The transformer 13 is in operable communication with a rectifier 14.

Figure 20:
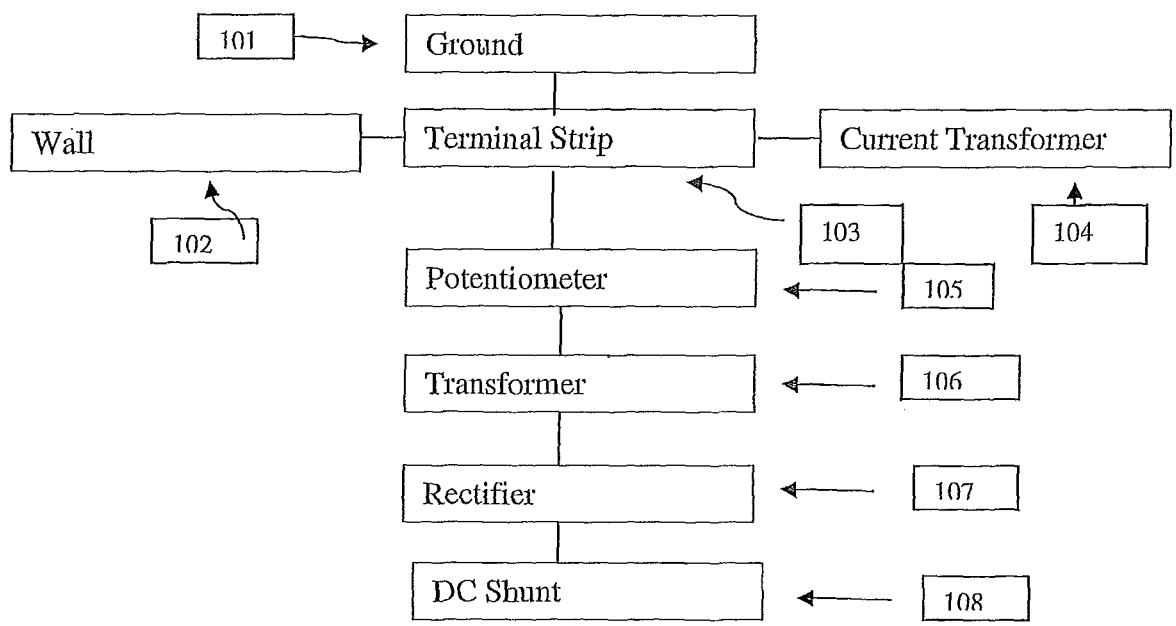
FIG. 20 Illustrates a block diagram of another power source.
Figure 21:
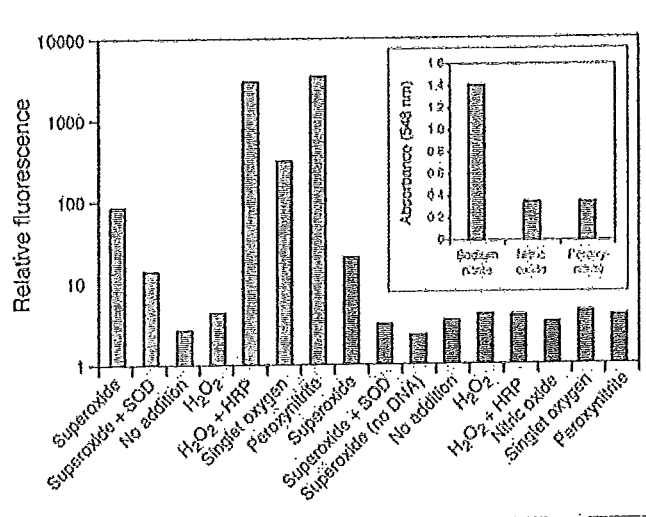
FIG. 21 is a chart of the relative fluorescence of various compositions.

FIG. 20 diagrams an example of a power source which can be used in the invention. Electricity comes in from the wall 102 and is met by a terminal strip 103. Terminal strip 103 is in operable communication with a potentiometer 105, a grounding means 101 and a current transformer 104. Potentiometer 105 is in operable communication with the transformer 106. The transformer 106 is in operable communication with a rectifier 107. Rectifier 107 is in operable communication with a DC shunt 108.

Determination of ROS Levels Against a Known Standard

The measurement of concentrations of ROS, particularly a superoxide, inside the solutions has been done by means of a fluoro spectrometer, Nanodrop 3300, and three varieties of fluorescent dyes, R-Phycoerytherin (R-PE), Hydroxyphenyl fluorescein (HPF) and Aminophenyl fluorescein (APF), that are commonly used to determine relative ROS concentrations inside active biological systems and cells. The molecules in these dyes change shape, and therefore fluoresce only when exposed to molecular components in ROS. The resulting change in fluorescence can then be detected by the fluoro spectrometer and can be related to the concentration of ROS present. ROS concentrations in electrolyzed saline solutions (ESS) solutions are verified and detected by either APF or R-PE fluorescent dyes, both of which produce entirely consistent measurements of relative concentrations of ROS in various concentrations and dilutions of ESS solutions. ROS measurements in ESS solutions have been linked using R-PE fluorescent dye, to the reaction of this dye to regulated concentrations of 2/2'-Axobis(2-methylpropionamide)dihidrochloride, a molecule that produces known amounts of ROS. This is not an absolute measurement, but it relates ROS in ESS to amounts of a known producer of ROS.

These fluorescent dyes are often used in combination with a fluorescence microscope to create high-resolution images of the build-up of ROS (oxidative stress) inside individual living cells. These dyes have been shown to specifically be sensitive to concentrations of ROS regardless of complex surrounding chemical environments.

Although APF and R-PE dyes are capable of measuring relative ROS concentrations in ESS solutions, no known absolute standard concentration for stabilized ROS in pure saline solutions exists. Furthermore, discrepancies in the decay time of these fluorescent dyes make measuring standardized amounts of ROS in other solutions incompatible with measuring those found in ESS. This may be due, in part, to the molecular complexes in ESS solutions that keep the ROS concentration stable, effectively shielding the free radicals from readily reacting with the dyes. The standard for ROS concentration in ESS solutions is therefore measured relative to the ROS concentration in a standardized solution that has been used in all of the antimicrobial and toxicity studies to date, both published and unpublished. Methods to measure absolute ROS concentrations in ESS solutions are actively being pursued.

The regulated amounts of ROS, thus measured, inside a variety of the ESS solutions produced by various embodiments of this invention have been shown to be stable, consistent and predictable, sufficient for therapeutic applications.

The development of a phycobiliprotein fluorescence quenching assay for the routine determination of ROS content in ASEA has been successful and is used routinely to monitor production quality for ROS levels. The assay has the following characteristics: ease of use, sensitivity, and quantitation. The assay is linear over a 2 log 10 range of ROS concentrations. For a compositions comprising RXNs, the starting saline was used as a negative control, AAPH (2,2'-Azobis (2-amidinopropane) dihydrochloride which is a standard ROS generating compound) served as a positive control and allowed the generation of a standard curve, and the compositions comprising RXNs or other samples comprised the unknowns.

Figure 24:
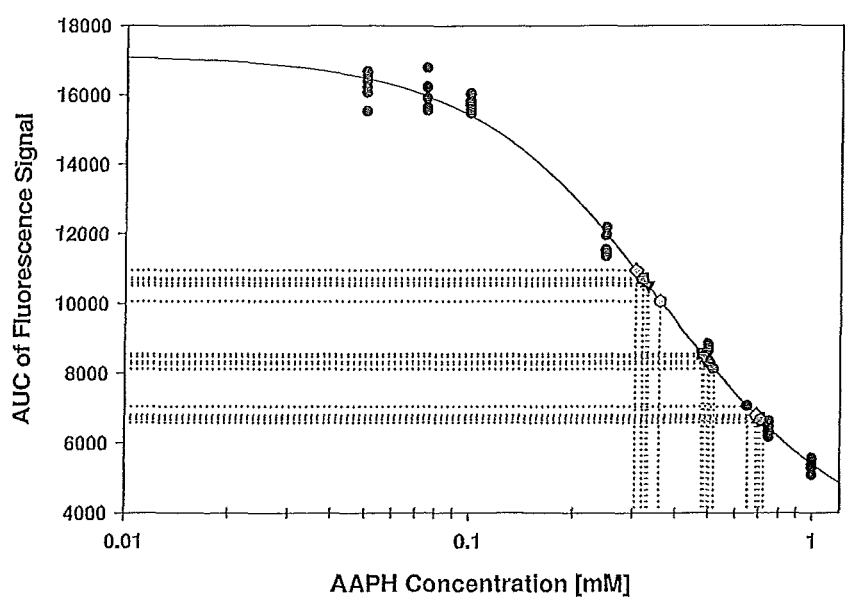
FIG. 24 is a graph of the Expt. 5f07 ROS Assay.

For the purposes of this work, we determined the oxygen radical content of our health benefiting product. In the assay described below, R-Phycoerythrin [an algal protein] is exposed to varying levels of a standard ROS generating compound [AAPH] wherein the level of fluorescence quenching is logarithmically related to ROS content. This provides a standard curve from which to estimate the ROS content of unknown samples. The levels of ROS in the unknown samples are expressed as mM equivalents of AAPH. FIG. 24 shows the concentration of AAPH.

Materials and Methods:

PHYCOERYTHRIN and R-PHYCOERYTHRIN: were purchased from Sigma Chemical Corporation, St. Louis, Mo.

AAPH: 2,2'-azobis(2-amidino-propane) dihydrochloride was purchased from Wako Chemicals USA, Richmond, Va. This compound generates ROS upon contact with water.

FLUORESCENCE READER: an 8 or 16 place fluorescence reader manufactured by Pacific Technologies, Redmond, Wash. was used to detect the fluorescence signal from the phycoerythrins. Temperature was controlled at 37 C during a 12-20 hr. experimental run. The samples were interrogated every 0.5 to 2 min where each sample interrogation was comprised of 1024 lamp flashes from a LED whose emission spectra was appropriate from the excitation spectra of R-Phycoerythrin. Proper cut-off filters were employed to detect the fluorescence emissions of the phycoerythrins.

DATA ANALYSES: All data is captured in real time. The data contained in the worksheet can be manipulated to determine the relative change of fluorescence over the time course of the experiment and subsequently, SigmaPlot Pro v. 7 software [SPSS Software, Chicago, Ill.] is used to determine the area under the curve. Area under the curve [AUC] analysis is appropriate since Cao, Cao et al. Comparison of different analytical methods for assessing total antioxidant capacity of human serum. Clinical Chemistry June 1998 vol. 44 no. 6 1309-1315 which is hereby incorporated by reference in its entirety, and colleagues have demonstrated that in this method both the inhibition time and degree of inhibition of fluorescence by free radicals are considered. The area under the curve [AUC] are plotted against the log 10 mM AAPH concentration to provide a standard curve from which to estimate the levels of ROS in unknown samples.

Detailed Methods:

Step a. 300 uL of phosphate buffer, pH 7.0, 100 mM is added to ½" glass vials.

Step b. 15 ug of R-Phycoerythrin in 15 uL of phosphate buffer is added to the materials in Step a. The vials are capped and placed into the wells of the fluorescence reader for 15 min prior to the addition of a saline control, ASEA or AAPH solutions. During this period, fluorescence values are collected from which to calculate a 100% value. This value is then used in subsequent calculations to determine a relative fluorescence signal value for the standard curves.

1 mg of AAPH is added to 1 ml of phosphate buffer and 10-fold dilutions are made to provide at least a 3 log 10 range of AAPH concentrations. Similarly, ASEA solutions are diluted and added to appropriate vials in Step b.

100 uL of the materials in Step a are added to the appropriate vials in Step b. The vials are mixed and replaced into the reader for up to an additional 12 to 20 hrs of evaluation.

RESULTS: As shown in FIG. 24, as the concentration of AAPH decreased from 1.00 mM to 0.050 mM, there was as concomitant increase in the normalized AUC. Buffer control [not shown] revealed that over time there is a spontaneous loss of fluorescence signal, although this loss represents only ~8% of the original signal.

Figure 25:
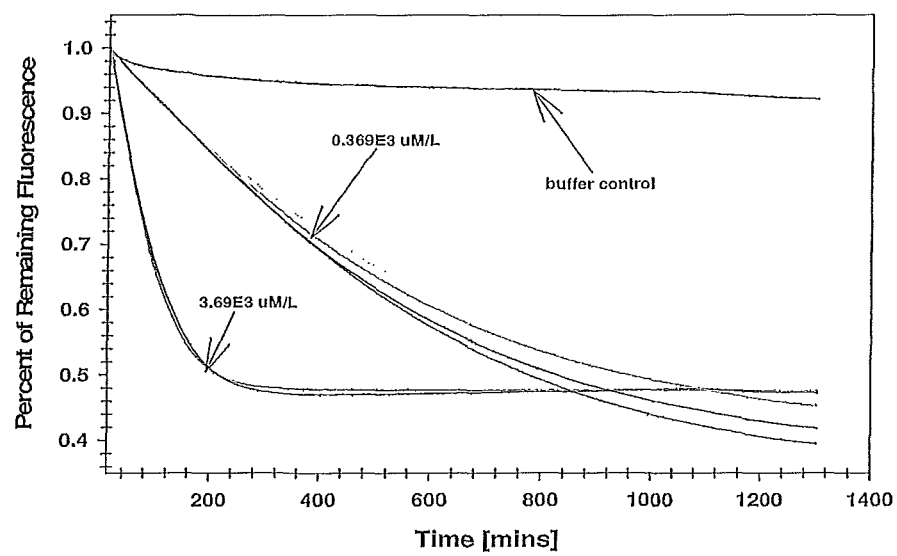
FIG. 25 is a graph of an Intraassay Variation Using Two Levels of AAPH.

The data represented in FIG. 25 shows intra-assay variability of two concentrations of AAPH. Using SigmaStat v 2.01 software, the following mean, Std Deviation and Relative Std Deviation were calculated and are presented in Table 1. The data shows that the variation for each concentration the variation among replicates ranged from ~0.1% to 4% variation [Rel. Std. Dev.]. These data suggest that fluorescence quenching assay is capable of producing small variations among triplicate or quadruplicate samples over a 10-fold range of AAPH concentrations.

TABLE 1

Intraassay Variability

| AAPH Concentration | N | Mean AUC | Std. Dev. | Std. Error | % Rel. Std. Dev. |
|---|---|---|---|---|---|
| 3.69 mM | 3 | 653 | 1.07 | 0.62 | 0.15 |
| 0.369 mM | 4 | 804 | 31.7 | 15.0 | 3.7 |

Table 2 shows the results of the analyses of ASEA solutions prepared by MDI and filtered through 0.2u Supor membrane to ensure sterility prior to clinical application. It is clear that the ASEA from different production lots are similar in their ROS content. Statistical analysis supported this observation [p=0.272]. The most important point is the observation that filtration through a 0.2u Supor membrane does not decrease the ROS content of ASEA.

Table 2. ROS Content of ASEA Filtered and Unfiltered Through 0.2 Supor Membrane

TABLE 2

| Treatment | N | Mean AUC | Std. Dev. | Std. Error | % Rel. Std. Dev. |
| --- | --- | --- | --- | --- | --- |
| Unfiltered | 4 | 589.7 | 65.8 | 32.9 | 5.5 |
| Filtered | 4 | 646.3 | 66.3 | 33.1 | 5.1 |

The levels of variance [Rel. Std. Dev.] reported by us is similar to that reported by Cao and colleagues.

In Table 3, data from a typical analysis is illustrated. Saline [negative control] always contained less than 0.1 mM AAPH equivalents of ROS whereas ASEA always contained >1.0 mM ROS.

TABLE 3

ROS Content of ASEA and Saline

| ASEA or Saline Samples | Mean AUC | ROS Content mM AAPH equivalents |
| --- | --- | --- |
| ASEA | 479 | 3.3 |
| ASEA | 543 | 2.2 |
| ASEA | 441 | 4.5 |
| ASEA | 523 | 2.98 |
| ASEA | 516 | 3.2 |
| Saline | 974 | 0.095 |
| Saline | 956 | 0.075 |

The above shows a known concentration of a standard, AAPH, as 653 and 804 when tested at 3.69 mM and 0.369 mM respectively. A composition comprising RXNs showed a AUC of between 441-543.

The measurement of concentrations of ROS inside the solutions can be done by means of a fluorospectrometer, Nanodrop 3300, and three varieties of fluorescent dyes, R-Phycoerytherin (R-PE), Hydroxyphenyl fluorescein (HPF) and Aminophenyl fluorescein (APF), all of which are commonly used to determine relative ROS concentrations inside active biological systems and cells. The molecules in these dyes change shape, and therefore fluoresce only when exposed to molecular components in ROS. The resulting change in fluorescence can then be detected by the fluorospectrometer and can be related to the concentration of ROS present. ROS concentrations in a compositions comprising RXNs can be verified and detected by either APF or R-PE fluorescent dyes, both of which produce entirely consistent measurements of relative concentrations of ROS in various concentrations and dilutions of RXNs. The ROS measurements in a compositions comprising RXNs have been linked, using R-PE fluorescent dye, to the reaction of this dye to regulated concentrations of 2/2'-Axobis(2-methylpropionamide) dihidrochloride, a molecule that produces known amounts of ROS.

Superoxide Testing

Superoxides were tested with the NanoDrop 3300 and R-PE as the reagent for the three samples.

The intensity of the fluorescence indicates the amount of ROS in the sample. This dye, R-PE, is toxic, expensive, must be kept refrigerated, degrades in strong blue light, such as a fluorescent bulb, and is time sensitive. The following steps were taken:

The ND-3300 software was called up, the "Other Fluorophores" button was clicked and the "R-PE 50 uM Activated" option was selected.

The ND-3300 was blanked: 2 uL (1 drop) of deionized water was placed using a pipette on the measurement pedestal and the arm was carefully closed. The "Blank" button was clicked and the ND-3300 took a "blank" measurement, thereby calibrating the ND-3300.

The samples were prepared by pipetting 10 ml deionized water into each one of the large (15 ml) test tubes required for the test. One test tube will be required for each sample to be tested.

The test tubes were labeled by cutting out squares of sticky-back label stock, large enough to fit over the mouth of the test tubes, and by writing the number "1", "2" and "3" on the label. The labels were placed covering the mouth of the test tubes to both identify them and to keep the liquids from evaporating.

10 ul of the R-PE fluorescent dye was apportioned into each of the test tubes by following these steps: turning off the lights, taking the previously prepared R-PE dye test tube out of the refrigerator [this test tube was previously prepared by putting 2 ul of the concentrate from the commercial R-PE vial inside 5 ml deionized water (a phosphate buffer is not needed)]. The prepared test tube was placed in the rack with the others. This dye is toxic and is sensitive to light so these steps should be done quickly, with lab coat, gloves and goggles. With a clean pipette, 10 ul of the prepared R-PE dye was add into each of the test tubes. The R-PE was placed back in the test tube back in the refrigerator.

The test tubes were mixed well using a mixing pipette which was place into each of the test tubes, 2-3 ml were drawn out and then quickly pushed back in, allowing some bubbles to escape to better agitate the contents of the test tubes. This was repeated three to four times for each tube. At this point, it is necessary to have separate mixing pipette heads for each tube. The test tubes were allowed to sit for least 30 min. after mixing.

The initial pre-sample measurements were taken on all of the test tubes: The ND-3300 was blanked using the procedures outlined above. A folded Kimwipe was used to blot the last sample droplet off the lower and upper pedestals before loading a new drop to be analyzed. A descriptive name for the sample was typed into the Sample ID field in the software. 2 ul of test tube #1 was loaded onto the pedestal, the arm was carefully closed and the "measure" button pressed. Three measurements were taken of the sample in test tube #1. This procedure was repeated for the next two samples. Specifically, the Sample ID field was changed to reflect the descriptive name of the sample in the second test tube. And then three (3) measurements were taken from the second test tube also. This step was done until all test tubes were analyzed. When R-PE was activated, the RFU readings shown were between the 100 and 2000.

A composition comprising RXNs was added to the test tubes: This procedure was carefully timed. The R-PE dye is only accurate for less than 30 minutes after activation and therefore all measurements must be acquired after the same amount of exposure time. 10 ul of a compositions comprising RXNs sample #1 was added to test tube #1 and immediately thereafter a timer was set for three (3) minutes. Then the test tube #1 was mixed with a pipette. This step was repeated for all three samples.

At 6 hrs post addition of the first a compositions comprising RXNs sample to a test tube, measurements were taken from every test tube in the following manner. The ND-3300 was blanked, the pedestals were blotted and the "Sample ID" for test tube #1 was typed in. After three (3) minutes, using a sampling pipette, a 2 ul drop was taken from test tube #1 and place it on the pedestal and the measure button was pressed. This process was repeated until all of the test tubes were measured.

The data was cleaned up by pressing the "Show Report" button so that all of the data that has been taken so far was displayed. The data was then saved and analyzed.

Hypochlorite Testing

Hypochlorites were tested with the NanoDrop 3300 Fluorospectrometer and APF as the reagent.

The ND-3300 software was called up, the "Other Fluorophores" button was clicked and the "APF 50 uM Activated" option was selected.

The ND-3300 was blanked: 2 uL (1 drop) of deionized water was placed using a pipette on the measurement pedestal and the arm was carefully closed. The "Blank" button was clicked and the ND-3300 took a "blank" measurement, thereby calibrating the ND-3300.

The samples were prepared by pipetting 10 ml deionized water into each one of the large (15 ml) test tubes required for the test. One test tube will be required for each sample to be tested.

The test tubes were labeled by cutting out squares of sticky-back label stock, large enough to fit over the mouth of the test tubes, and by writing the number "1", "2" and "3" on the label. The labels were placed covering the mouth of the test tubes to both identify them and to keep the liquids from evaporating.

10 ul of the APF fluorescent dye was apportioned into each of the test tubes by following these steps: turning off the lights, taking the previously prepared APF dye test tube out of the refrigerator [this test tube was previously prepared by putting 2 ul of the concentrate from the commercial APF vial inside 5 ml deionized water (a phosphate buffer is not needed)]. The prepared test tube was placed in the rack with the others. This dye is toxic and is sensitive to light so these steps should be done quickly, with lab coat, gloves and goggles. With a clean pipette, 10 ul of the prepared APF dye was add into each of the test tubes. The APF was placed back in the test tube back in the refrigerator.

The test tubes were mixed well using a mixing pipette which was place into each of the test tubes, 2-3 ml were drawn out and then quickly pushed back in, allowing some bubbles to escape to better agitate the contents of the test tubes. This was repeated three to four times for each tube. At this point, it is necessary to have separate mixing pipette heads for each tube. The test tubes were allowed to sit for least 30 min. after mixing.

The initial pre-sample measurements were taken on all of the test tubes: The ND-3300 was blanked using the procedures outlined above. A folded Kimwipe was used to blot the last sample droplet off the lower and upper pedestals before loading a new drop to be analyzed. A descriptive name for the sample was typed into the Sample ID field in the software. 2 ul of test tube #1 was loaded onto the pedestal, the arm was carefully closed and the "measure" button pressed. Three measurements were taken of the sample in test tube #1. This procedure was repeated for the next two samples. Specifically, the Sample ID field was changed to reflect the descriptive name of the sample in the second test tube. And then three (3) measurements were taken from the second test tube also. This step was done until all test tubes were analyzed. When APF was activated, the RFU readings shown were between the 100 and 2000.

A composition comprising RXNs was added to the test tubes: This procedure was carefully timed. The APF dye is only accurate for less than 30 minutes after activation and therefore all measurements must be acquired after the same amount of exposure time. 10 ul of a compositions comprising RXNs sample #1 was added to test tube #1 and immediately thereafter a timer was set for three (3) minutes. Then the test tube #1 was mixed with a pipette. This step was repeated for all three samples.

APF, as well as RPE, are measured relative to a chosen standard and are reported as percentages of such standard.

At 30 min. post addition of the first a compositions comprising RXNs sample to a test tube, measurements were taken from every test tube in the following manner. The ND-3300 was blanked, the pedestals were blotted and the "Sample ID" for test tube #1 was typed in. After three (3) minutes, using a sampling pipette, a 2 ul drop was taken from test tube #1 and place it on the pedestal and the measure button was pressed. This process was repeated until all of the test tubes were measured.

Packaging

The packaging process includes any type of packaging that does not contribute to the decay of the superoxides, hydroxyl radicals and OOH* (for example, containers should not contain metal oxides or ions). Pouches and bottles are preferred for ease of portability and acceptability in the market. However, any suitable packaging is applicable. Containers/packaging can be made of for example glass, polyethylene, polypropylene and the like. Specific examples include Bapolene HD2035, which is a high density polyethylene copolymer and Jade brand CZ-302 polyester. Table 4 shows the relative percentage of superoxides remaining after a 12 month period when the composition is packaged in a polyethylene bottle.

Example 6

The rate of decay for superoxides, from a sample made according to Example 1, was tested over a 12 month period. That is, superoxides present in a sample made when a total of 1,000 gallons of salinated water is electrolyzed with a total of 56 amps running through the electrodes and further wherein the electrolyzing occurred at 4.5-5.8° C., according to Example 1, were tested for their relative amounts over a period of 12 months relative to a standard RFU control for RPE.

TABLE 4

1 Year Studies - shows a 3%/month decay rate over a 12 month period

| Sample ID | RFU | RFU Average per sample | RFU minus control | Standard deviation | % error | % Potency/Stability as compared to reference sample |
|---|---|---|---|---|---|---|
| RFU Control | 1743.7 | 1759.033 | | | | |
| Control | 1814.6 | | | | | |
| Control | 1718.8 | | | | | |
| Sample 1 | 985.6 | 986.1667 | 872.8667 | 6.169549 | 0.706815 | 1 |
| Sample 1 | 980.3 | | | | | |
| Sample 1 | 992.6 | | | | | |
| Sample 2 | 1044.8 | 1003.6 | 855.4333 | 35.68151 | 4.171162 | Baseline |
| Sample 2 | 982.7 | | | | | |
| Sample 2 | 983.3 | | | | | |
| Sample 3 | 981.7 | 988.3 | 870.7333 | 16.23915 | 1.864997 | 1.007618 |
| Sample 3 | 1006.8 | | | | | |
| Sample 3 | 976.4 | | | | | |
| Sample 4 | 1132.9 | 1121.133 | 737.9 | 12.56437 | 1.70272 | 0.853903 |
| Sample 4 | 1107.9 | | | | | |
| Sample 4 | 1122.6 | | | | | |
| Sample 5 | 1189.9 | 1182.2 | 676.8333 | 19.99475 | 2.954161 | 0.783236 |
| Sample 5 | 1197.2 | | | | | |
| Sample 5 | 1159.5 | | | | | |
| Sample 6 | 1269.3 | 1256.267 | 602.7667 | 26.47647 | 4.39249 | 0.697526 |
| Sample 6 | 1225.8 | | | | | |
| Sample 6 | 1273.7 | | | | | |

Figure 22:
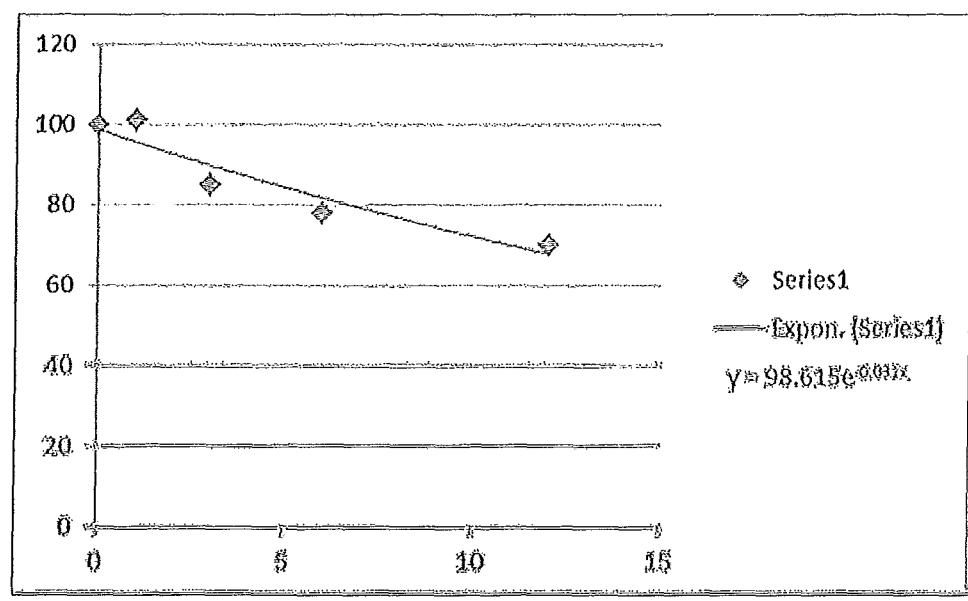
FIG. 22 is a graph of the decay rate of superoxide over a period of 1 year.

Table 4 provides data for the RFU control, Sample 1 which is a reference sample and Samples 2-6 which were taken at 1 month, 3 months, 6 months and 12 months respectively. Table 4A shows the results as a percentage of remaining superoxides at 0, 1, 3, 6 and 12 months. This Table 4 is graphically represented in FIG. 22.

TABLE 4A

| Month | % Potency/Stability |
|---|---|
| 0 | 100 |
| 1 | 101 |
| 3 | 85 |
| 6 | 78 |
| 12 | 70 |

Example 7

Table 5 shows the relative percentage of superoxides remaining after a 13 month period when the composition is packaged in a polyethylene bottle and polyethylene pouch. In this Example, the composition tested was made according to the process of Example 6.

TABLE 5

13 Month Pouch v. Bottle

| Sample ID | RFU | RFU Average per sample | Standard deviation | % error | RFU minus control | % Potency/Stability as compared to reference sample |
|---|---|---|---|---|---|---|
| Control | 1687.9 | | | | | |
| 555 | 946.4 | 940.7667 | 9.157693 | 0.973429 | 1325.273 | 1 |
| 555 | 930.2 | | | | 1370.007 | |
| 555 | 945.7 | | | | | |
| 555-1 | 817.5 | 851.3 | 29.27781 | 3.439188 | 1414.74 | 1.067508 |
| 555-1 | 867.6 | | | | | |
| 555-1 | 868.8 | | | | | |
| 525b | 967.2 | 966.0333 | 10.3992 | 1.076484 | 1300.007 | 0.948905 |
| 525b | 955.1 | | | | | |
| 525b | 975.8 | | | | | |
| 524p | 983.1 | 975.7333 | 17.08576 | 1.751069 | 1290.307 | 0.941825 |
| 524p | 956.2 | | | | | |
| 524p | 987.9 | | | | | |
| 480 | 985.9 | 1006.333 | 19.12337 | 1.900302 | 1259.707 | 0.919489 |
| 480 | 1009.3 | | | | | |

TABLE 5-continued

13 Month Pouch v. Bottle

| Sample ID | RFU | RFU Average per sample | Standard deviation | % error | RFU minus control | % Potency/ Stability as compared to reference sample |
|---|---|---|---|---|---|---|
| 480 | 1023.8 | | | | | |
| 479p | 1115.2 | 1153.5 | 45.22975 | 3.921088 | 1112.54 | 0.812069 |
| 479p | 1141.9 | | | | | |
| 479p | 1203.4 | | | | | |
| 408p | 1454.2 | 1501.633 | 62.98812 | 4.194641 | 764.4067 | 0.557958 |
| 408p | 1573.1 | | | | | |
| 408p | 1477.6 | | | | | |
| 347p | 1309.4 | 1327.833 | 39.24364 | 2.955464 | 938.2067 | 0.684819 |
| 347p | 1301.2 | | | | | |
| 347p | 1372.9 | | | | | |
| 347p | 1338.1 | | | | | |
| 314 | 1354.4 | 1348.567 | 16.82627 | 1.247715 | 917.4733 | 0.669685 |
| 314 | 1361.7 | | | | | |
| 314 | 1329.6 | | | | | |
| 313p | 1459.3 | 1444.033 | 13.25908 | 0.918198 | 822.0067 | 0.600002 |
| 313p | 1435.4 | | | | | |
| 313p | 1437.4 | | | | | |

Figure 23:
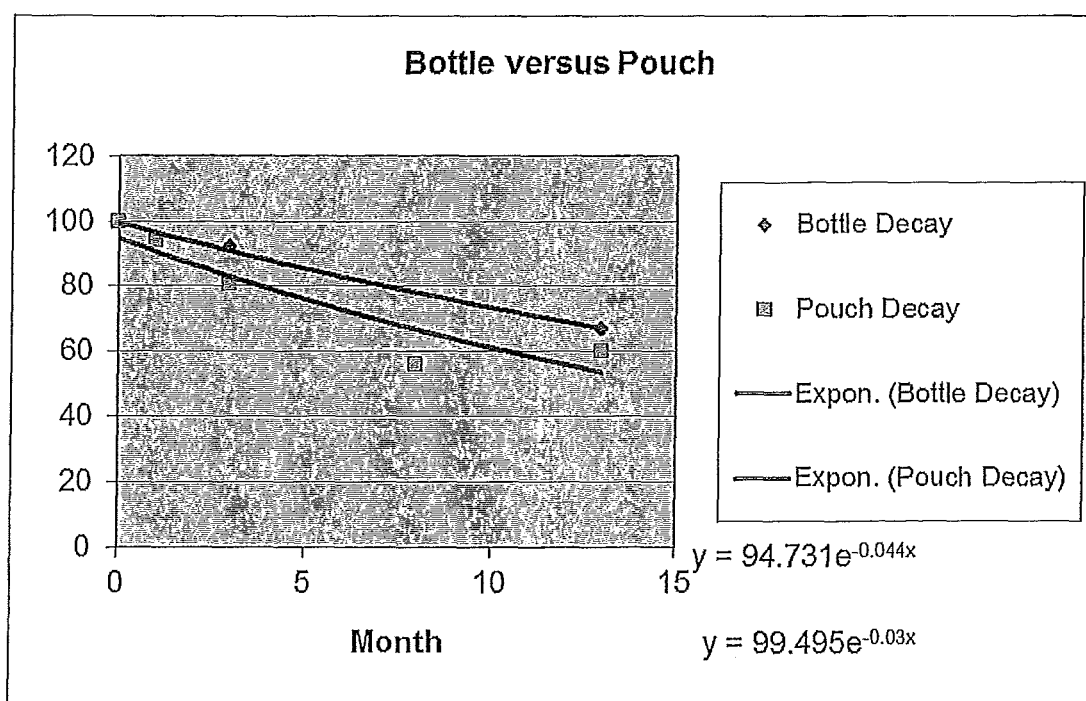
FIG. 23 is a graph showing the comparison of the decay rates of superoxide when the mixture is stored in a bottle and when the mixture is stored in a pouch.

The above graph shows a 4.4% decay rate of the superoxide radical for the pouch and a 3% decay rate for the bottle over a 13 month period. Sample 555 is a reference sample, Sample 555-1 is a baseline sample, Sample 525b is a sample taken from a bottle after 1 month, Sample 524p is a sample taken from a pouch after 1 month, Sample 480 is a Sample taken from a bottle after 3 months, Sample 479p is a sample taken from a pouch after 3 months, Sample 408p is a sample taken from a pouch after 8 months, Sample 374p is a sample taken from a pouch after 11 months, Sample 314 is a sample taken from a bottle after 13 months and Sample 313p is a sample taken from a pouch after 13 months. Table 5A is a chart showing the percentage of remaining superoxides at 0, 1, 3, 8, 11 and 13 months in a bottle and a pouch type container. This Table 5 is graphically represented in FIG. 23.

TABLE 5A

| Month | Bottle % Potency/Stability | Pouch % Potency/Stability |
|---|---|---|
| 0 | 100 | 100 |
| 1 | 95 | 94 |
| 3 | 92 | 81 |
| 8 | | 56 |
| 11 | | 68 |
| 13 | 67 | 60 |

Example 8

Borosilicate glass, such as those sold under the trade names of Kimax, Pyrex, Endural, Schott, or Refmex for example, are useful for packaging of compositions comprising RXNs.

The presence of superoxides in compositions comprising RXNs samples were tested after being stored in borosilicate glass bottles. The samples were made according to the process described in Example 6. Sample 397 had been stored for 24 months and Sample 512 had been stored for 20 months. Reference batch 1256 was made the same day as the test was run on all three samples. The Results are shown in Table 6.

TABLE 6

Glass Bottle ASEA Stability

| Sample | RFU | average RFU | Control − average + control loss | % Potency/ Stability as compared to reference sample |
|---|---|---|---|---|
| 397 | 780.5 | 806.8 | 1193.2 | 93.1169 |
| | 819.5 | | | |
| | 820.4 | | | |
| 512 | 676.7 | 682.4666667 | 1317.533333 | 102.8198 |
| | 682.6 | | | |
| | 688.1 | | | |
| Reference sample 1256 | 754.8 | 718.6 | 1281.4 | 100 |
| | 707.2 | | | |
| | 693.8 | | | |
| Control | 1850 | | | |
| Control after 6 hours | 1700 | | | |

It can be seen from the Tables that the relative concentrations of superoxides do not appreciably degrade while in the borosilicate bottles. Sample 397 had a decayed about 5% and sample 512 had 0% decay. Therefore, the yearly decay of product is no more than about 2.5% decay per year. This gives an estimated half-life of the superoxides at about 24 years.

The stability of any component in the composition can be measured by the amount of the particular composition which remains detectable after a certain amount of time. For example, if the superoxides measured had a decay rate of about 7% over a two year period, this would mean that the stability over the 2 year period was about 93%. In other words, after a two year period, about 93% of the original amount of superoxides, were still present and measured in the composition.

Example 9

Two 1 L 0.9% NaCl solutions were made and three 0.28% 1 L NaCl solutions were made from 0.28% distilled NaCl solutions. Salinity was analyzed with an EC300 conductivity meter and salt was added until the desired salinity (9 g/L or 0.9%) was reached. Samples were then mixed and placed in the freezer. 0.28% samples were collected directly from the saline storage tanks. Salinity was confirmed at 2.8 g/L (or 0.28%) by the EC300 conductivity meter. Samples were placed in the freezer.

Samples were removed from the freezer when the temperature read at 5.5° C. and placed in the fridge. One of the 2.8 g/L sample was run at 3 amps for 3 min at 5.8° C. to rinse the 1 L cell, after which the samples in the following table were run similar to the process of Example 3.

| Sample | Salinity (g/L) | Amps | Time (min) | Temp (C.) |
|---|---|---|---|---|
| 1 | 2.8 g/L | 3 | 3 | 5.8 |
| 2 | 2.8 g/L | 3 | 3 | 5.8 |
| 3 | 9 g/L | 3 | 3 | 5.6 |
| 4 | 9 g/L | 3 | 3 | 4.9 |

Free Chlorine, R-PE, APF and pH were measured for the 0.28 and 0.9% samples and the results were as shown in the following table.

| Sample/NaCl % | Free Chlorine | R-PE | APF | pH |
|---|---|---|---|---|
| 1/0.28% | 31 ppm | 112% | 112% | 7.6 |
| 3/0.9% | 76 ppm | 123% | 35% | 8.3 |
| 2/0.28% | | 112% | 108% | |
| 4/0.9% | | 125% | 48% | |

*Free Cl was tested using glass cells for 1 in the LR and 3 was measured in plastic cells in the HR.

Example 10

A composition made according to Example 1—KI TITRATION WITH $Na_2S_2O_3$

A titration was set up to determine the amount of ClO in a composition made according to Example 1 (for this Example 10 a composition made according to Example 1 is referred to RXN1) by reacting ClO in RXN 1 with KI and acid to make I2 and Cl—. The I2 is brown in color and becomes clear upon complete reaction with S2O3— and 2I—.

The reagents are KI 42 mM with Glacial acetic acid solution (KIGAA), RXN1 and 0.100 M $Na_2S_2O_3$ solution. The 42 mM KI solution was prepared by adding 1.758 g of KI and 5 mL of GAA to a 250 mL Erlenmeyer flask and bringing the volume to 250 mL with DI $H_2O$. 0.100M $Na_2S_2O_3$ solution was created by adding 2.482 g of $Na_2S_2O_3$ to a 100 mL volumetric flask, then adding DI $H_2O$ until 100 mL was reached. RXN1 was taken from batch 1371. Three tests were performed.

TEST 1: 50 mL of RXN1 was added to 50 mL KIGAA and mixed. The buret was rinsed three times with DI $H_2O$ then rinsed with $Na_2S_2O_3$ and filled with $Na_2S_2O_3$ to 4 mL. Initial buret reading started at 6 mL and ended at 5.69 mL. A total of 0.31 mL was added to complete the titration. Results indicate about 16 ppm of ClO ($3.1 \times 10-4$M ClO).

TEST 2: 75 mL RXN1 was added to a 50 mL KIGAA and allowed to mix. Initial buret reading was 14 mL and final was about 13.55. A total of 0.45 mL was added. Results indicate about 16 ppm of ClO ($3 \times 10-4$M ClO).

TEST 3: 100 mL RXN1 was added to 50 mL KIGAA. Initial buret reading was at 15 mL and the final reading was at about 14.37 mL. Approximately 0.63 mL was added in total. Results indicate about 16 ppm of ClO ($3.15 \times 10-4$M ClO).

CONCLUSION: After three Tests it appears that the ClO concentration of RXN1 is close to $3.1 \times 10-4$M. This corresponds to about 16 ppm which is close to what the colorimeter read on a sample from another batch (batch 1371, which tested at 20 ppm).

Example 11

The AccuTOF-GCv 4G is a highly sensitive (S/N>100 at OFN 1 pg/μL) time-of-flight Gas Chromatography Mass Spectrometer. High resolution and mass accuracy allow for rapid elemental composition determination and target compound identification. To test for water clusters in a composition of the present invention, the composition was run in the MS and injection temperatures were lowered to the point where water clusters were detectable.

Figure 26:
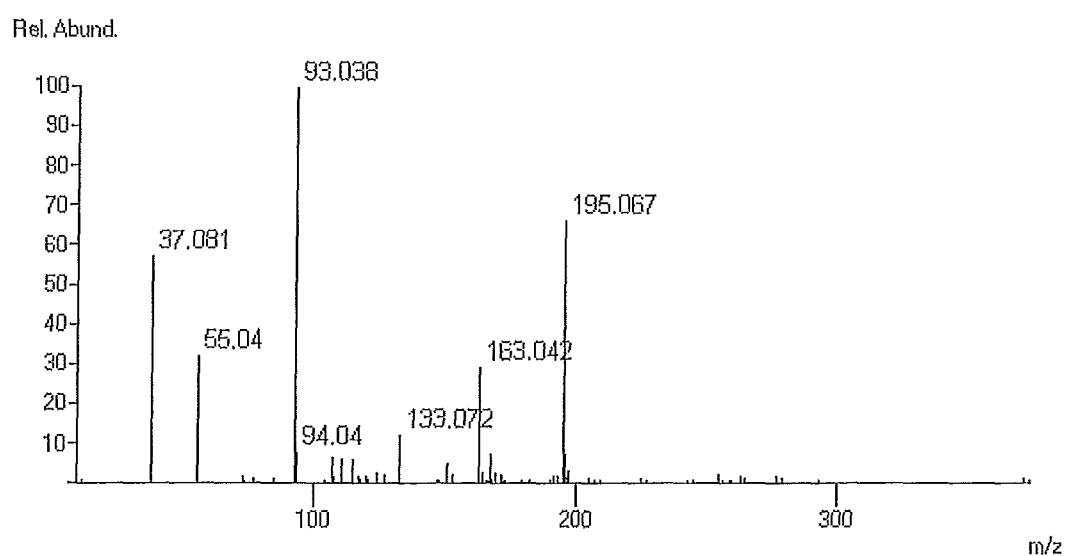
FIG. 26 illustrates a JEOL DART low temperature sample injection TOF Mass Spectrum of a composition of the present invention showing water clusters [(H2O)n+H]+ peaks at 37 and 55.
Figure 27:
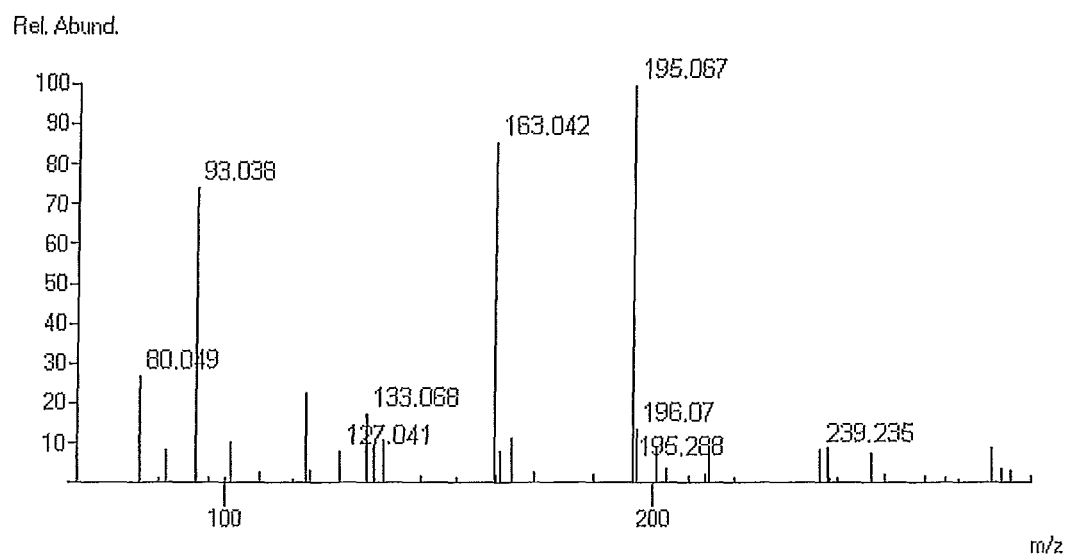
FIG. 27 illustrates a JEOL DART low temperature sample injection TOF Mass Spectrum of a composition of the present invention wherein the positive-ion mass spectrum, masses >m/z 60.
Figure 28:
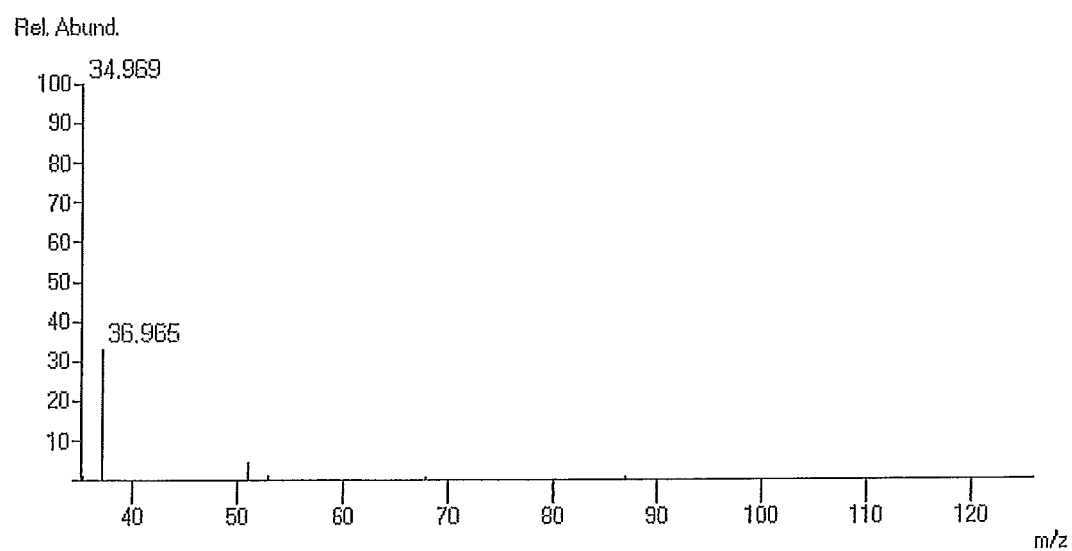
FIG. 28 illustrates a JEOL DART low temperature sample injection TOF Mass Spectrum of a composition of the present invention showing negative ions peaks at 35 and 37.
Figure 29:
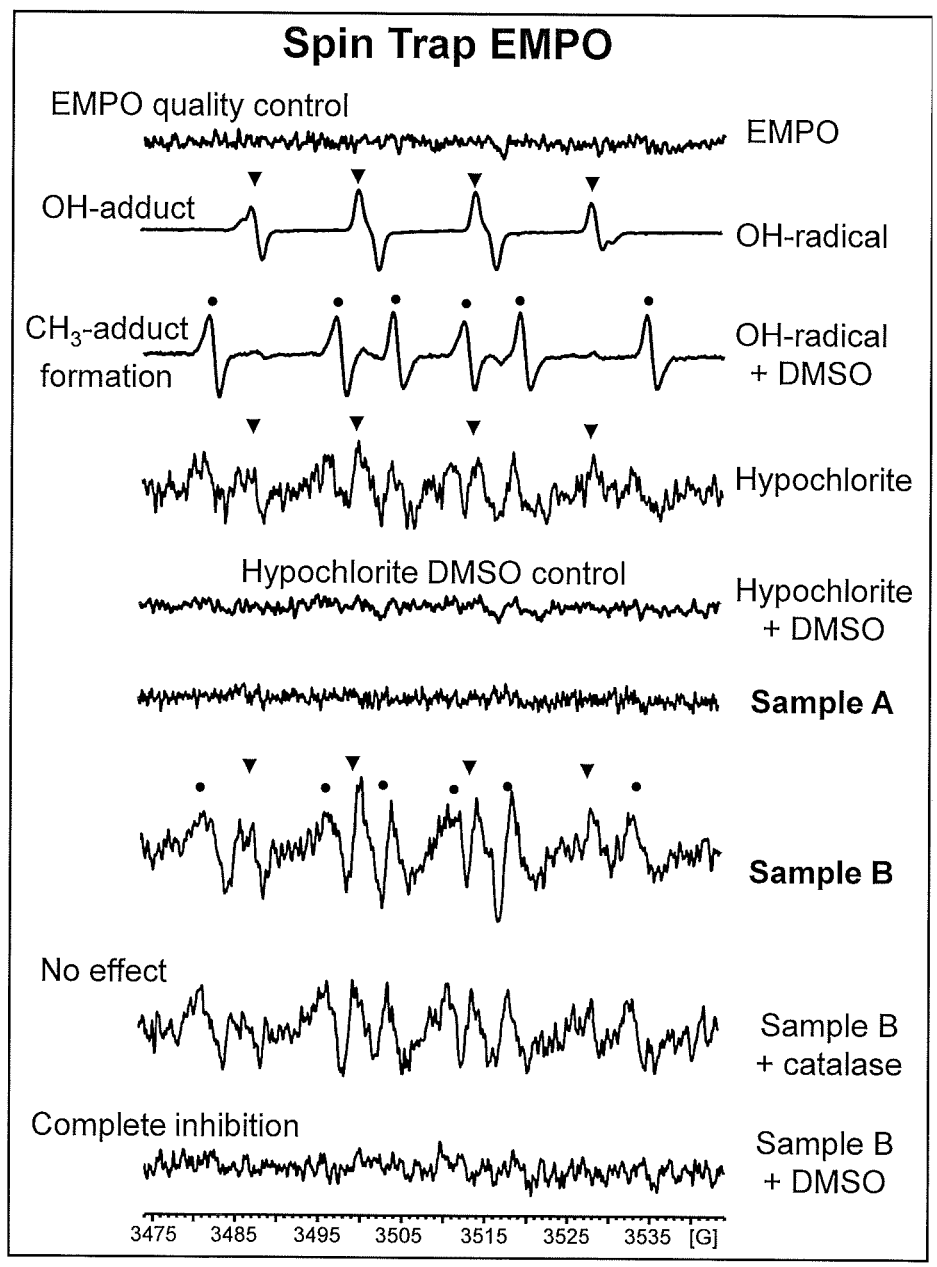
FIG. 29 is an EPR analysis of free radicals and reactive oxygen species tested in a sample of an ingredient used to make the inventive gel composition described herein.
Figure 30:
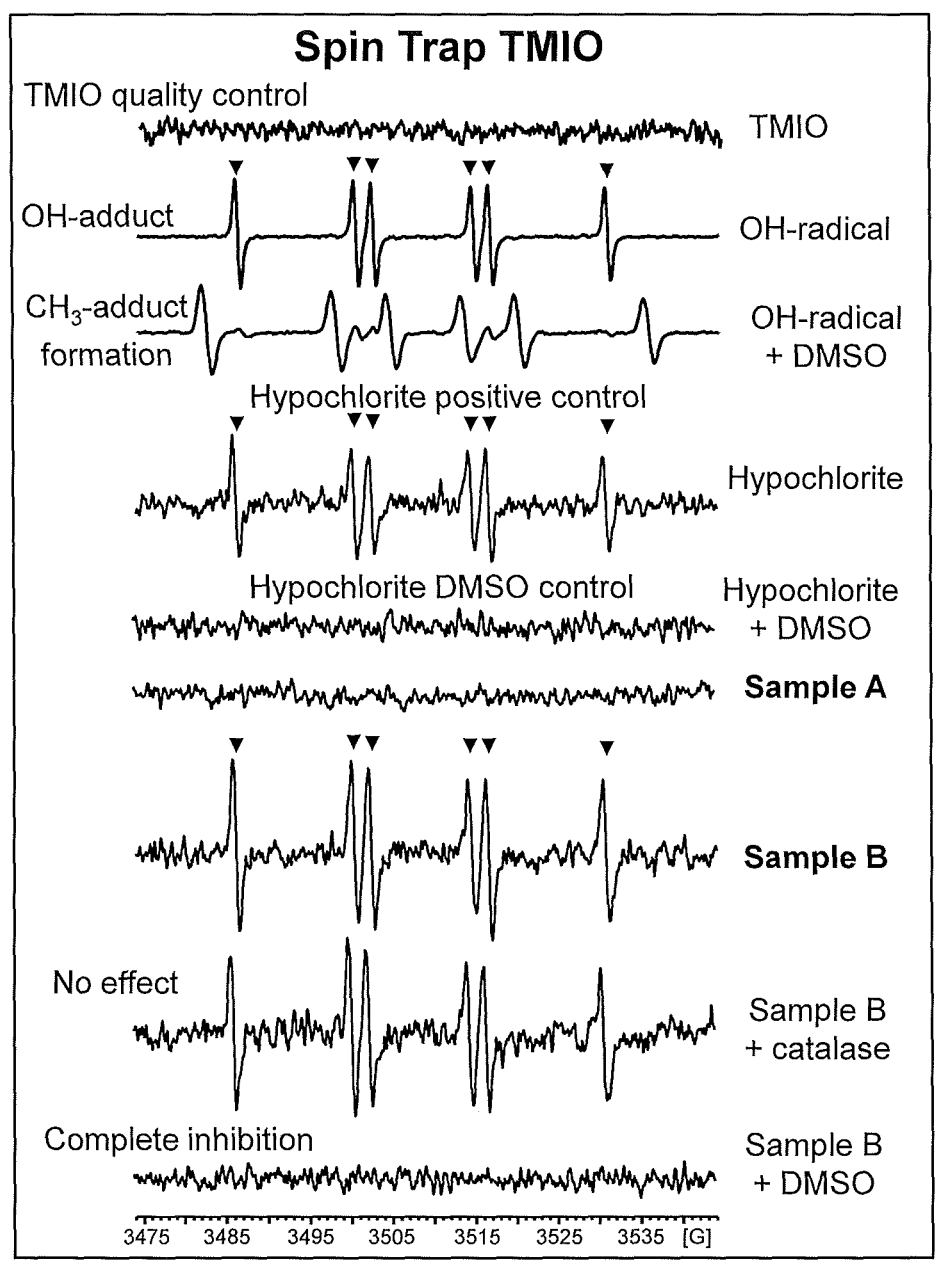
FIG. 30 is an EPR analysis of free radicals and reactive oxygen species tested in a sample of an ingredient used to make the inventive gel composition described herein.

The spectra showed the existence of several active oxygen complexes, including ClO— and O2 in complexes with ClO— and the existence of the O2*-radical in several forms. These spectra are shown in FIGS. 26-28. At low mass, we see only water clusters [(H2O)n+H]+ at 37 and 55, filament Temperatures are low enough to not break down water.

Example 12

Hydrogen peroxide was tested by ultravioletvisible (UV/VIS) spectroscopy according to Standard Test Protocol (STP) Number STP0163 Rev2 by Nelson Laboratories in Salt Lake City. According to this test, hydrogen peroxide was present in a composition according to the present invention at 1.6 ppm by weight.

Example 13

Evaluation and measurements of pH, Peroxide, Chlorine, free and total, Redox and Ozone were taken from a composition made according to Example 3.

Three initial lots of materials were processed consisting of 15 sublots for run 1, 30 sublots for run 2 and 40 sublots for run 3. During run 3, sublots 1, 15 and 30 were also tested for pH changes and Peroxide productions as intra-assay sublot controls. Starting material was also tested with each lot to determine which parameters changed during processing. Data showed a change in pH, Peroxide, Chlorine, free and total, as well as increased Redox and production of Ozone. There was no change in Osmolarity or Chloride levels but a decrease was seen in Sodium levels.

Samples from run 3 were also tested after 2 weeks storage at room temperature (~25° C.). At this time two samples of the material were removed and treated by freeze thaw and by heating to 100° C. in order to determine stability indicating parameters. This data showed that storage at room temperature for 2 weeks changed the Chlorine free and total levels and ratios from an initial mean value of the three runs of 60 to 60 ppm free to total and decreased to 16 to 52 ppm free to total. Freeze thawing this material gave values of 36 to 77 ppm, but heating further decreased these values to 8 to 32 ppm. The Sodium values after two weeks storage also appeared to be lower then the range (1.5 times standard deviation of the three runs) of 2470 to 4123 ppm down to 2100 ppm. This however did not appear to change (within assay variation) when samples were freeze thawed or boiled. The Chloride, Redox, and Peroxide appeared to be within error of the initial data for all three samples (2 week RT, freeze thawed and boiled). Osmolarity was slightly higher for the freeze thawed and boiled samples but may be within assay error or was due to the concentration of the sample caused by treatment.

Prior to initiation of PQ (Performance Qualification) runs, engineering runs were conducted to determine reproducibility of process and to generate material for determination of specific testing methods and parameters. Additionally, material was used to determine parameters that would be stability indicating. Material was produced using the apparatus and method described in Example 3. Unit has undergone IQ/OQ prior to study. Sublots were prepare using 0.9% sterile injectable Saline at one liter per sublot. Initial run consisted of 15 sublots that were pooled, pH adjusted and 0.2u filtered. Aliquots were removed for initial testing using the following Steps.

Steps

1. Visual Inspection: Clear colorless liquid
2. Particulate matter: No visual particles under normal lighting
3. pH: Determination of pH was conducted based on United States Pharmacopoeia, USP <791> using GBI SOP EC-855. Instrumentation included a Corning 425 meter and an Accent 13-620-95 combination electrode. System was standardized at 25° C. using NIST traceable buffers that gave a slope of >97%.
4. Osmolarity: Determination of Osmolarity was conducted per USP <785> using an Osmette A model 5002 per GBI SOP AL-872. Unit was standardized with NIST traceable calibration standards and a reference control of 290 mOsm.
5. Peroxide: Generation of Peroxide was measured using a Peroxide test kit from Merckquant and semi quantitative levels were determined per GBI SOP AL-876. This test uses a test strip comparison method to a color scale. Levels of detection are 0.5, 2, 5, 10 and 25 ppm. Higher-level samples can be diluted and measured. Mid color estimates could be done if necessary.
6. Chlorine total and free: Free Chlorine in the sample as hypochlorous acid or hypochlorite ion (free Chlorine or free available Chlorine) immediately reacts with DPD (N, N-diethyl-p-phenylenediamine) indicator to form a magenta color which is proportional to the free Chlorine concentration. Color measurements are made using a Hach Colorimeter model DR850. Reagent kits are also obtained from Hach. It should be note that the presence of Ozone interferes with the accurate measurement of free Chlorine and the presence of Peroxides may interfere also.

Chlorine can be present as free or combined available Chlorine and is measured together as total available Chlorine. Combined Chlorine exits as monochloramine, dichloramine, nitrogen triChloride and other chloro derivatives. The combined Chlorine oxidizes Iodide in the test reagent to Iodine. The Iodine reacts with DPD along with free Chlorine present in the sample to form a red color that is proportional to the total Chlorine concentration. Combined Chlorine can be calculated by subtracting the free from the total Chlorine test result. It should be noted that Ozone and Peroxide in the sample might give inaccurate measurements with these reagents.

7. Redox Potential (ORP): This method measures the oxidizing or reducing capacity of a solution in mV units. A Platinum Redox Electrode (SympHony Electrodes) is utilized with a millivolt pH meter. Redox potential is expressed in terms of a standard electrochemical reduction potential, symbolized as E o, with millivolt (mV) as units. The value is measured against a standard hydrogen couple ($2H+$, $H_2$), a universally accepted frame of reference. By convention, a positive (+) sign accompanies the reduction potential that has a greater tendency to undergo reduction relative to the hydrogen system. A negative sign is used for solution that have a lesser tendency to undergo reduction. Since the conventional standard is pH 7, measurements are pH dependent and appropriate calculation are required to adjust E o value to a condition applicable to pH (E o/). Example half-reaction couple potentials for water at 20 to 30° C. at pH 7 is 820 mV. ($½O_2+2H_2+2e$ $H_2O$).

8. Chloride: Chloride is measure using a Chloride combination electrode from Cole-Parmer (27077-04) attached to a IC 7685 Ion controller. Meter is calibrated with a 100 and 1000 ppm Chloride standard and samples are measured in terms of ppm Cl—. A 500 ppm reference standard is also used to determine reproducibility of the readings for Quality purposes.

9. Sodium: Sodium is measure similar to Chloride using a Sodium combination electrode from Cole Parmer (277077-16). Standards of 100 and 1000 ppm are used and a 350 ppm reference standard is also used to determine reproducibility of the readings for Quality purposes.

10. Ozone: Measurements of Ozone levels are made using a HACH colorimeter Indigo method. Method has a detection level of 0.1 ppm. Ozone ($O_3$) is the gaseous form of Oxygen having 3 atoms per molecule rather than the usual 2.

Results: Samples from pre-treated 0.9% Sodium Chloride for injection were measured against post treatment product. Table 1 shows the mean, standard deviation (SD) and percent coefficient of variance (% CV) for the three lots. No trends were present based on the number of sublots prepared from values obtained on the initial lot consisting of 15 sublots, the second lot that had 30 sublots and the third lot consisting of 40 sublots. Assays have not been qualified for intra and inter variability therefore trend analysis and % CV comparison can only be made between starting and treated samples and the contribution of assay variability and operator variability is presently not known. It is known from manufacturer's literature that the presence of Ozone and Peroxide may give inaccurate values for the Chlorine analysis. Also Redox analysis is pH dependent and the starting untreated saline may require adjustment to pH 7 in order to determine if increases in Redox potential are due to treatment or are just related to the differences in the pH of the two products tested at the same time.

Osmolarity is in agreement with the calculated values that should be obtained based on the manufacturer's specification for percentage of Sodium Chloride present. (The freezing point depression at ΔoC for a 0.89% solution is 0.53. Osmolarity=Δ/1.86 or 0.285 Osm (285 mOsm). These values do not appear to change between non-treated, treated, nor over time, or after stress treatment of freezing or boiling (Table 7).

TABLE 7

| Test Performed | O time (Sep. 23, 2004) treated | RT stored material Aug. 5, 2004 Ctr | Ctr freeze thawed −20° C. | Ctr Boiled 100 C. 1 min |
|---|---|---|---|---|
| PH | 6.99 | 7.1 | 7.0 | 6.52 |
| Osmolarity mOsm | 285 | 287 | 290 | 296 |
| Peroxide Ppm | 10 | 10 | 10 | 10 |
| Chlorine Total mg/L (ppm) | 72 | 52 | 77 | 32 |

TABLE 7-continued

| Test Performed | O time (Sep. 23, 2004) treated | RT stored material Aug. 5, 2004 Ctr | Ctr freeze thawed −20° C. | Ctr Boiled 100 C. 1 min |
|---|---|---|---|---|
| Chlorine Free mg/L (ppm) | 67 | 16 | 36 | 8 |
| Redox mV | 830 | 830 | 840 | 870 |
| Chloride mg/L (ppm) | 4670 | 5180 | 5260 | 4680 |
| Sodium mg/L (ppm) | 2470 | 2100 | 2000 | 2040 |
| Ozone mg/L (ppm) | 0.61 | 0.43 | 0.23 | 0.20 |

Peroxide appears to increase and this increase appears to be stable to stress treatment. Ozone also increased post treatment but unlike Peroxide, appears to decrease over time and appears to be effected by stress treatments.

Levels of Sodium and Chloride in non-treated solutions are in agreement with calculated values. Chloride post treatment appears to be within assay error and appears to remain stable to stress treatment. Sodium appears to decrease when starting concentration is compared to treated samples. The overall net decrease for the three runs gave a mean of 1247+/−227 and appears to be statistically significant from assay variability. These decreased values, however, do not appear to change when samples were stressed.

Levels of free and total Chlorine and calculated combined Chlorine may not be valid due to interference from the presence of Ozone and Peroxide. Untreated starting material appears to have little if any measurable levels of Chlorine. Post treatment values increase to a mean of 60 ppm for free and total indicating no combine Chlorine is present. These values, however, might be influence by the presence of Ozone and Peroxide. It should also be noted that Chlorine has a tendency to be absorbed by plastics and may also be affected by the materials being used to collect and store the sublots and final bulk materials as well as the container used for sampling. Material stored for two weeks showed a change in the ratio of free and total and if calculated gave a value of 36 ppm of combine Chlorine with the values for Ozone and Peroxide being equivalent to the 0 time treated test results that showed values of 60 ppm for both free and total indicating no combined Chlorine present. If should also be noted that when stressed treated by heat, the Ozone values decreased and the total and free values for Chlorine also decreased. The stressed treated samples at initial testing gave a value of 0 for combine Chlorine, 36 ppm at 2 weeks and this sample when boiled gave a values of 24 ppm for combined Chlorine and 41 ppm after freeze thaw.

Determination of Stress Effects of Temperature:Engineering run three was stored at room temperature for two weeks in a PETG bottle. This material was re-tested after this period. Comparison of post treatment material from the 40 L pooled engineering Run #3 was originally performed and tested on Jul. 23, 2004. This material was stored at room temperature and samples taken and treated by freeze thawing and boiling to determine possible stability indicating assays. Data is shown in Table 2.

Sample preparation: Room Temperature sample removed directly from original container. Frozen sample was aliquoted into 50 mL (3×25 mL) conical tubes and frozen overnight. Sample was removed the following day, brought to room temperature and tested.

Boiled sample: 75 mL was placed in a 125 mL flask, covered with tin foil and placed into water bath. Temperature was brought to 1000 C. Sample was boiled for 1 minute and aliquoted into 50 mL conical tubes. (3×25 mL)

Conclusions: Additional testing will be conducted on the PQ runs to determine reproducibility of the values obtain. Stability studies will also be conducted to determine if variations are occurring over time when product is stored at refrigerated, room or elevated temperatures. Other testing by outside sources for biological activity is not yet available, however, storage containers, and time of holding may be important in determination of activity. Other testing for metals and leachable will be done as well as endotoxin and sterility on the PQ pooled filtered samples.

TABLE 8

Table 8: Summary Data of Engineering Runs

| | pre treatment | Post treatment | Parameter |
|---|---|---|---|
| mean | 5.65 | 7.05 | pH |
| SD | 0.84 | 0.04 | pre-4.5 to 7.0 |
| % CV | 14.87 | 0.54 | |
| range | 4.39 to 6.91 | 6.99 to 7.10 | |
| mean | 284.67 | 285.00 | exp 277 to 326 |
| SD | 0.44 | 0.00 | |
| % CV | 0.16 | 0.00 | Osmolarity |
| range | 284 to 285.3 | 285 to 285.00 | mOsm |
| mean | 0.00 | 10.00 | ppm |
| SD | 0.00 | 0.00 | Peroxide |
| % CV | #DIV/0! | 0.00 | |
| range | 0 to 0.0 | 10 to 10.00 | |
| mean | 0.02 | 60.00 | Chlorine |
| SD | 0.02 | 8.00 | Total |
| % CV | 76.19 | 13.33 | mg/L |
| range | 0.00 to 0.05 | 48.00 to 72.00 | |
| mean | 0.01 | 59.33 | Free |
| SD | 0.00 | 5.11 | mg/L |
| % CV | 33.33 | 8.61 | |
| range | 0.007 to 0.0 | 51.67 to 67.00 | |
| mean | 320.50 | 860.53 | mV |
| SD | 67.67 | 20.36 | Redox |
| % CV | 21.11 | 2.37 | |
| range | 219 to 422.0 | 830 to 891.07 | |
| mean | 5140.00 | 4776.67 | Chloride |
| SD | 213.33 | 395.56 | ppm |
| % CV | 4.15 | 8.28 | exp 5187 to |
| range | 4820 to 5460.0 | 4183.333 to 5370.00 | 5509 |
| mean | 4140.00 | 3296.67 | ppm |
| SD | 580.00 | 551.11 | Sodium |
| % CV | 14.01 | 16.72 | exp 3360 to |
| range | 3270 to 5010.0 | 2470 to 4123.33 | 3571 |
| mean | 0.01 | 0.49 | ppm (mg/L) |
| SD | 0.01 | 0.12 | Ozone |
| % CV | 66.67 | 24.20 | |
| range | 0 to 0.0 | 0.31 to 0.66 | |

| | Sodium Decrease | Redox Increase |
|---|---|---|
| mean | 1246.67 | 540 |
| SD | 226.67 | 84 |
| % CV | 18.18 | 15.56 |
| range | 906.667 to 1586.7 | 414 to 666.0 |

Example 14a

A composition comprising at least one redox signaling agent (RXN10) and 50% NaOH were combined by first combining 75 μL 50% NaOH with 40 mL of RXN10. Chlorine levels of this combination were measured to be 24 ppm. To this combination of RXN10 and NaOH, Carbopol® was added to make a 0.9 wt % Carbopol®/99.1 wt % RXN10 mixture. The final chlorine levels of this combination were measured to be 9.6 ppm.

Example 14b

A composition made according to Example 1 (RXN9) and 50% NaOH were combined by first combining 50 μL 50% NaOH with 40 mL of RXN9. Chlorine levels of this combination were measured to be 22.6 ppm. To this combination of RXN9 and NaOH, Carbopol® was added to make a 0.9 wt % Carbopol®/99.1 wt % RXN9 mixture. The final chlorine levels of this combination were measured to be 9.2 ppm.

Example 14c

A comparison example was performed by combining 40 mL RXN10 and 0.36 g Carbopol® (0.9 wt % Carbopol®/99.1 wt % RXN10). The chlorine species for this mixture was initially measured at 13.6 ppm. To this RXN10-Carbopol® mixture, 75 μL 50% NaOH was added which allowed for gelling. After a few minutes, the chlorine species was measured at 7.6 ppm. After 48 hrs chlorine was measured to be 1.6 ppm.

Example 14d

A second comparison sample was made with RXN9 and Carbopol® (1% Carbopol®=1.0 wt % Carbopol®/99.wt % RXN9). To this 1% Carbopol®/RXN9 mixture, 263 4 of 50% NaOH was added. Chlorine in the final mixture was measured to be 6.4 ppm. 48 hrs later the chlorine was 0.8 ppm and the pH was 9.5.

Example 14e

A sample was prepared with RXN10 and Carbopol® (1% Carbopol®=1.0 wt % Carbopol®/99.wt % RXN1). To this 1% Carbopol®/RXN10 mixture, 225 4 of 50% NaOH was added. To this 1% Carbopol®/RXN10/225 μL of 50% NaOH mixture, 100 μL of 12.5% NaOCl was added and the chlorine level was found to be 1 ppm.

Example 14f

Another sample was prepared with RXN9 and Carbopol® (1% Carbopol®=1.0 wt % Carbopol®/99.wt % RXN9). To this 1% Carbopol®/RXN9 mixture, 225 4 of 50% NaOH was added. To this 1% Carbopol®/RXN9/225 μL of 50% NaOH mixture, 50 μL of 12.5% NaOCl was added and the chlorine level was found to be 1 ppm.

Example 14g

A third sample was prepared with RXN9 and Carbopol® (1% Carbopol®=1.0 wt % Carbopol®/99.wt % RXN9). To this 1% Carbopol®/RXN9 mixture, 277 4 of 50% NaOH was added. To this 1% Carbopol®/RXN9/277 μL of 50% NaOH mixture, 50 μL of 12.5% NaOCl was added and the chlorine level was found to be 10.8 ppm.

Example 14h

Comparison samples were made with a 2 wt % Carbopol®/RXN9 mixture. A sample was prepared with RXN9 and Carbopol® (2% Carbopol®=2.0 wt % Carbopol®/98 wt % RXN9). To this 2% Carbopol®/RXN9 mixture, 500 4 of 50% NaOH was added. To this 2% Carbopol®/RXN9/500 μL of 50% NaOH mixture, 50 μL of 12.5% NaOCl was added and the chlorine level was found to be 27 ppm.

Example 14i

Another comparison sample was prepared with RXN9 and Carbopol® (2% Carbopol®=2.0 wt % Carbopol®/98 wt % RXN9). To this 2% Carbopol®/RXN9 mixture, 500 4 of 50% NaOH was added. To this 2% Carbopol®/RXN9/500 μL of 50% NaOH mixture, 5 μL of 12.5% NaOCl was added and the chlorine level was found to be about 0 ppm.

Example 14j

To a 1% Carbopol®/RXN9 mixture, 225 μL of 50% NaOH was added as neutralizer, the pH was found to be neutral and the chlorine was 6 ppm. Subsequently, 100 μL of 12.5% OCl was added (pH of this mixture was 7) and the chlorine was immediately measured to be 21.2 ppm. After 5 mins, the chlorine was measured to be 50 ppm. After an additional 5 min, the chlorine was measured at 52 ppm.

Example 14k

To a second batch of 1% Carbopol®/RXN9 mixture, 225 μL of 50% NaOH and 100 μL of OCl were added, the pH was found to be 6 and the chlorine was measured at 50 ppm.

Example 14l

A separate mixture of 1% Carbopol®/RXN9 was prepared, the pH was 3 and the chlorine was measured as 13.2 ppm. To this 1% Carbopol®/RXN9 mixture, 225 μL of 50% NaOH was added and the resulting combination had a pH of 6 and chlorine levels of 8.4 ppm. To this 1% Carbopol®/RXN9/225 μL of 50% NaOH mixture, 50 μL of 12.5% NaOCl was added and the chlorine level was found to be 18 ppm. m

Examples 14m-14n

Additional comparison examples were made comprising a first mixture of 1% Carbopol®/RXN9, 225 μL of 50% NaOH and 50 μL of 12.5% NaOCl and a second mixture of 1% Carbopol®/RXN9, 225 μL of 50% NaOH and 100 μL of 12.5% NaOCl. The chlorine in the first mixture was measured as 19.4 ppm and the chlorine of the second mixture was measured as 54 ppm.

Examples 14o-14p

Another set of comparison examples were made comprising a first mixture of 1% Carbopol®/RXN9, 225 μL of 50% NaOH and 50 μL of 12.5% NaOCl and a second mixture of 1% Carbopol®/RXN9, 225 μL of 50% NaOH and 100 μL of 12.5% NaOCl. The chlorine in the first mixture was measured as 30 ppm and the chlorine of the second mixture was measured as 53 ppm.

Example 15 pH was tested while increasing NaOH added to a 0.9% gel (0.9 wt % Carbopol®/99.1 wt % RXN9). Initial pH of a mixture of 0.9 wt % Carbopol® and 99.1 wt % RXN9 was 3.1. NaOH was added incrementally as shown below.

| Amount of 50% NaOH added | pH | Chlorine |
| --- | --- | --- |
| 100 µL | 5.1 | |
| 25 µL | 6.0 | |
| 25 µL | 6.0 | |
| 50 µL | 6.0 | |
| 50 µL | 9 | 3.8 ppm |

Examples 16a-16b

Samples were made for APF testing comprising a first sample mixture of 1% Carbopol®/RXN9, 225 µL of 50% NaOH and 50 µL of 12.5% NaOCl and a second sample mixture of 1% Carbopol®/RXN9, 225 µL of 50% NaOH and 100 µL of 12.5% NaOCl. The chlorine in the first mixture was measured as 26.4 ppm and the chlorine of the second mixture was measured as 36 ppm. APF values of the first sample mixture as 200% and the APF value of the second sample mixture was 136%.

Examples 16c-16d

Additional samples were made and tested for pH, chlorine levels, APF and RPE. A first sample mixture of 1% Carbopol®/RXN9, 250 µL of 50% NaOH and 0 µL of 12.5% NaOCl was made and a second sample mixture of 1% Carbopol®/RXN9, 250 µL of 50% NaOH and 50 µL of 12.5% NaOCl was made. The results of each are shown in the table below:

| First Sample | | Second Sample | |
| --- | --- | --- | --- |
| pH | 6.5 | pH | 8 |
| Chlorine | 6 ppm | Chlorine | 30 ppm |
| APF | 14% | APF | 200% |
| RPE | 0% | RPE | 26% |

Prophetic Examples 17a-17h

A composition comprising at least one redox signaling agent (RXN10) and a metal silicate are combined. Chlorine, APF and R-PE levels are measured.

A composition made according to Example 1 (RXN9) and a metal silicate are combined. Chlorine, APF and R-PE levels are measured.

A composition made according to Example 1 (RXN9) and a metal silicate having the following composition: SiO2: 59.5%, MgO: 27.5%, Li2O: 0.8%, and Na2O: 2.8% are combined. The metal silicate is present at a weight percentage of 2%. Chlorine, APF and R-PE levels are measured.

A composition made according to Example 1 (RXN9) and a metal silicate having the following composition: SiO2: 59.5%, MgO: 27.5%, Li2O: 0.8%, and Na2O: 2.8% are combined. The metal silicate is present at a weight percentage of 3%. Chlorine, APF and R-PE levels are measured.

A composition made according to Example 1 (RXN9) and a metal silicate having the following composition: SiO2: 59.5%, MgO: 27.5%, Li2O: 0.8%, and Na2O: 2.8% are combined. The metal silicate is present at a weight percentage of 4%. Chlorine, APF and R-PE levels are measured.

A composition made according to Example 1 (RXN9) and a metal silicate having the following composition: SiO2: 59.5%, MgO: 27.5%, Li2O: 0.8%, and Na2O: 2.8% are combined. The metal silicate is present at a weight percentage of 5%. Chlorine, APF and R-PE levels are measured.

A composition made according to Example 1 (RXN9) and a metal silicate having the following composition: SiO2: 59.5%, MgO: 27.5%, Li2O: 0.8%, and Na2O: 2.8% are combined. The metal silicate is present at a weight percentage of 6%. Chlorine, APF and R-PE levels are measured.

Prophetic Example 18

A composition was made according to Example 3, except that 1 L of saline solution is electrolyzed for 20 minutes. In a separate vessel, a mixture of 4% LaponiteXLG and 96% deionized water is combined until said mixture gels. The aforementioned electrolyzed saline solution is combined with the gelled mixture of deionized water and LaponiteXLG. To this gel and electrolyzed saline solution, 0.2% wt of sodium phosphate monobasic is added. The resulting pH of the gel is measured at a pH of 7.6 and the chlorine is measured as 51.6 ppm.

Prophetic Example 19

A composition is made according to Example 1, except that the saline solution is electrolyzed for 20 minutes for every 1 L and 1000 L are prepared. In a separate vessel, a mixture of 4% LaponiteXLG and 96% deionized water is combined until said mixture gels. The volume of the mixture of 4% LaponiteXLG and 96% deionized water combined is 1000 L. The aforementioned electrolyzed saline solution is combined with the gelled mixture of deionized water and LaponiteXLG. To this gel and electrolyzed saline solution, 0.2% wt of sodium phosphate monobasic is added. The resulting pH of the gel is measured at a pH of 7.6 and the chlorine is measured as 51.6 ppm.

Prophetic Example 20

A composition is made according to Example 1, except that the saline solution is electrolyzed for 20 minutes for every 1 L and 1000 L are prepared. In a separate vessel, a mixture of 8% LaponiteXLG and 92% deionized water is combined until said mixture gels. The volume of the mixture of 8% LaponiteXLG and 92% deionized water combined is 1000 L. The aforementioned electrolyzed saline solution is combined with the gelled mixture of deionized water and LaponiteXLG. To this gel and electrolyzed saline solution, 0.2% wt of sodium phosphate monobasic is added. The resulting pH of the gel is measured at a pH of 7.6 and the chlorine is measured as 51.6 ppm.

Prophetic Example 21

A composition is made according to Example 1, except that the saline solution is electrolyzed for 20 minutes for every 1 L and 1000 L are prepared. In a separate vessel, a mixture of 8% LaponiteXLG and 92% deionized water is combined until said mixture gels. The volume of the mixture of 8% LaponiteXLG and 92% deionized water combined is 1000 L. The aforementioned electrolyzed saline solution is combined with the gelled mixture of deionized water and LaponiteXLG. To this gel and electrolyzed saline solution, 0.2% wt of sodium phosphate dibasic is added. The resulting pH of the gel is measured at a pH of 7.6 and the chlorine is measured as 51.6 ppm.

Examples 22a-22b

Characterization of a solution produced as described in Example 1 (Sample B) and saline solution (Sample A)

A composition produced as described in Example 1 was analyzed using EPR analysis. The procedure was conducted according to the following flow diagram and results:

---

Experimental design, Electron Paramagnetic Resonance (EPR) analysis and technical notes.

Experimental design:

1) Sample A

Sample A + EMPO ⟶ No EPR signal; Sample A + TMIO ⟶ No EPR signal

Result: No free radicals or oxidants were detected in Sample A.

2) Sample B

Sample B + EMPO ⟶ EMPO/*OH + EMPO/*CR$_3$ EPR signal; Sample B + TMIO ⟶ TMIO/*OH EPR signal Result: OH-radical adduct (TMIO) and mixture of OH— and carbon-centered radical adducts were detected in Sample B.

2A)

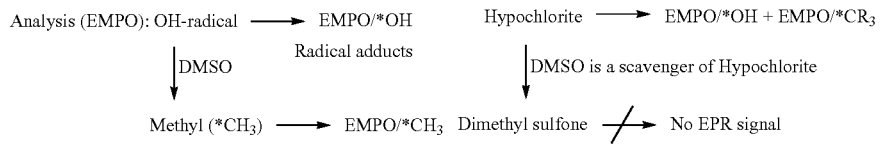

2B)

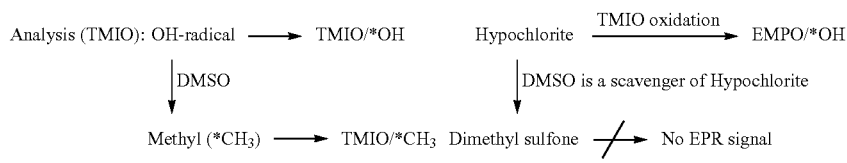

DMSO do not inhibit Free Radical adduct formation.
Only *OH produces secondary *CH$_3$-radical with DMSO.

DMSO completely scavengers Hypochlorite and block oxidation of spin traps to OH-adduct (non-radical oxidation).

Notes: EPR does not provide specific Hypochlorite detection. Hypochlorite presence was supported by positive control.
Reagents:
EMPO and TMIO were purchased from Enzo Life Science.
Spin trap concentrations were 100 mM final.
DMSO was added at 10%
EPR data acquisition:
EPR data were obtained at Bruker EMX EPR spectrometer using high sensitivity HS microwave cavity. CenterField: 3509 G;
Microwave Power: 40 mW; ScanTime: 200 sec; Modulation 1 G.

---

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

It is contemplated that numerical values, as well as other values that are recited herein are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or other multiple of the actual value indicated, and/or described in the disclosure.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

We claim:

1. A composition for topical application, comprising:
  a rheology modifier and an electrolyzed saline solution formulated as a gel,
    the rheology modifier comprising one or more of $SiO_2$, MgO, $Li_2O$, sodium magnesium silicate, and $Na_2O$, and
  the electrolyzed saline solution comprising:
    sodium at a concentration of 1000 to 1400 ppm,
    chloride present at a concentration from 1200 to 1600 ppm, and
    hypochlorous acid,
  wherein the electrolyzed saline solution further comprises a superoxide radical present at a concentration of 94 µM, wherein at least 95% of the superoxide radical is stable over a 13 month period.

2. The composition of claim 1, wherein the hypochlorous acid is present at a concentration of about 16 ppm to about 24 ppm or at a concentration of about 2300 ppm to about 2700 ppm.

3. The composition of claim 1, wherein the electrolyzed saline solution further comprises a hydroxyl radical present at a concentration of 241 µM or a hydroxyl radical present at a concentration of 0 to 10 ppm.

4. The composition of claim 1, wherein no hydroxyl radical is present in the composition.

5. The composition of claim 1, wherein the pH of the gel is between 6 and 9.

6. The composition of claim 5, wherein the pH of the gel is 7.6.

7. The composition of claim 1, wherein the rheology modifier comprises $SiO_2$ or sodium magnesium silicate.

8. A method of treating a subject using a composition comprising redox-signaling molecules, the method comprising:
  administering the composition of claim 1 to the subject.

9. A method of treating a fungal infection of a subject comprising contacting the fungal infection or an area infected with a fungus with a composition of claim 1 thereby reducing or ameliorating a fungal infection in the subject.

10. A method of reducing the presence of at least one fungus comprising contacting the at least one fungus with a composition of claim 1, thereby reducing the presence of at least one fungus.

11. The composition of claim 1, wherein the rheology modifier is present at a concentration of about 1% to about 2% by weight.

12. The composition of claim 1 further comprising a buffering agent.

13. The composition of claim 12, wherein the buffering agent is present in an amount of about 0.1% to about 5% by weight.

14. The composition of claim 12, wherein the buffering agent comprises sodium phosphate.

15. The composition of claim 1, wherein the gel has a viscosity that ranges from about 12,000 centipoise to about 20,000 centipoise.

16. The method of claim 8, wherein the composition is administered to the subject in an amount of 4 ounces twice daily.

17. The method of claim 9, wherein the composition is administered to the subject in an amount of 4 ounces twice daily.

18. The method of claim 10, wherein the composition is administered to the subject in an amount of 4 ounces twice daily.

* * * * *

UNITED STATES PATENT AND TRADEMARK OFFICE
CERTIFICATE OF CORRECTION

PATENT NO. : 10,543,230 B2  
APPLICATION NO. : 15/493019  
DATED : January 28, 2020  
INVENTOR(S) : Andrew Hoover et al.

Page 1 of 3

It is certified that error appears in the above-identified patent and that said Letters Patent is hereby corrected as shown below:

On the Title Page

In Column 2, item (56), U.S. Patent Documents, Line 8, delete "1/1997" and insert --10/1997--.

In Column 2, item (56), Other Publications, Lines 3-4, delete "Room-Termperature" and insert --Room-Temperature--.

In Column 2, item (56), Other Publications, Line 8, delete "H02/02-" and insert --$HO_2/O^-_2$--.

On the page 2, in Column 2, item (56), Other Publications, Line 18, delete "Room-Termperature" and insert --Room-Temperature--.

On the page 2, in Column 2, item (56), Other Publications, Line 22, delete "H02/02-" and insert --$HO_2/O^-_2$--.

On the page 2, in Column 2, item (56), Other Publications, Line 26, delete "triftuorophosphate" and insert --trifluorophosphate--.

In the Drawings

In sheet 2 of 24, FIG. 2, Line 16 (approx.), delete "H2O" and insert --$H_2O$--.

In the Specification

In Column 1, Line 39, delete "method an" and insert --method and--.

In Column 1, Line 47, delete "entireties" and insert --entireties.--.

In Column 1, Line 59, delete "a the" and insert --the--.

Signed and Sealed this  
Twelfth Day of May, 2020

Andrei Iancu  
*Director of the United States Patent and Trademark Office*

CERTIFICATE OF CORRECTION (continued)
U.S. Pat. No. 10,543,230 B2

In Column 5, Line 9, delete "hydroxyl xeradical" and insert --hydroxyl radical--.

In Column 7, Lines 42-57, delete "Carbopol® polymers....... triisopropanolamine." and insert the same in Column 7, Line 43 as a new paragraph.

In Column 8, Line 35, delete "0.70%, 0.80%," and insert --0.7%, 0.8%,--.

In Column 8, Line 36, delete "10%, 1.10%," and insert --1.0%, 1.1%,--.

In Column 8, Lines 36-37, delete "1.70%, 1.80%," and insert --1.7%, 1.8%,--.

In Column 8, Line 37, delete "2.10%," and insert --2.1%,--.

In Column 8, Line 38, delete "2.70%, 2.80/0," and insert --2.7%, 2.8%,--.

In Column 8, Line 38, delete "3.10%," and insert --3.1%,--.

In Column 8, Line 39, delete "3.70%, 3.80%," and insert --3.7%, 3.8%,--.

In Column 8, Line 39, delete "4.10%," and insert --4.1%,--.

In Column 11, Line 15, delete "iodidie," and insert --iodide,--.

In Column 13, Line 12 (approx.), delete "and or" and insert --and/or--.

In Column 13, Line 40, delete "and or" and insert --and/or--.

In Column 17, Line 9, delete "1$^{rst}$," and insert --1$^{st}$,--.

In Column 22, Line 34, delete "on" and insert --one--.

In Column 24, Line 5, delete "along side" and insert --alongside--.

In Column 25, Line 12, delete "2.8 ppth." and insert --2.8 ppt.--.

In Column 28, Line 4, delete "DIPPMPO/OH." and insert --DIPPMPO/OH·--.

In Column 28, Line 10, delete "OOH." and insert --OOH·--.

In Column 28, Line 36 (approx.), delete "(HNO-HOO.)" and insert --(HNO-HOO·)--.

In Column 28, Line 40 (approx.), delete "(HOCl-HOO.)." and insert --(HOCl-HOO·).--.

In Column 30, Line 66, delete "OH." and insert --OOH·--.

In Column 31, Line 13, delete "DIPPMPO/OH." and insert --DIPPMPO/OH·--.

CERTIFICATE OF CORRECTION (continued)
U.S. Pat. No. 10,543,230 B2

In Column 37, Line 5, delete "R-phycoetherin" and insert --R-phycoerythrin--.

In Column 37, Line 39, delete "R-phycoetherin" and insert --R-phycoerythrin--.

In Column 38, Line 44, delete "R-Phycoetherin" and insert --R-phycoerythrin--.

In Column 38, Line 60, delete "dihidrochloride," and insert --dihydrochloride,--.

In Column 41, Line 42, delete "R-Phycoetherin" and insert --R-phycoerythrin--.

In Column 41, Line 60 (approx.), delete "dihidrochloride," and insert --dihydrochloride,--.

In Column 50, Line 61, delete "then" and insert --than--.

In Column 51, Line 17, delete "liquid" and insert --liquid.--.

In Column 51, Line 19, delete "lighting" and insert --lighting.--.

In Column 51, Line 51, delete "triChloride" and insert --trichloride--.

In Column 52, Line 48, delete "(The" and insert --The--.

In Column 52, Line 49, delete "at ΔoC" and insert --at Δ° C.--.

In Column 52, Line 59 (approx.), Table 7, delete "100 C." and insert --100° C.--.

In Column 55, Line 28 (approx.), delete "2634 of" and insert --263 µL of--.

In Column 55, Line 37, delete "2254" and insert --225 µL--.

In Column 55, Line 46 (approx.), delete "2254" and insert --225 µL--.

In Column 55, Line 56 (approx.), delete "2774" and insert --277 µL--.

In Column 55, Line 66, delete "5004" and insert --500 µL--.

In Column 56, Line 8 (approx.), delete "5004" and insert --500 µL--.

In Column 56, Lines 38-39, delete "18 ppm. m" and insert --18 ppm.--.